US009011661B2

(12) United States Patent
Marziali et al.

(10) Patent No.: US 9,011,661 B2
(45) Date of Patent: *Apr. 21, 2015

(54) ENRICHMENT OF NUCLEIC ACID TARGETS

(71) Applicants: Boreal Genomics, Inc., Mountain View, CA (US); The University of British Columbia, Vancouver (CA)

(72) Inventors: Andrea Marziali, North Vancouver (CA); Nitin Sood, Los Altos, CA (US)

(73) Assignees: Boreal Genomics, Inc., Mountain View, CA (US); The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,697

(22) Filed: Sep. 9, 2013

(65) Prior Publication Data

US 2013/0344498 A1    Dec. 26, 2013

Related U.S. Application Data

(63) Continuation-in-part of application No. 13/593,143, filed on Aug. 23, 2012, now Pat. No. 8,529,744, which is a continuation-in-part of application No. 13/360,640, filed on Jan. 27, 2012, now Pat. No.

(Continued)

(51) Int. Cl.
*G01N 27/447* (2006.01)
*B03C 1/30* (2006.01)
*B03C 5/02* (2006.01)
(Continued)

(52) U.S. Cl.
CPC ........ *G01N 27/447* (2013.01); *G01N 27/44713* (2013.01); *G01N 2001/4038* (2013.01); *B03C 1/30* (2013.01); *B03C 5/026* (2013.01); *C12N 15/101* (2013.01); *C12Q 1/68* (2013.01)

(58) Field of Classification Search
USPC ......... 204/547, 643, 608, 609, 615, 458, 465, 204/457
See application file for complete search history.

(56) References Cited

U.S. PATENT DOCUMENTS 4,148,703 A    4/1979    Trop et al.
4,390,403 A    6/1983    Batchelder
(Continued)

FOREIGN PATENT DOCUMENTS

CA    2552262 A1    8/2005
CA    2523089 A1    4/2006
(Continued)

OTHER PUBLICATIONS

Asbury, et al., "Trapping of DNA by dielectrophoresis", Electrophoresis, 2002, 23:2658-2666.
(Continued)

*Primary Examiner* — Alex Noguerola
(74) *Attorney, Agent, or Firm* — Thomas C. Meyers; Brown Rudnick LLP

(57) ABSTRACT

Methods and apparatus providing improved fidelity and specificity when separating nucleic acids from a sample, but without need for amplification. In particular, using the disclosed methods, it is possible to isolate a variant nucleic acid (i.e., a mutation) from a non-target nucleic acid (i.e., a wild-type) when the variant is present in the original sample at a much lower concentration than the non-target, e.g., 1:10,000, without substantial loss of the variant.

22 Claims, 40 Drawing Sheets

Related U.S. Application Data 8,480,871, which is a continuation of application No. 10/597,307, filed as application No. PCT/CA2005/000124 on Feb. 2, 2005, now Pat. No. 8,133,371, said application No. 13/593,143 is a continuation-in-part of application No. 13/153,185, filed on Jun. 3, 2011, now Pat. No. 8,518,228.

(60) Provisional application No. 60/634,604, filed on Dec. 10, 2004, provisional application No. 60/540,352, filed on Feb. 2, 2004, provisional application No. 61/488,585, filed on May 20, 2011.

(51) Int. Cl.
*C12N 15/10* (2006.01)
*C12Q 1/68* (2006.01)
*G01N 1/40* (2006.01)

(56) References Cited

U.S. PATENT DOCUMENTS

| | | |
|---|---|---|
| 4,390,404 A | 6/1983 | Esho et al. |
| 4,732,656 A | 3/1988 | Hurd |
| 4,911,817 A | 3/1990 | Kindlmann |
| 4,971,671 A | 11/1990 | Slater et al. |
| 5,084,157 A | 1/1992 | Clark et al. |
| 5,185,071 A | 2/1993 | Serwer et al. |
| 5,286,434 A | 2/1994 | Slater et al. |
| 5,384,022 A | 1/1995 | Rajasekaran |
| 5,453,162 A | 9/1995 | Sabanayagam et al. |
| 5,609,743 A | 3/1997 | Sasagawa et al. |
| 5,641,628 A | 6/1997 | Bianchi |
| 5,938,904 A | 8/1999 | Bader et al. |
| 6,036,831 A | 3/2000 | Bishop |
| 6,110,670 A | 8/2000 | Van Broeckhoven et al. |
| 6,146,511 A | 11/2000 | Slater et al. |
| 6,193,866 B1 | 2/2001 | Bader et al. |
| 6,258,540 B1 | 7/2001 | Lo et al. |
| 6,693,620 B1 | 2/2004 | Herb et al. |
| 6,824,664 B1 | 11/2004 | Austin et al. |
| 6,827,830 B1 | 12/2004 | Slater et al. |
| 6,893,546 B2 | 5/2005 | Jullien et al. |
| 6,927,028 B2 | 8/2005 | Dennis et al. |
| 7,175,747 B2 | 2/2007 | Bayerl et al. |
| 7,198,702 B1 | 4/2007 | Washizu et al. |
| 7,371,533 B2 | 5/2008 | Slater et al. |
| 7,427,343 B2 | 9/2008 | Han et al. |
| 7,442,506 B2 | 10/2008 | Dhallan |
| 7,452,668 B2 | 11/2008 | Boles et al. |
| 7,838,647 B2 | 11/2010 | Hahn et al. |
| 7,888,017 B2 | 2/2011 | Quake et al. |
| 8,008,018 B2 | 8/2011 | Quake et al. |
| 8,133,371 B2 | 3/2012 | Marziali et al. |
| 8,182,666 B2 | 5/2012 | Marziali et al. |
| 8,195,415 B2 | 6/2012 | Fan et al. |
| 8,529,744 B2 * | 9/2013 | Marziali et al. ............... 204/457 |
| 2001/0045359 A1 | 11/2001 | Cheng et al. |
| 2002/0036139 A1 | 3/2002 | Becker et al. |
| 2002/0081280 A1 | 6/2002 | Curiel et al. |
| 2002/0119448 A1 | 8/2002 | Sorge et al. |
| 2002/0179445 A1 | 12/2002 | Alajoki et al. |
| 2003/0027178 A1 | 2/2003 | Vasmatzis et al. |
| 2003/0215855 A1 | 11/2003 | Dubrow et al. |
| 2005/0164241 A1 | 7/2005 | Hahn et al. |
| 2005/0164402 A1 | 7/2005 | Belisle et al. |
| 2005/0247563 A1 | 11/2005 | Shuber et al. |
| 2005/0247564 A1 | 11/2005 | Volkel et al. |
| 2007/0215472 A1 | 9/2007 | Slater et al. |
| 2007/0218494 A1 | 9/2007 | Slater et al. |
| 2008/0108063 A1 | 5/2008 | Lucero et al. |
| 2008/0314751 A1 | 12/2008 | Bukshpan et al. |
| 2009/0120795 A1 | 5/2009 | Marziali et al. |
| 2009/0139867 A1 | 6/2009 | Marziali et al. |
| 2009/0152116 A1 | 6/2009 | Boles et al. |
| 2010/0273219 A1 | 10/2010 | May et al. |
| 2010/0285537 A1 | 11/2010 | Zimmermann |
| 2011/0048950 A1 | 3/2011 | Marziali et al. |
| 2011/0152111 A1 | 6/2011 | Fan et al. |
| 2011/0245482 A1 | 10/2011 | Hahn et al. |
| 2011/0272282 A1 | 11/2011 | Marziali et al. |
| 2012/0035062 A1 | 2/2012 | Schultz et al. |
| 2012/0048735 A1 | 3/2012 | Marziali et al. |
| 2012/0160682 A1 | 6/2012 | Marziali et al. |
| 2012/0199481 A1 | 8/2012 | Marziali et al. |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| EP | 0356187 A2 | 2/1990 |
| EP | 1720636 A1 | 11/2006 |
| EP | 1859249 A0 | 11/2007 |
| EP | 2238434 A0 | 10/2010 |
| EP | 2458004 A1 | 5/2012 |
| GB | 2249395 A | 5/1992 |
| JP | 7-167837 A | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 9945374 A2 | 9/1999 |
| WO | 2001031325 A1 | 5/2001 |
| WO | 2002042500 A2 | 5/2002 |
| WO | 2003019172 A2 | 3/2003 |
| WO | 2005072854 A1 | 8/2005 |
| WO | 2006063625 A1 | 6/2006 |
| WO | 2006081691 A1 | 8/2006 |
| WO | 2007092473 A2 | 8/2007 |
| WO | 2009094772 A1 | 8/2009 |
| WO | 2010051649 A1 | 5/2010 |
| WO | 2010/104798 A1 | 9/2010 |
| WO | 2010121381 A1 | 10/2010 |
| WO | 201302616 A2 | 1/2013 |

OTHER PUBLICATIONS

Asbury, et al., "Trapping of DNA in Nonuniform Oscillating Electric Fields", Biophysical Journal, 1998, 74:1024-1030.

Astumian, et al., "Fluctuation Driven Ratchets: Molecular Motors", Physical Review Letters, 1994, 72(11):1766-1769.

Baba, Yoshinobu, "Capillary Affinity Gel Electrophoresis", Molecular Biotechnology, 1996, (9):1-11.

Bier, Martin, et al., "Biasing Brownian Motion in Different Directions in a 3-State Fluctuating Potential and an Application for the Separation of Small Particles", Physical Review Letters, 1996, 76(22):4277-4280.

Broemeling, D., et al., "An Instrument for Automated Purification of Nucleic Acids from Contaminated Forensic Samples", JALA 2008, 13, 40-48.

Carle, G.F., et al., "Electrophoretic Separations of Large DNA Molecules by Periodic Inversion of the Electric Field", Science, 1986, 232(4726):65-68.

Chacron, M.J., et al., "Particle trapping and self-focusing in temporarily asymmetric ratchets with strong field gradients", Physical Review E, 1997, 56(3):3446-3450.

Chakrabarti, Subrata, et al., "Highly Selective Isolation of Unknown Mutations in Diverse DNA Fragments: Toward New Multiplex Screening in Cancer", American Association for Cancer Reserch, 2000, 60:3732-3737.

Chan, K.C. Allen, et al., "Size Distributions of Maternal and Fetal DNA in Maternal Plasma", Molecular Diagnostics and Genetics, Clinical Chemistry, 2004, 50(1):88-92.

(56) References Cited

OTHER PUBLICATIONS

Chu, Gilbert, "Bag model for DNA migration during pulsed-field electrophoresis", Proc. Natl. Acad. Sci., 1991, 88:11071-11075.
European Search Report corresponding to EP11004417, Mar. 29, 2012, 4 pages.
Frumin, L.L., et al., "Anomalous size dependence of the non-linear mobility of DNA", in PhysChemComm, 2000, 11 (3):61-63.
Frumin, L.L., et al., "Nonlinear focusing of DNA macromolecules", Physical Review E—Statistical, Nonlinear and Soft Matter Physics, 2001, 64:021902-1-5.
Griess, Gary A., et al., "Cyclic capillary electrophoresis", Electrophoresis, 2002, 23:2610-2617.
International Preliminary Report on Patentability corresponding to PCT/CA2005/000124, Aug. 7, 2006, 8 pages.
International Preliminary Report on Patentability corresponding to PCT/CA2006/000172, Aug. 7, 2007, 8 pages.
International Preliminary Report on Patentability corresponding to PCT/CA2009/000111, Aug. 3, 2010, 9 pages.
International Seach Report and Written Opinion for PCT/US13/39553 dated Sep. 18, 2013, pp. 13.
International Search Report dated Feb. 23, 2010 corresponding to PCT/CA2009/001648, 6 pages.
International Search Report for PCT/CA2006/000172, International Searching Authority, Jun. 2, 2006, 4 pages.
International Search Report for PCT/CA2012/050576, Feb. 28, 2013 3 pages.
Jorgez, Carolina J., et al., "Quantity versus quality: Optimal methods for cell-free DNA isolation from plasma of pregnant women", American College of Medical Genetics, 2006, 8(10):615-619.
Kitzman, Jacob O., et al., "Noninvasive Whole-Genome Sequencing of a Human Fetus", Sci Transl Med 4, 137ra76 (2012); DOI: 10.1126/scitranslmed.3004323, 9 pages.
Kopecka, K., et al., "Capillary electrophoresis sequencing of small ssDNA molecules versus the Ogston regime: Fitting data and interpreting parameters", Electrophoresis, 2004, 25(14):2177-2185.
LaLande, Marc, et al., "Pulsed-field electrophoresis: Application of a computer model to the separation of large DNA molecules", Proc. Natl. Acad. Sci. USA, 1987, 84:8011-8015.
Lun, Fiona M. F., et al., "Microfluidics Digital PCR Reveals a Higher than Expected Fraction of Fetal DNA in Maternal Plasma", Molecular Diagnostics and Genetics, Clinical Chemistry, 2008, 54(10):1664-1672.
Magnasco, Marcelo, O., "Forced Thermal Ratchets", Physical Review Letters, 1993, 71(10):1477-1481.
Makridakis, Nick M., "PCR-free method detects high frequency of genomic instability in prostate cancer", Nucleic Acids Research, 2009, 37(22):7441-7446.
Marziali, A., et al., "Novel electrophoresis mechanism based on synchronous alternating drag perturbation", Electrophoresis 2005, 26:82-90, published on-line Dec. 29, 2004 at URL www.3.interscience.wiley.com/cgi-bin/issue/109861245.
Nollau, Peter, et al., "Methods for detection of point mutations: performance and quality assessment", Department of Clinical Chemistry, 1997, 43(7):1114-1128.
Office Action mailed Aug. 19, 2011 for U.S. Appl. No. 11/815,760.
Office Action mailed Dec. 27, 2010 for U.S. Appl. No. 11/815,760.
Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.
Pel, J., et al., "Nonlinear electrophoretic response yields a unique parameter for separation of biomolecules", PNAS 2009, vol. 106, No. 35, 14796-14801.
Rousseau, J., et al., "Gel electrophoretic mobility of single-stranded DNA: The two reptation field-dependent factors", Electrophoresis, 2000, 21(8):1464-1470.
Sikora, Aleksandra, et al., "Detection of Increased Amounts of Cell-Free DNA with Short PCR Amplicons", Clinical Chemistry, 2010, 56(1):136-138.
Slater, G.W., et al., "Recent developments in DNA electrophoretic separations", Electrophoresis, 1998, 19 (10):1525-1541.
Slater, G.W., et al., "The theory of DNA separation by capillary electrophoresis", Current Opinion in Biotechnology, 2003, 14:58-64.
Slater, G.W., et al., "Theory of DNA electrophoresis: A look at some current challenges", Electrophoresis, 2000, 21:3873-3887.
So. A., et al., "Efficient genomic DNA extraction from low target concentration bacterial cultures using SCODA DNA extraction technology", Cold Spring Harb Protoc, 2010, 1150-1153; 1185-1198.
Supplementary European Search Report corresponding to EP09706657, May 12, 2011, 2 pages.
Supplementary Partial European Search Report corresponding to EP05706448, May 14, 2012, 3 pages.
Tessier, F., et al., "Strategies for the separation of polyelectrolytes based on non-linear dynamics and entropic ratchets in a simple microfluidic device", Applied Physics A—Materials Science & Processing, 2002, 75:285-291.
Turmel, C., et al., "Molecular detrapping and band narrowing with high frequency modulation of pulsed field electrophoresis", Nucleic Acids Research, 1990, 18(3):569-575.
Viovy, J.L., "Electrophoresis of DNA and other polyelectrolytes: Physical mechanisms", Review of Modern Physics, 2000, 72(3):813-872.
Wright, Caroline, "Cell-free fetal nucleic acids for non-invasive prenatal diagnosis", Report of the UK export working group, Jan. 2009, 64 pages.
Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.

* cited by examiner

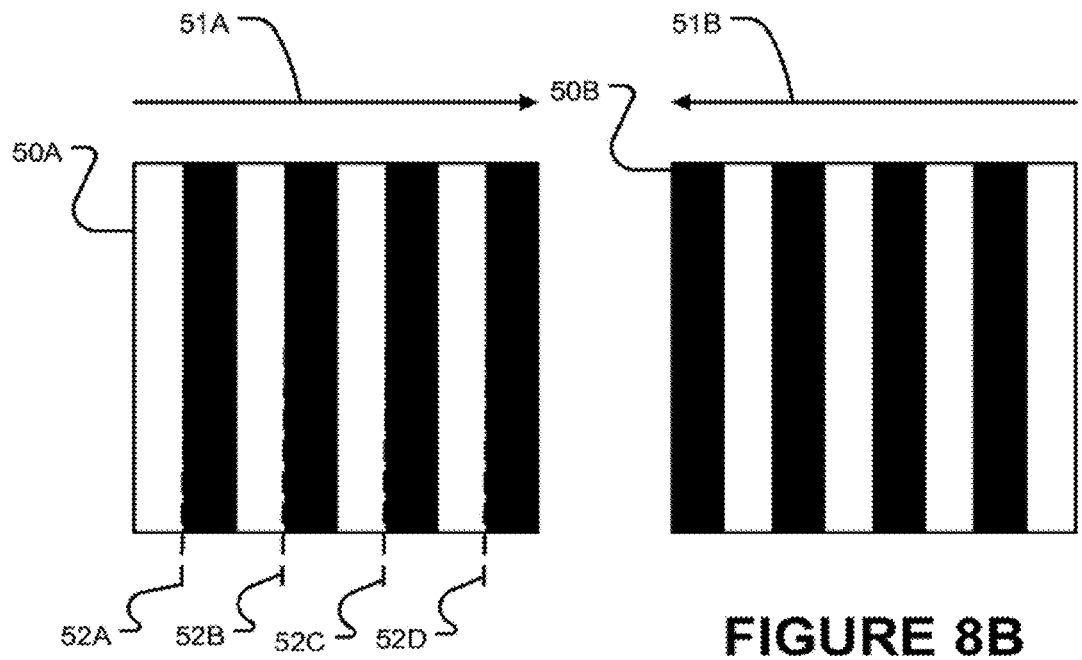
FIGURE 8A
FIGURE 8B
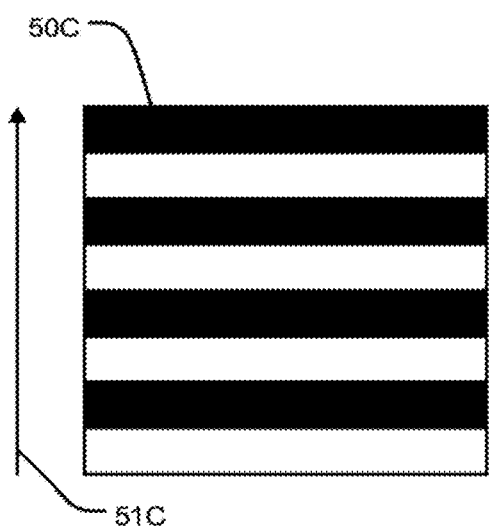
FIGURE 8C
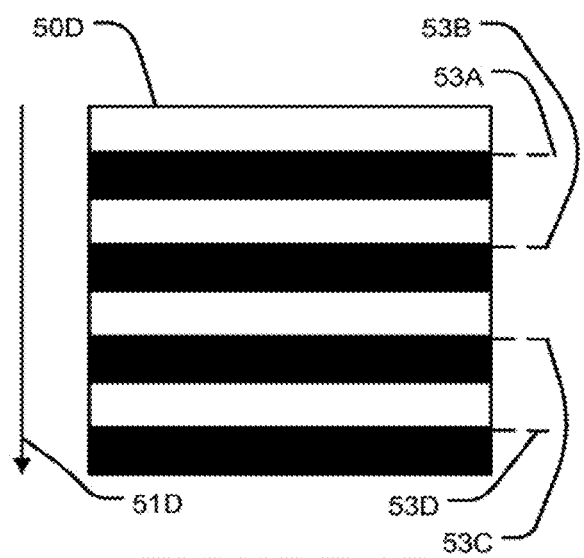
FIGURE 8D

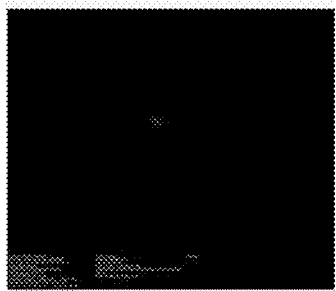 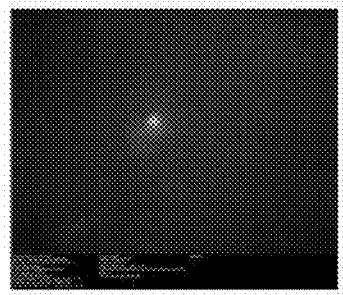 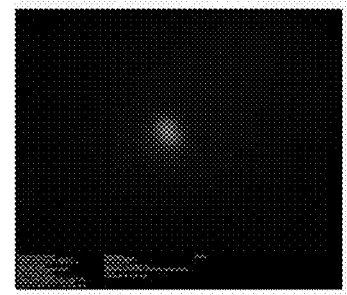
FIGURE 27A     FIGURE 27B     FIGURE 27C
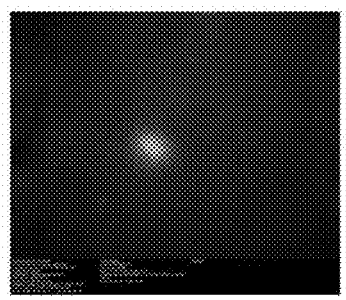
FIGURE 27D

```
SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 1
actggccgtc gttttact                                                       18

<210> SEQ ID NO 2
<211> LENGTH: 100
<212> TYPE: DNA
<213> ORGANISM: Artificial Sequence
<220> FEATURE:
<223> OTHER INFORMATION: synthetic sequence

<400> SEQUENCE: 2
cgattaagtt gagtaacgcc actattttca cagtcataac catgtaaaac gacggccagt         60
gaattagcga tgcatacctt gggatcctct agaatgtacc                              100

<210> SEQ ID NO 3
<211> LENGTH: 100
<212> TYPE: DNA
<213> ORGANISM: Artificial Sequence
<220> FEATURE:
<223> OTHER INFORMATION: synthetic sequence

<400> SEQUENCE: 3
cgattaagtt gagtaacgcc actattttca cagtcataac catgtaaaac tacggccagt         60
gaattagcga tgcatacctt gggatcctct agaatgtacc                              100
```

ENRICHMENT OF NUCLEIC ACID TARGETS

CROSS-REFERENCE TO RELATED APPLICATIONS

This application is a continuation-in-part of U.S. Ser. No. 13/593,143, filed Aug. 23, 2012, which is a continuation-in-part of U.S. application Ser. No. 13/360,640, filed Jan. 27, 2012, which is a continuation of U.S. application Ser. No. 10/597,307, which is a 371 of International Application No. PCT/CA2005/000124, filed Feb. 2, 2005, which claims the benefit of U.S. application No. 60/540,352, filed Feb. 2, 2004, and U.S. application No. 60/634,604, filed Dec. 10, 2004. U.S. Ser. No. 13/593,143 is additionally a continuation-in-part of U.S. application Ser. No. 13/153,185, filed Jun. 3, 2011, which claims the benefit of U.S. application Ser. No. 61/488,585, filed May 20, 2011. All of the aforementioned applications are hereby incorporated by reference in their entireties.

TECHNICAL FIELD

The invention relates to methods and apparatus for moving, concentrating, and enriching particles. The invention has application, for example, in moving, concentrating, or enriching a wide range of biological molecules, such as nucleic acids, proteins, bio-macromolecules, and organic or inorganic ions.

BACKGROUND

Standard nucleic acid separation techniques limit researchers' abilities to analyze samples for nucleic acids that are present in low abundance, such as mutations. In particular, it is difficult to resolve rare nucleic acids which are present at low concentrations in the presence of closely-related nucleic acids, e.g., wild-type DNA. To overcome this problem, typically all of the nucleic acids in a sample are amplified prior to isolation and analysis. For example, using Polymerase Chain Reaction (PCR) amplification, each nucleic acid can be amplified one million times (or more). Theoretically, there will be a million-fold increase of each nucleic acid originally present, and, thus, a greater opportunity to isolate and find the nucleic acids in low abundance.

In practice, however, PCR amplification has significant drawbacks when it is used to analyze nucleic acids that are present in low abundance. The PCR reaction is stochastic and to the extent that a low-abundance nucleic acid is not amplified in the first few rounds of PCR, it likely will not be detected. In addition, PCR amplification introduces sequence errors in the amplicons. If the error rate is high enough, there can be a significant effect on the resulting sequence data, especially in applications requiring the detection of rare sequence variants.

Unfortunately, a viable alternative to sequencing plus amplification does not exist. Commonly-available separation techniques do not have the resolution or fidelity to pull enough low-abundance nucleic acids from a background to be useful. In fact, most separation methods require an amplification step, either before or after separation, to recover enough low-abundance nucleic acid for further analysis, e.g. sequencing.

For many years, nucleic acids have been separated from each other using electrophoresis. Electrophoresis involves directing the movement of charged particles in a medium, such as a gel or liquid solution by applying an electric field across the medium. The electric field may be generated by applying a potential across electrodes that are placed in contact with the medium such that electric current can be conducted into the medium. The movement of the particles in the medium is affected by the magnitude and direction of the electric field, the electrophoretic mobility of the particles and the mechanical properties, such as viscosity, of the medium. Through electrophoresis, particles that are distributed in a medium can be transported through the medium. Electrophoresis is commonly used to transport nucleic acids (such as DNA or RNA) through gel substrates. Because different species have different electrophoretic mobilities, electrophoresis may be used to separate different species from one another. Conventional electrophoresis techniques are largely limited in application to the linear separation of charged particles. Using conventional electrophoresis techniques, a direct current (DC) electric field or an alternating pulsed-field electrophoretic (PFGE) field is typically applied to a medium so that particles in the medium are transported toward an electrode.

Electrophoresis may be used to transport fragments of DNA or other microscopic electrically charged particles. Various electrophoresis methods are described in Slater, G. W. et al. *Electrophoresis* 2000, 21, 3873-3887. Electrophoretic particle transport is typically performed in one dimension by applying a direct current (DC) electric field between electrodes on either side of a suitable electrophoresis gel. The electric field causes electrically charged particles in the gel to move toward one of the electrodes. Because the particles experience different mobilities through the gel due to the DC field, the particles can be separated. In an alternate application, an asymmetric alternating current (AC) waveform can cause net drift of electrophoretic particles due to nonlinearity of the relationship between particle speed and applied electric field. This effect can be used to cause particles to move in one dimension as described in Chacron, M. J., et al. *Phys. Rev. E* 1997, 56, 3446-3450; Frumin, L. L, et al. *Phys. Chem. Commun.* 2000, 11; and, Frumin, L. L. et al. *Phys. Rev. E* 2001, 64, 021902. Additionally, Pohl, H. A., *Dielectrophoresis: The Behavior of Neutral Matter in Nonuniform Electric Fields* Cambridge University Press, Cambridge, UK 1978; Asbury, C. L., et al., *Electrophoresis* 2002, 23, 2658-2666; and Asbury, C. L., et al. *Biophys. J.* 1998, 74, 1024-1030 discloses that dielectrophoresis can be applied to concentrate DNA in two or more dimensions. However, applications of dielectrophoresis have required undesirably high electric field gradients, resulting in breakdown of the separation media or the samples. Each of these references is incorporated herein in its entirety.

Electrophoresis can also be used to concentrate particles in a particular location. A problem that can interfere with the successful use of electrophoresis for concentrating particles is that there must be an electrode at the location where the particles are to be concentrated. Electrochemical interactions between the electrodes and particles can degrade certain kinds of the particles. For example, where the particles comprise DNA, the DNA can be damaged by electrochemical interactions at the electrodes. Additionally, electric fields present during conventional direct current electrophoresis are divergence-free everywhere except at electrodes which can source or sink electric current. Thus, electrophoresis is typically applied in cases where particles are caused to move toward an electrode. Once concentrated, the particles can be obtained by cutting out the portion of the medium in which the particles have been concentrated. The particles can then be separated from the medium by using various purification techniques.

Additional methods of nucleic acid separation are known. References that describe methods for DNA separation include: Slater et al. The theory of DNA separation by capillary electrophoresis *Current Opinion in Biotechnology* 2003 14:58-64; Slater et al. U.S. Pat. No. 6,146,511 issued 14 Nov. 2000; Frunin et al. Nonlinear focusing of DNA macromolecules *Phys. Rev. E* 64:021902; Griess et al. Cyclic capillary electrophoresis *Electrophoresis* 2002, 23, 2610-2617 Wiley-VCH Verlag GmbH & Co. Weinheim (2002). References which describe the use of fields to separate particles include: Bader et al. U.S. Pat. No. 5,938,904 issued on Aug. 17, 1999; Bader et al. U.S. Pat. No. 6,193,866 issued on 27 Feb., 2001; Tessier et al: Strategies for the separation of polyelectrolytes based on non-linear dynamics and entropic ratchets in a simple microfluidic device *Appl. Phys. A* 75, 285-291 (2002); Chacron et al. Particle trapping and self-focusing in temporally asymmetric ratchets with strong field gradients *Phys. Rev. B* 56:3 3446-3550 (September 1997); Dean et al. Fluctuation driven ratchets: molecular motors *Phys. Rev. Lett.* 72:11 1766-1769 (14 Mar. 1994); Bier et al. Biasing Brownian motion in different directions in a 3-state fluctuating potential and an application for the separation of small particles *Phys. Rev. Lett.* 76:22 4277-4280 (27 May, 1996); Magnasco, Forced thermal ratchets *Phys. Rev. Lett.* 71:10 1477-1481 (6 Sep. 1993). Each of these references is incorporated herein in its entirety.

There is a need for techniques that provide for high fidelity enrichment of nucleic acids without introducing errors into the sample and with an ability to isolate rare nucleic acids in a sample and to resolve nucleic acids having similar sequences.

SUMMARY OF THE INVENTION

The invention provides improved methods for recovering nucleic acids from a sample by enriching the sample for a desired nucleic acid species, rather than removing those species directly from the sample. Methods of the invention are fundamentally different from conventional separation techniques in that methods of the invention create a subsample in which a target that was present in only a small amount in the original sample becomes the dominant nucleic acid species in the subsample. For example, a dominant background nucleic acid species may be driven from a sample into a waste well, leaving behind only target nucleic acids. As a result, a low-abundance species, for example a nucleic acid target that would be difficult to detect using conventional techniques that are biased toward the predominant species, is readily detected using methods of the invention.

Methods of the invention make it is possible to separate closely-related nucleic acid targets, which may differ in concentration by orders of magnitude, without substantial loss of the nucleic acid, the detection of which is desired. Accordingly, the invention provides many of the advantages of conventional nucleic acid separation and amplification techniques (high specificity, high sensitivity, and high speed) without the drawbacks of those techniques (sample loss, introduction of errors, high cost). Methods of the invention are useful to isolate a target nucleic acid (i.e., a mutation) from a non-target nucleic acid (i.e., a wild-type) when the target is present in the original sample at a much lower concentration than the non-target. Unlike many of the prior art methods, however, methods of the invention enrich the sample for the target nucleic acid rather than remove the target nucleic acid from the sample. Using methods of the invention, it is possible to enrich a sample for a target nucleic acid 1000, 10,000, 100,000 or even 1,000,000-fold. This fidelity allows the target nucleic acid to be directly sequenced using next generation sequencing. Alternatively, the target nucleic acid can be amplified after enrichment, prior to further processing, e.g., sequencing. In this case, because the target starting material has been isolated from the massive excess of non-target nucleic acids, there is much less concern for PCR errors in non-target nucleic acids giving rise to phantom target nucleic acids.

In one instance, the invention provides a method to enrich a sample from a target nucleic acid to non-target nucleic acid ratio of X to a target nucleic acid to non-target nucleic acid ratio of Y, where Y is at least 10 times greater than X. The method includes obtaining a sample including a non-target nucleic acid and a target nucleic acid, and enriching the sample for the target. In some examples, the enrichment includes applying one or more periodic fields to the sample. The method can be achieved even if the target and the non-target differ by only a single base, and the method does not generate any new molecules during the enriching step. Of course, the target and the non-target nucleic acids can differ by more than a single base, for example 20 or fewer bases. In other instances, the target and non-target nucleic acids will differ by their methylation, acetylation, or other chemical modification patterns. The target and non-target nucleic acids having differing methylation or acetylation patterns may have the same sequence or they can have different sequences.

Methods of the invention are used to enrich samples for low-abundance nucleic acids that are important in early diagnosis. The invention allows resolution of different nucleic acids without amplification in the isolating step and without regard for the sequence difference between a nucleic acid and a variant of it. Accordingly, use of the invention allows detection and analysis of nucleic acids present in low abundance in biological samples, such as tissue biopsies, or non-invasive samples, such as blood or urine. The ability to interrogate low-abundance nucleic acids is especially important in cancer diagnostics, where early detection enables effective treatment. For example, identification of the presence of a specific mutation may suggest a particular treatment regimen (e.g., surgery versus radiation therapy) or suggest that a first line treatment is likely to be ineffective, (e.g., the cancer is resistant to docetaxel). Additionally, when mutational events are detected earlier, patients typically have more options for treatment, as well as the time to identify a preferred treatment provider.

Methods of the invention are useful in any sample. Preferred samples are derived from tissue or body fluid, for example, tissues, blood, sputum, sweat, urine, tears, feces, aspirates, or a combination thereof. Typically, the biological sample will be from a human, however the methods of the invention may be used to recover nucleic acids from many organisms, including, mammals. Moreover, methods of the invention are useful for the isolation, detection, and interrogation of proteins, as will be evident from consideration of the detailed description below.

Once a sample is enriched for a target, it will typically be useful to identify the target using sequencing, hybrid capture, antibodies or other known techniques. Once the target nucleic acid is identified, it will be possible to correlate its presence in the sample with a condition, or a likely outcome for the subject from which the sample was taken. For example, the presence of the target nucleic acid may be indicative of a genetic disorder or cancer. Additionally, because the methods of the invention can be used to enrich a sample for multiple targets (serially or in parallel), the invention lends itself to diagnosing diseases by identifying specific biomarker panels that correlate with specific diseases. In some instances the invention will allow the identification of 5 or more targets, e.g., 10 or more targets, e.g., 20 or more targets, e.g., 50 or more targets, e.g., 100 or more targets. Furthermore, when screening panels comprising multiple biomarkers are used, the confidence in the resulting diagnosis is increased. That is, a diagnosis based upon identifying one target nucleic acid may be the result of noise or error, but when a diagnosis is based upon identifying 10 or more targets simultaneously, it is very likely not the result of noise or error.

In some cases, the target nucleic acid will be present in low-abundance with respect to the corresponding wild-type species, and enrichment may result in increasing the ratio of target to non-target nucleic acids by at least 100 times or at least 1000 times. In some instances, nucleic acids to be analyzed will be "short" nucleic acids, e.g., having 500 or fewer bases, e.g., having 200 or fewer bases, e.g., having 100 or fewer bases, e.g., having 50 or fewer bases, e.g., having 30 or fewer bases.

In another instance, the invention provides a method for enriching a sample, including obtaining a sample having a non-target nucleic acid and a target nucleic acid, wherein the target to non-target ratio in the sample is X, and applying a periodic field to the sample in order to generate, independent of non-target or target size, a subsample having a target to non-target ratio of Y, wherein Y is greater than X. In this instance no new molecules are generated in the sample during the applying step.

In another instance, the invention provides a method for enriching a sample for a nucleic acid, including obtaining a sample comprising a first nucleic acid and a second nucleic acid, wherein the second nucleic acid to first nucleic acid ratio in the sample is X, and applying a periodic field to the sample in order to generate, independent of nucleic acid size, a subsample having a second nucleic acid to first nucleic acid ratio of Y, wherein Y is at least 10 times greater than X. In this instance no new molecules are generated in the sample during the applying step. In this instance, the first and second nucleic acids may be from a mammal, e.g., a human. Additionally, because of the selectivity of the method it is possible to enrich the sample for a second nucleic acid that originates from a second mammal, while the sample was recovered from a first mammal. For example, the second mammal may be a fetus and the first mammal the mother of the fetus, or the second mammal may be an assailant and the first mammal a victim or another individual. In a specific example, the sample may be maternal blood and the first nucleic acid is a maternal nucleic acid and the second nucleic acid is a fetal nucleic acid.

Other aspects of the invention provide methods for causing motion of particles in a medium. Those methods are useful for concentrating particles and/or for separating particles of different types from one another. Such methods comprise applying a time-varying driving field to the particles. The driving field applies a time-varying driving force alternating in direction to the particles. The methods also comprise applying a mobility-varying field to the particles. The mobility-varying field is one or both of: different in type from the driving field, and non-aligned with the driving field. The driving field and mobility-varying field are applied simultaneously during a period and the mobility-varying field causes a mobility of the particles in the medium to be time dependent during the period, in a manner having a non-zero correlation with the driving field over the period. These methods may be called SCODA methods.

Another aspect of the invention provides methods and apparatus for extracting charged particles from a medium. Those methods are useful for extracting particles from a medium in which the particles have been concentrated by SCODA and may also be applied to extracting from a medium particles that have not been concentrated by SCODA. A buffer in an extraction reservoir is placed to abut a medium containing the particles to be extracted at a buffer-gel interface. Electrodes are provided on each side of the buffer-gel interface. By applying a pulsed voltage potential to the electrodes (wherein the time-averaged electric field is zero), zero-integrated-field electrophoresis (ZIFE) is applied to the buffer-gel interface to direct the particles in the gel into the extraction reservoir, where the particles are collected and concentrated.

Another method disclosed comprises placing a buffer extraction reservoir next to a gel solution containing the charged particles to be extracted; applying ZIFE to the buffer-gel interface to direct the particles into the extraction reservoir; and collecting and concentrating the particles in the extraction reservoir. A pipette or other device may then be used to suction the particles from the extraction reservoir. In some embodiments of the invention, the apparatus comprises a gel boat holding a gel that contains the charged particles to be extracted. A capillary containing a small amount of buffer is inserted into the gel solution. A pipette or other device is provided in the capillary for suctioning the particles that have collected in the buffer. Electrodes are provided on each side of the buffer-gel interface for generating an electric field.

Further aspects of the invention and features of specific embodiments of the invention are described below.

BRIEF DESCRIPTION OF THE DRAWINGS

FIGS. 8A, 8B, 8C, and 8D show optical mask patterns that may be used to cause concentration of particles at an array of spots.

FIG. 24A shows the SCODA velocity field for perfect match target. A circular spot indicates final focus location. FIG. 24B shows the SCODA velocity field for the single base mismatch target.

FIGS. 27A, 27B, 27C, and 27D show the results of performing SCODA focusing with different concentrations of probes and in the presence or absence of 200 mM NaCl. Probe concentrations are 100 µM, 10 µM, 1 µM, and 100 µM, respectively. The buffer used in FIGS. 27A, 27B, and 27C was 1×TB with 0.2 M NaCl. The buffer used in FIG. 27D was 1×TBE. Different amounts of target were injected in each of these experiments, and the camera gain was adjusted to prevent saturation.

FIGS. 35A and 35B show the results of an initial focus before washing unmethylated target from the gel for 10 µmol unmethylated DNA (FIG. 35A) and 0.1 µmol methylated DNA (FIG. 35B). FIGS. 35C and 35D show the results of a second focusing conducted after the unmethylated sequence had been washed from the gel for unmethylated and methylated target, respectively.

FIG. 36A shows the gel after loading. FIGS. 36B and 36C show focusing at 55° C. after 2 minutes and 4 minutes, respectively. FIGS. 36D and 36E show focusing at 62° C. after 2 minutes and 4 minutes, respectively. FIGS. 36F, 36G, and 36H show focusing of the target molecules to an extraction well at the center of the gel after 0.5 minutes and 1 minute at 55° C. and at 3 minutes after raising the temperature to 62° C., respectively.

FIGS. 36I, 36J, and 36K show the application of a washing bias to the right at 55° C. after 6 minutes, 12 minutes and 18 minutes, respectively.

DESCRIPTION

Figure 1A:
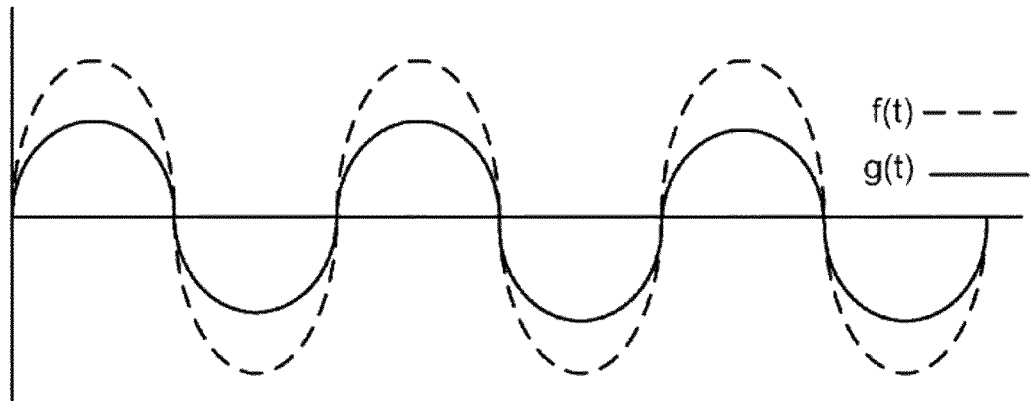
FIGS. 1A through 1I are examples of possible waveforms for driving and mobility-modifying fields.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Methods of the invention provide the ability to isolate low-abundance biological molecules from a sample. The invention provides for enriching low-abundance variants of a biological molecule relative to more common, or wild-type, variants of the molecule. In preferred embodiments, methods of the invention are used to create a subsample in which a molecular species that was present in the original sample in low-abundance relative to a more common species (e.g., a mutated nucleic acid and its wild-type equivalent) is present in relative high abundance in the subsample.

The skilled artisan will appreciate that there are numerous ways to practice the invention described and claimed herein. However, one preferred embodiment is exemplified below using a technique called scodaphoresis or SCODA (Synchronous Coefficient of Drag Alteration). Scodaphoresis refers to methods for moving and/or concentrating particles in a medium. Scodaphoresis involves exposing particles that are to be moved and/or concentrated to two time-varying fields or stimuli. A first one of the fields results in a force f(t) that drives motion of the particles in the medium. The direction of particle motion caused by the interaction of the particle with the first field varies in time. The first field may provide a driving force that averages to zero over an integral number of cycles of the first field.

A second one of the fields alters the mobility of the particles in the medium according to a function g(t). The first and second fields are such that f(t) and g(t) have a non-zero correlation over a time period of interest. Achieving such a non-zero correlation can be achieved in various ways. In some embodiments, f(t) and g(t) are each time varying at the same frequency and f(t) and g(t) are synchronized so that there is a substantially constant phase relationship between f(t) and g(t). In other embodiments, f(t) has a frequency that is twice that of g(t).

Application of the fields to the particles causes a net drift of the particles. This net drift can be harnessed to separate particles of different types or to concentrate (enrich) particles in selected areas, or both. As discussed below, the first and second fields may be of the same type (homogeneous SCODA) or of different types (heterogeneous SCODA).

As a demonstration of SCODA, consider the case where:

$$f(t)=\sin(\omega t), g(t)=\sin(\omega t), \text{ and } v(f(t),g(t))= f(t)\times(\mu_0+\mu_1 g(t)) \quad (1)$$

where $\mu_0$, is the unperturbed mobility of the particle in the medium and $\mu_1$ is the susceptibility of the mobility to g(t). It can be seen that in the absence of g(t), the velocity of the particle is given simply by $\mu_0 f(t)$. Where f(t) is given by Equation (1) there is no net displacement of the particle over a cycle of f(t). Where g(t) is as given above, however, over one cycle, the velocity integrates to yield a distance, d, traveled by the particle of:

$$d = \int_{t=0}^{2\pi/\omega} \mu_1 \sin^2(\omega t) dt = \frac{\mu_1 \pi}{\omega} \quad (2)$$

Thus, the simultaneous application of the two fields imparts a net motion to the particle. In this example, the net motion is independent of $\mu_0$.

"Particle" is used herein to mean any microscopic or macroscopic thing that can be moved by scodaphoresis.

The correlation of f(t) and g(t) may be computed according to a suitable correlation function such as:

$$C_{f(t),g(t)} = \int f(t) g(t+\lambda) dt \quad (3)$$

where C is the correlation, T is a period of interest, and $\lambda$ is a constant time shift. C must have a non-zero value for some value of $\lambda$.

Ideally f(t) and g(t) have a large correlation for efficient operation of SCODA, but some SCODA motion can occur even in cases where the chosen functions f(t) and g(t) and the chosen value of $\lambda$ result in small values of C. The velocity of the particle undergoing SCODA motion must be a function of both f(t) and g(t). Further, the velocity of the particle as a result of the application of f(t) and g(t) together must not be the same as the sum of the velocities resulting from application of f(t) and g(t) independently. That is:

$$\vec{v}(f(t),g(t)) \neq \vec{v}(f(t),0) + \vec{v}(0,g(t+\lambda)) \quad (4)$$

One set of conditions which is convenient, but not necessary, for scodaphoresis is:

$$\int_{-\infty}^{\infty} f(t)dt=0, \int_{-\infty}^{\infty} g(t)dt=0,$$

$$\int_{-\infty}^{\infty} v(f(t),0)dt=0, \text{ and } \int_{-\infty}^{\infty} v(0,g(t))dt=0 \quad (5)$$

where v(f(t),0) is the velocity of a particle as a function of time when the particle is interacting only with the driving field f(t); v(0,g(t)) is the velocity of a particle as a function of time when the particle is interacting only with the mobility-varying field g(t); and, $$\int_{-\infty}^{\infty} v(f(t),g(t))dt \neq 0 \quad (6)$$

in this case, the two fields, acting independently, do not produce any net motion of the particle. However, the combined effect of the first and second fields does result in the particle being moved with a net velocity.

To optimize SCODA one can select functions f(t) and g(t) so that the first order velocity of the particles caused by either f(t) or g(t) is zero (so particles have no net drift), and so that the combination of f(t) and g(t) acts on the particles to provide a maximum velocity. One can select f(t) and g(t) and a phase shift $\lambda$ to maximize the integral:

$$\int_0^T \vec{v}(f(t),g(t+\lambda))dt \quad (7)$$

The process in this case runs from time 0 to time T or possibly for multiple periods wherein t runs from 0 to T in each period.

It is not necessary that f(t) and g(t) be represented by sinusoidal functions, by the same functions, or even by periodic functions. In some embodiments of the invention, f(t) and g(t) are different functions. In some embodiments of the invention, f(t) and g(t) are not periodic. FIGS. 1A through 1H show some examples of functions f(t) and g(t) that could be used in specific embodiments of the invention.

Figure 1B:
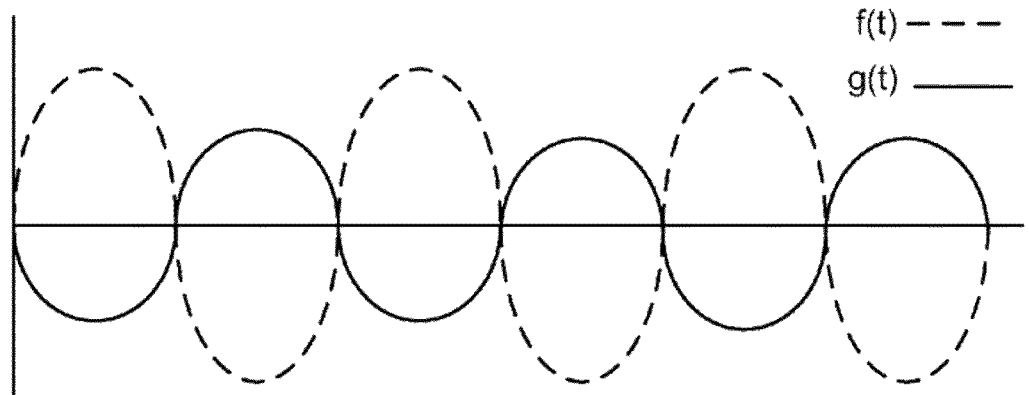

FIG. 1A shows a case wherein f(t) and g(t) are both sine functions with f(t) and g(t) in phase. FIG. 1B shows a case where f(t) and g(t) are both sine functions with f(t) and g(t) out of phase. As described below, the direction in which particles are caused to move can be reversed by altering the relative phase of f(t) and g(t).

Figure 1C:
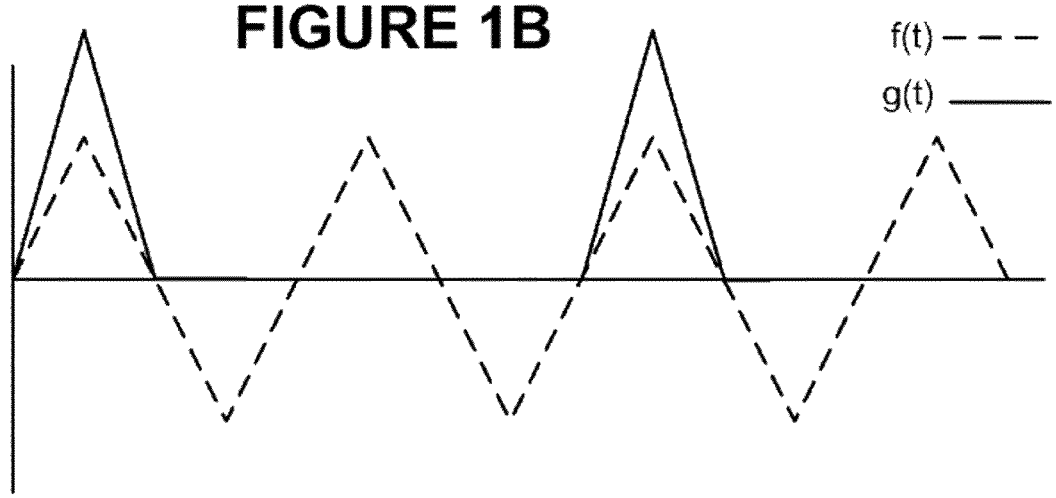
Figure 1D:
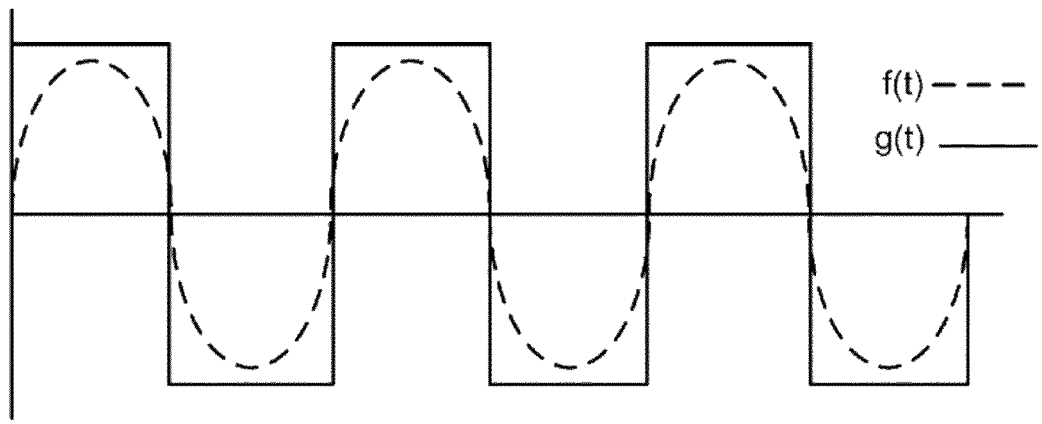
Figure 1E:
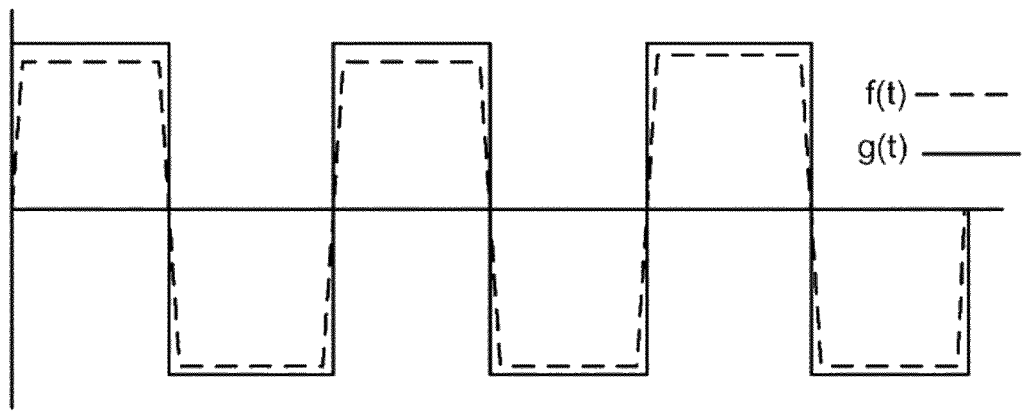
Figure 1F:
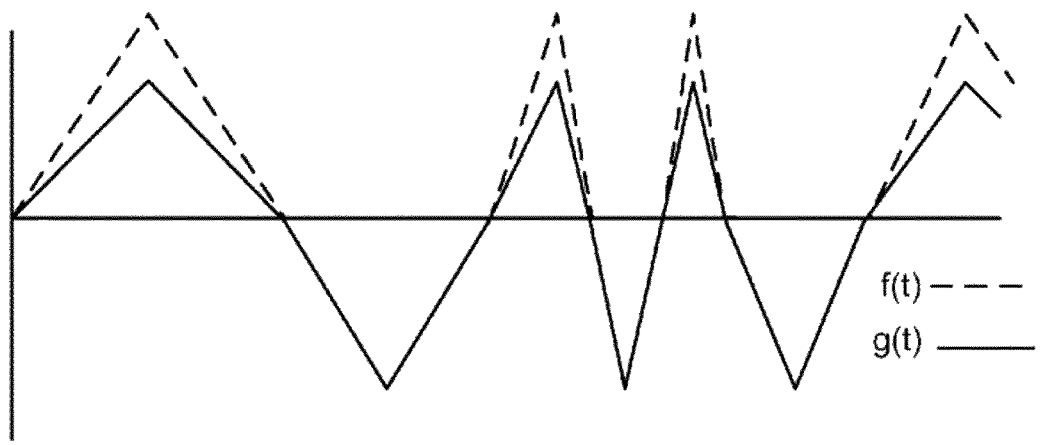
Figure 1G:
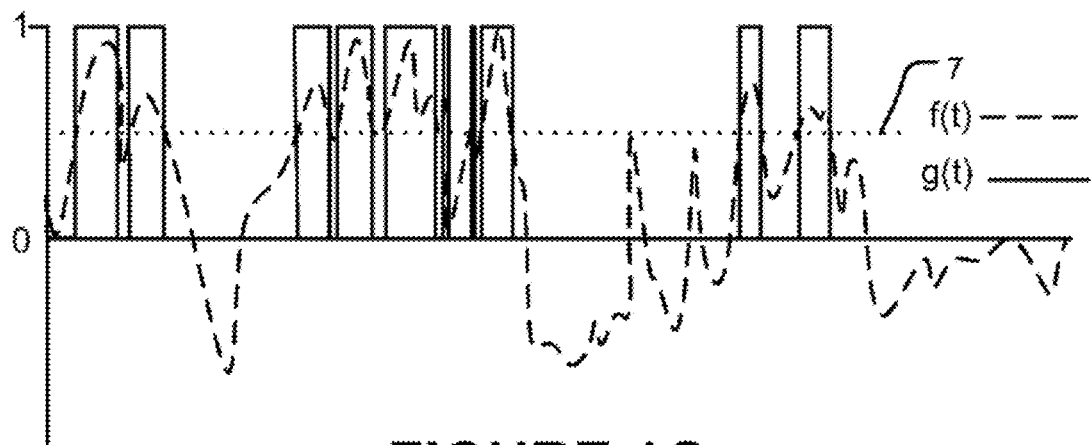
Figure 1H:
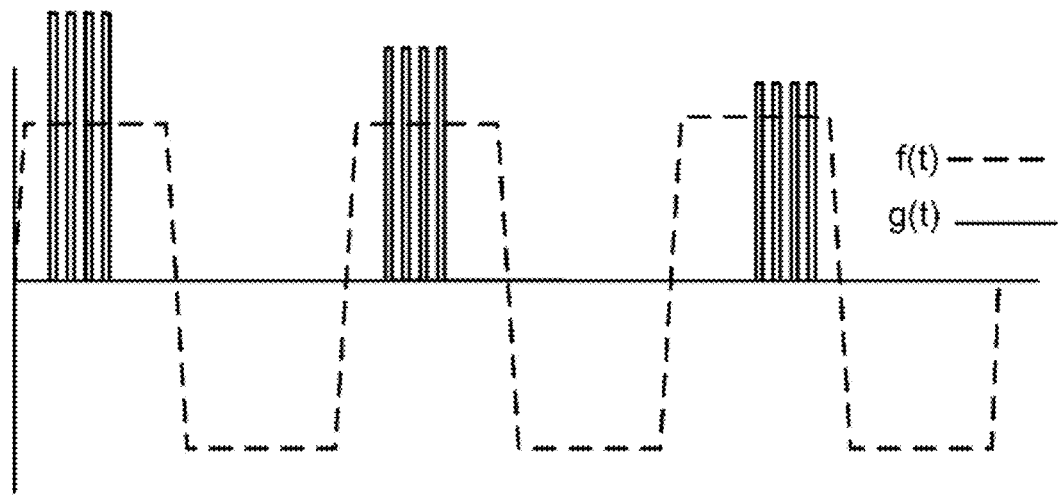

FIG. 1C shows a case where g(t) is unbalanced. In FIG. 1C, f(t) and g(t) are both triangular functions. In FIG. 1C g(t) has a frequency half of that of f(t). In FIG. 1D, f(t) has a square waveform while g(t) has a sinusoidal waveform. In FIG. 1E, f(t) and g(t) both have substantially square waveforms. In FIG. 1F, f(t) and g(t) have varying frequencies. In FIG. 1G, f(t) is essentially random noise and g(t) has a value of 1 (in arbitrary units) when f(t) exceeds a threshold 7 and has a value of 0 otherwise. In FIG. 1H, g(t) has the form of a series of short-duration impulses.

As another example, $$f(t) = \sin(\omega t), g(t) = 1 \text{ for } \frac{2n\pi}{\omega} < t < \frac{(2n+1)\pi}{\omega} \quad (8)$$

where n is any integer or set of integers (e.g. $n \in \{1, 2, 3, \ldots\}$ or $n \in \{2, 4, 6, \ldots\}$ or $n \in \{1, 4, 7, \ldots\}$. The integers n do not need to be regularly spaced apart. For example, the methods of the invention could be made to work in a case wherein the set of integers n consists of a non-periodic series. An otherwise periodic waveform f(t) or g(t) could be made aperiodic by randomly omitting troughs (or peaks) of the waveform, for example.

Figure 1I:
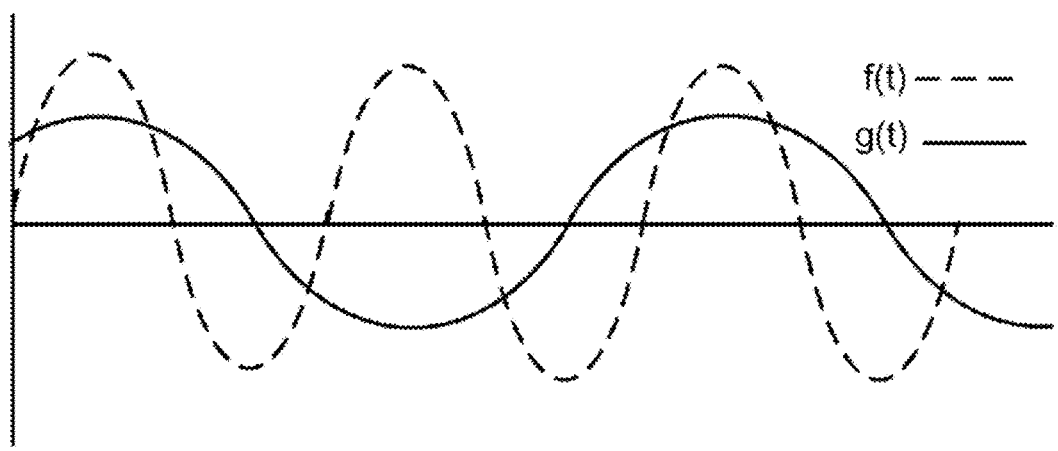

FIG. 1I illustrates a case where f(t) has a frequency twice that of g(t). The waveforms of FIG. 1I can produce SCODA motion, for example, where the mobility of particles varies in response to |g(t)|. It can be seen that |g(t)| has larger values for positive-going peaks of f(t) than for negative-going peaks of f(t).

While the waveforms shown in most of FIGS. 1A to 1I are symmetrical (i.e. they have the same overall form if inverted in spatial direction) this is not mandatory. f(t) could, in general, be asymmetrical.

Driving Fields f(t) is referred to herein as a driving function because it drives motion of the particles in the medium. In different embodiments of the invention, f(t) is produced by fields of different types. For example, f(t) may be produced by any of:
 a time-varying electric field;
 a time-varying magnetic field;
 a time-varying flow in the medium;
 a time-varying density gradient of some species in the medium;
 a time-varying gravitational or acceleration field (which may be obtained, for example by accelerating a medium containing particles and periodically changing an orientation of the medium relative to the direction of the gravitational or acceleration field);
 or the like.

In some embodiments, f(t) applies a force to particles that alternates in direction wherein the magnitude of the force is the same in each direction. In other embodiments, f(t) combines a component that alternates in direction and a bias component that does not alternate in direction such that the magnitude of the force applied to particles is larger in one direction than in the other. The bias component may be termed a DC component while the alternating component may be termed an AC component.

The driving field is selected to interact with the particles of interest. For example:
 Where the particles are electrically charged particles (ions for example), an electric field may be used for the driving field. Electrically neutral particles may be made responsive to an electric field by binding charged particles to the electrically neutral particles. In some cases an electrically neutral particle, such as a neutral molecule, can be carried by a charged particle, such as a charged molecule. For example, neutral proteins that interact with charged micelles may be driven by an electrical driving field through the interaction with the driving field and the micelles.

Where the particles have dielectric constants different from that of the medium, an electric field having a time-varying gradient can drive motion of the particles through the medium by dielectrophoresis.

Where the particles contain magnetic material (for example, where particles of interest can be caused to bind to small beads of a type affected by magnetic forces, for example ferromagnetic beads) a magnetic field may be used for the driving field.

Where the particles have magnetic susceptibilities different from that of the medium then a gradient in a magnetic field may be used to drive motion of the particles relative to the medium by magnetophoresis.

Where the particles have densities different from that of the medium then a gravitational or other acceleration acting on the particles may drive motion of the particles relative to the medium. An AC acceleration is provided in some embodiments by exposing the medium to an acoustic field.

The driving field may directly apply a force to the particles or may indirectly cause motion of the particles. As an example of the latter, the driving field may cause living particles (mobile bacteria for example) to move in response to their own preference for certain environments. For example, some organisms will swim toward light, chemical gradients, or magnetic fields (these phenomena are known as chemotaxis, phototaxis, and magnetotaxis respectively).

Mobility-Varying Fields

The mobility of particles may by altered according to any of a wide variety of mechanisms. For example:
 changing a temperature of the medium;
 exposing the particles to light or other radiation having an intensity and/or polarization and/or wavelength that varies in time with the driving field;
 applying an electric field to the portion of the medium through which the particles are passing;
 applying a magnetic field to the medium through which the particles are passing (the magnetic field may, for example, alter an orientation of a magnetic dipole associated with the particle and thereby affect a coefficient of drag of the particle or alter a viscosity of the medium which may comprise a suitable magneto-rheological fluid);
 applying an acoustic signal to the portion of the medium through which the particles are passing;
 causing a cyclic change in concentration of a species in the medium;
 exploiting electroosmotic effects;
 causing cyclic chemical changes in the medium;
 causing the particles to cyclically bind and unbind to other particles in or components of the medium;
 varying a hydrostatic pressure experienced by the medium;
 varying physical dimensions of the medium to cause a change in an effective drag experienced by particles in the medium;
 applying magnetic fields to the medium.

Any effect that varies the mobility of a particle in response to a driving field, such as an electrophoretic driving field, can be used.

In some embodiments of the invention, the mobility of particles is varied by exploiting non-linearities in the relationship between the velocity of a particle and the intensity of the driving field. Some embodiments apply a second driving field having a component acting perpendicular to the direction of the first driving field but a frequency half that of the first driving field. Applied by itself, such a second driving field would simply cause particles to oscillate back and forth in a direction perpendicular to the direction of the main driving field. When applied together with the main driving field, however, such a second driving field can cause particles to have higher average speeds relative to the medium for one direction of the main driving field than for the other direction of the main driving field. This results in a net drift of the particles because of the non-linear relationship between particle mobility and particle speed. In some embodiments the main driving field has a symmetrical waveform, such as a sinusoidal, triangular or square waveform.

A temperature of the medium in which the particles are situated may be altered in time with the driving field. The changing temperature may result in a change in one or more of a conformation of the particles, a viscosity of the medium, a strength of interaction between the particles and the medium, some combination of these, or the like. The result is that the mobility of the particles is altered by the change in temperature. The temperature of regions in a medium may be controlled in any suitable manner including:

directing radiation at the portion of the medium to heat that portion of the medium;

energizing heaters or coolers in thermal contact with the portion of the medium;

causing endothermic or exothermic chemical reactions to occur in the portion of the medium (or in a location that is in thermal contact with the portion of the medium); and, the like.

In some embodiments of the invention the medium comprises a material that absorbs radiation and releases the absorbed radiation energy as heat. In some embodiment, localized heating of the medium in the vicinity of the particles being moved is achieved by irradiating the particles with electromagnetic radiation having a wavelength that is absorbed by the particles themselves and released as heat. In such embodiments it can be advantageous to select a wavelength for the radiation that is not absorbed or converted to heat significantly by constituents of the medium so that heating is local to the particles.

Some examples of particles that have mobilities that vary with temperature are: proteins that can be cyclically denatured or caused to fold in different ways by cyclically changing the temperature; and DNA that can be cyclically denatured.

Exposing the area of the medium in which the particles are travelling to radiation changes one or more of: a conformation of the particles, a viscosity of the medium, a strength of interaction between the particles and the medium, some combination of these, or the like. The result is that the mobility of the particles is altered by changes in the intensity and/or polarization and/or wavelength of the applied radiation. Some examples of particles that have mobilities that can be caused to change by applying light are molecules such as azobenzene or spiro-pyrans, that can be caused to undergo reversible changes in conformation by applying light. Another example of the use of light to vary the mobilities of particles in a medium is the application of light to cause partial cross-linking of polymers in a medium containing polymers.

The intensity of an electric field applied to the medium may be varied in time with the driving field. In some media the mobility of particles of certain types varies with the applied electric field. In some media the particle velocity varies non-linearly with the applied electric field.

The mobility of particles in a medium may vary with the intensity of an acoustic field applied to the medium. In some cases, an acoustic standing waves in a solution or other medium may cause transient differences in local properties of the medium (e.g. electrical resistivity) experienced by particles in the medium thus leading to local inhomogeneity in the driving field (e.g. a driving electric field).

Where mobility of particles is controlled by altering a concentration of a species, the species having the varying concentration may, for example, be a species that binds to the particles or a species that affects binding of the particles to some other species or to a surface or other adjacent structure. The species may directly affect a viscosity of the medium.

As an example of the use of electroosmotic effects to control particle mobility, consider the case where the medium in which the particles are moving is a solution containing one or more polymers. In such solutions, an applied electric field can cause bulk fluid flow. Such a flow could be controlled to provide a perturbing stimulus to a pressure or flow induced driving force, or as a perturbation to an electrical driving force, possibly exploiting non-linearities in the onset of electroosmotic flow.

Chemical changes that are exploited to control particle mobility may, for example, induce changes in one or more of:

a conformation of the particles;

a conformation of some other species;

binding of the particles to one another or to other species or structures in the medium;

binding of species in the medium to one another;

viscosity of the medium; or the like.

The chemical changes may be induced optically, for example, by optically inducing cross-linking or by optically inducing oxidation or reduction of photoactive molecules such as ferrocene. The chemical changes may be induced by introducing chemical species into the medium. The chemical changes may include one or more of changes: that alter the pH of the medium; changes that result in changes in the concentration of one or more chemical species in the medium; or the like.

Particle mobility may be affected by applied magnetic fields according to any of a variety of mechanisms. For example:

The medium may contain small magnetic beads. The beads may be linked to polymers in a polymer matrix. By applying a magnetic field, the beads may be pulled away from a path of the particles, thereby reducing an effective viscosity of the medium experienced by the particles.

The medium could be a magneto-rheological fluid having a viscosity that varies with applied magnetic field.

A magnetic field may be used to cause medium viscosity to vary according to a two-dimensional pattern. The magnetic field could change in time in such a manner that the viscosity of the medium varies with position and varies in time in a manner that provides a synchronous perturbation to a periodic driving force. As another example, where the particles themselves are magnetic, transport and concentration of the particles could be affected by a magnetic field. The particles could be driven electrophoretically. The magnetic field could be switched on periodically to drive the particles toward a drag-inducing surface, or release them from such a surface. The magnetic field could also be used to make the particles aggregate.

Particles

The methods of the invention may be applied to particles of virtually any kind including molecules, ions, and larger particulates. Some non-limiting examples of particles which may be moved, concentrated and/or extracted through use of the methods of the invention are:

electrically charged or neutral biomacromolecules such as proteins, nucleic acids (RNA, DNA), and suitable lipids; long polymers; polypeptides;

aggregations of molecules such as micelles or other supramolecular assemblies;

any particles to which magnetic beads or electrically-charged beads can be attached;

living microorganisms; and, the like.

In particular the invention is effective at separating nucleic acids, which may be single-stranded or double stranded, and may vary in length from thousands of bases, to hundreds of bases, to tens of bases. In one instance, the invention is used to separate or enrich so called short nucleic acids, having 500 or fewer, e.g., 200 or fewer, e.g., 100 or fewer, e.g., 50 or fewer bases. Short nucleic acids are commonly the result of cellular breakdown, and may be found, for example, in cell-free samples (e.g., blood plasma, urine), formalin-fixed samples, or forensic samples.

For any particular type of particle, one can attempt to identify a suitable driving field, medium, and mobility-altering field. Since many biomacromolecules can be electrically charged, it is often suitable to use a time-varying electrical field as the driving field when applying the invention to moving and/or concentrating such particles. Further, there are well developed techniques for causing magnetic beads to bond to specific biological materials. Where it is desired to move and/or concentrate materials which can be caused to bond to magnetic beads then magnetic fields may be used as driving fields.

Media

The medium is selected to be a medium through which the particles can move and also a medium wherein the mobility of the particles can be altered by applying a suitable mobility-altering field. The medium may comprise, for example:

a gel, such as an agarose gel or a performance optimized polymer (POP) gel (available from Perkin Elmer Corporation);

a solution, aqueous or otherwise;

entangled liquid solutions of polymers;

viscous or dense solutions;

solutions of polymers designed to bind specifically to the molecules (or other particles) whose motion is to be directed;

acrylamide, linear poly-acrylamide;

micro-fabricated structures such as arrays of posts and the like, with spacing such that the particles of interest can be entangled or retarded by frequent collision or interaction with the micro-fabricated structure;

structures designed to interact with molecules by means of entropic trapping (see, e.g. Craighead et al., in *Science* 12 May 2000 Vol. 288);

high viscosity fluids such as PLURONIC™ F127 (available from BASF);

water; or the like.

The medium is chosen to have characteristics suitable for the particles being moved. Where the particles are particles of DNA then suitable polymer gels are the media currently preferred by the inventors. In some specific embodiments of the invention the particles comprise DNA and the medium comprises an agarose gel or a suitable aqueous solution. In some embodiments the aqueous solution is a bacterial growth medium mixed with a gel such as an agarose gel.

2D Scodaphoresis

In some embodiments, the particles are constrained to move on a two-dimensional (2D) surface. In some embodiments the 2D surface is planar. The 2D surface is not necessarily planar. In some embodiments, the 2D surface comprises a relatively thin layer of a medium, such as a gel. In some embodiments the medium is free-standing. The medium may be supported on a substrate. The substrate may comprise a sheet of glass or a suitable plastic such as mylar, for example. In some embodiments the 2D layer of medium is sandwiched between the surfaces of two substrates. Where the medium has an exposed surface, the surface may be in air or another gaseous atmosphere or submerged in a liquid such as a suitable buffer, an oil, or the like. In some currently preferred embodiments, the medium comprises a layer of a gel sandwiched between two layers of thicker gel. In an example embodiment, particles move in a layer of a 1% w/v agarose gel sandwiched between two layers of 3% w/v agarose gel.

In some embodiments of the invention, a 2D surface in which particles travel may be provided by a layer within a medium which has a non-uniform viscosity or a non-uniform concentration of a species that reduces (or increases) a mobility of the particles. The viscosity or concentration gradient cause particles to remain in the relatively thin layer within the medium or on a surface of the medium.

3D Scodaphoresis

SCODA may be used to concentrate particles in three dimensions. This may be achieved in various ways. In some embodiments, 2D SCODA is performed in a plane. The 2D SCODA may be performed using the electrophoretic SCODA method described below, for example, Z electrodes placed above and below the plane could apply an electric field that tends to drive any particles that begin to move out of the plane back into the plane.

3D SCODA could also be performed by providing a 6 electrode arrangement, where each electrode is placed on the surface of a body of a medium such as a gel. Defining X Y and Z axes of such a cube, 2D SCODA would then be run on the 4 electrodes in the XY plane, then the 4 electrodes in the YZ plane, then the 4 electrodes in the XZ plane, then repeating in the XY plane and so forth. This would produce a net 3D focusing effect, with a net SCODA force that is radial in three dimensions, but about ⅓ as strong as the 2D SCODA force for the same electrode voltages.

Samples

A variety of fluidic samples can be enriched using methods of the invention. Additionally, solid samples may be solubilized or suspended and then enriched. Suitable biological samples may include, but are not limited to, cultures, blood, plasma, serum, saliva, cerebral spinal fluid, pleural fluid, milk, lymph, sputum, semen, urine, stool, tears, saliva, sweat, needle aspirates, external sections of the skin, respiratory, intestinal, and genitourinary tracts, tumors, organs, cell cultures or cell culture constituents, or tissue sections. In some embodiments, the biological sample may be analyzed as is, that is, without additional preparation. In an alternate embodiment, harvest and/or isolation of materials of interest may be performed prior to analysis.

A sample may include any of the aforementioned samples regardless of their physical condition, such as, but not limited to, being frozen or stained or otherwise treated. In some embodiments, a biological sample may include compounds which are not naturally intermixed with the sample such as preservatives, anticoagulants, buffers, fixatives, nutrients, antibiotics, or the like.

In some embodiments, a biological sample may include a tissue sample, a whole cell, a cell constituent, a cytospin, or a cell smear. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines. In some embodiments, a biological sample includes tissue sections from healthy or diseased tissue samples (e.g., tissue section from colon, breast tissue, prostate, lung, etc.). A tissue section may include a single part or piece of a tissue sample, for example, a thin slice of tissue or cells cut from a tissue sample.

In some embodiments, a biological sample may be recovered from a solid support and suspended or solubilized prior to being used with methods of the invention. A solid support may include microarrays (e.g., DNA or RNA microarrays), gels, blots, glass slides, beads, swabs or ELISA plates. In some embodiments, a biological sample may be adhered to a membrane selected from nylon, nitrocellulose, and polyvinylidene difluoride. In some embodiments, the solid support may include a plastic surface selected from polystyrene, polycarbonate, and polypropylene. In some embodiments the biological sample is recovered from a formalin-fixed sample, e.g., a formalin-fixed paraffin-embedded (FFPE) sample.

A biological sample may be of prokaryotic origin or eukaryotic origin (e.g., insects, protozoa, birds, fish, reptiles). In some embodiments, the biological sample is mammalian (e.g., rat, mouse, cow, horse, pig, dog, cat, donkey, guinea pig, or rabbit). In certain embodiments, the biological sample is of primate origin (e.g., example, chimpanzee, or human). The samples may be forensic samples including, but not limited to, blood samples, saliva samples, urine samples, feces samples, microbial samples, pathogen samples, forensic biological samples, crime scene biological samples, drug/alcohol samples, chemicals (e.g., explosives), and residues.

Additional Analysis of Particles

In some instances, enriched samples produced with the methods and apparatus of the invention will be additionally analyzed or processed. For example, the resultant enriched sample may be amplified, hybridized, stored, lyophilized, or sequenced.

Where the enriched sample contains nucleic acids, the sample may be amplified using Polymerase Chain Reaction (PCR) technologies. A typical PCR reaction includes multiple amplification steps, or cycles that selectively amplify a targeted nucleic acid species. Additional references describe the PCR process, and common variations thereof, such as quantitative PCR (QPCR), real-time QPCR, reverse transcription PCR (RT-PCR) and quantitative reverse transcription PCR (QRT-PCR). PCR instruments and reagents are commercially available from suppliers such as Roche Molecular Diagnostics (Pleasanton, Calif.).

A typical PCR reaction includes three steps: a denaturing step in which a targeted nucleic acid is denatured; an annealing step in which a set of PCR primers (forward and backward primers) anneal to complementary DNA strands; and an elongation step in which a thermostable DNA polymerase elongates the primers. By repeating this step multiple times, a DNA fragment is amplified to produce an amplicon, corresponding to the targeted DNA sequence. Typical PCR reactions include 30 or more cycles of denaturation, annealing and elongation. In many cases, the annealing and elongation steps can be performed concurrently, in which case the cycle contains only two steps. Using PCR amplification, it is possible to amplify the targeted nucleic acid exponentially.

However, as discussed in the background of this application, PCR amplification introduces errors into the amplified nucleic acid products. In some instances, the error rate is of the same magnitude as the incidence of target nucleic acids in the sample. In these instances if PCR amplification is used, it is done after enrichment to avoid creating erroneous target nucleic acids. In some embodiments, where the PCR error rate is acceptable compared to the incidence of target nucleic acids in the sample, it is beneficial to do some PCR on the sample prior to enrichment, to boost the total number of target nucleic acids in the sample. In practice, PCR prior to enrichment is limited to fewer than 20 cycles, e.g., 15 or fewer cycles, e.g., 10 or fewer cycles, e.g., 5 or fewer cycles, in order to limit the introduction of errors. After enrichment, the enriched target nucleic acids may be amplified for further processing with 20 or more, e.g., 25 or more, e.g., 30 or more, e.g., 40 or more PCR cycles.

Several methods are available to identify target nucleic acids (e.g., variant nucleic acids, e.g., mutations) that have been enriched using methods and apparatus of the invention. In some instances an enriched sample may be analyzed with a hybridization probe. Typically, a labeled single stranded polynucleotide, which is complementary to all or part of the targeted sequence, is exposed to the sample, a wash step is performed, and then the sample is observed for the presence of the label. In some instances, amplification and hybrid probe analysis may be performed simultaneously, e.g., using quantitative PCR.

In other instances the complimentary polynucleotide probes may be immobilized on a solid support. In this instance, hybrid probe analysis typically includes (1) labeling nucleic acids in the enriched sample, (2) pre-hybridization treatment to increase accessibility of support-bound probes and to reduce nonspecific binding; (3) hybridization of the labeled nucleic acids to the surface-bound polynucleotides, typically under high stringency conditions; (4) post-hybridization washes to remove nucleic acid fragments not bound to the solid support polynucleotides; and (5) detection of the hybridized, labeled nucleic acids. Detection may be done, for example by fluorescence detection, however other methods may be used, depending upon the nature of the label.

In some embodiments, an enriched sample containing multiple target nucleic acids may be identified with a multiplex protocol designed to identify multiple specific mutations of interest. For example, single nucleotide polymorphisms (SNPs) among the target nucleic acids may be determined with a single base extension kit, such as SNAPSHOT™ available from Applied Biosystems (Life Technologies, Carlsbad, Calif.). Using this kit, the enriched sample will be mixed with a set of primers of varying length and sequence, each primer being complimentary to different loci on the target nucleic acids. Upon mixing, the primers will hybridize with a specific target nucleic acid, forming a duplex with a 3' terminus adjacent to the SNP. In the presence of a polymerase, a single fluorescently-labeled base is added to the duplex and the resulting populations of fluorescently-labeled moieties can be characterized by length and label color (e.g., using Sanger sequencings, for example GENESCAN™ analysis, Applied Biosystems) to determine the presence and amount of the mutations.

Another method that can be used to identify nucleic acids in the enriched sample is genetic sequencing. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454™ sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD™ sequencing.

In preferred embodiments, nucleic acids enriched with methods of the invention may be sequenced using next-generation sequencing. For example, 454™ sequencing, available from Roche (Branford, Conn.), may be used to quickly and accurately sequence enriched nucleic acid samples. (See Margulies, M et al. 2005, Nature, 437, 376-380, incorporated herein by reference in its entirety.) 454™ sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are then attached to DNA capture beads, e.g., streptavidin-coated beads using, e.g., Adaptor B, which contains 5'-biotin tag. The fragments attached to the beads are PCR amplified within droplets of an oil-water emulsion to make multiple copies of DNA fragments on each bead. In the second step, the beads are captured in picoliter wells. Finally, pyrosequencing is performed on each DNA fragment in parallel. As nucleotides are added, a light signal is generated and recorded by a CCD camera in the instrument. The signal strength is proportional to the number of nucleotides incorporated. The signals are then analyzed and correlated to determine the sequence.

Alternatively, ION TORRENT™ sequencing systems, available from Life Technologies (Carlsbad, Calif.) may be used to directly obtain the sequences of the enriched nucleic acids. Among other references, the methods and devices of ION TORRENT™ sequencing are disclosed in U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In ION TORRENT™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are then attached to a surface at a concentration such that the fragments are individually resolvable. Addition of one or more nucleotides releases a proton ($H^+$), which is detected and recorded in a sequencing instrument. The signal strength is proportional to the number of nucleotides incorporated. The signals are then analyzed and correlated to determine the sequence.

Another example of a next-generation sequencing technology that can be used to sequence enriched nucleic acids is ILLUMINA™ sequencing, available from Illumina, Inc, (San Diego, Calif.). ILLUMINA™ sequencing amplifies DNA on a solid surface using fold-back PCR and anchored primers. The DNA is then fragmented, and adapters are added to the 5' and 3' ends of the fragments. Next, fragments are attached to the surface of flow cell channels, and the DNA is extended and bridge amplified. This process results in several million clusters of approximately 1,000 copies of single-stranded DNA molecules of the same template in each channel of the flow cell. Using primers, DNA polymerase, and four fluorophore-labeled, reversibly-terminating nucleotides, the copies are then sequentially sequenced and fluorescence-imaged to determine the added nucleotide. The 3' terminators and fluorophores from each incorporated base are subsequently removed, and the incorporation, detection and identification steps are repeated to read out the next nucleotide.

In some instances, the enriched nucleic acids will be identified using mass spectrometry. Mass spectrometry uses a combination of electric and/or magnetic fields to cause nucleic acid ions (or pieces of) to follow specific trajectories (or to have specific flight times) depending on their individual mass (m) and charge (z). In addition, by arranging collisions of a parent molecular ion with other particles (e.g. argon atoms), the molecular ion may be fragmented forming secondary ions by the so-called collision induced dissociation (CID). The fragmentation pattern/pathway very often allows the derivation of detailed structural information. The structural information may be used to determine the sequence of the nucleic acid. Nucleic acids are difficult to volatilize, however. Using techniques such as electrospray/ionspray (ES) and matrix-assisted laser desorption/ionization (MALDI), nucleic acids can be volatilized, ionized, and characterized by their mass-to-charge profile. Additionally, DNA massarrays, such as offered by Sequenom (San Diego, Calif.), can be used to facilitate MALDI mass spectrometric analysis by tagging complimentary nucleic acids with easily-detected mass labels.

Control Systems

Any suitable control mechanism may be used to cause a driving field and a mobility-varying field to be applied in a coordinated manner to cause particles to move by SCODA. In some embodiments of the invention, the time-variation of the driving field and the mobility-varying field are derived directly from a common source such that their effects on the particles are correlated. In other embodiments of the invention the driving and mobility-varying fields are generated under the control of a controller such as a hard-wired controller, a programmable controller, a general purpose computer equipped with suitable interface electronics or the like. Any suitable control mechanism including those known to those skilled in the art of designing scientific equipment may be applied.

EXAMPLES

The following examples illustrate various specific embodiments of the invention. These embodiments of the invention are considered to be individually inventive. Some of these examples summarize experiments that have been performed and others are prophetic examples.

Example 1

Electrophoretic Concentration of Particles by SCODA

Consider an electrically charged particle that has an electrophoretic mobility, $\mu$ in an electric field given by $\vec{E} = \cos(\omega t) E \hat{E}$ where $\hat{E}$ is a unit vector. By definition, the particle will move with a velocity given by:

$$\vec{v} = \mu \cos(\omega t) E_0 \vec{E} \qquad (9)$$

From Equation (9), $\vec{v}$ has a time average of zero. If $\mu$ varies as a function of time and the Fourier transform of $\mu$ has a component proportional to $\cos(\omega t)$ then the time average of v(t) may not be zero. As a simple example, consider the case where:

$$\mu(t) = \mu_0 + \mu_1 \cos(\omega t) \qquad (10)$$

In this case, the time average of v(t) is:

$$\vec{v} = \frac{1}{2} \mu_1 E_0 \hat{E} \qquad (11)$$

This demonstrates the basic principle that there can be a non-zero electrophoretic drift even if the time average of the applied electric field is zero.

Now consider the case where the mobility of a particle is a function of electric field strength. While virtually any nonlinearity can be employed, consider the case where a particle's velocity is parallel to the direction of a driving electric field and the particle's speed is given by:

$$v = kE^2 \qquad (12)$$

where k is a constant and E is the magnitude of the electric field. In this case, the particle's speed is proportional to the square of the magnitude of the electric field. The effective mobility of the particle (i.e. the relationship between small changes in drift velocity, $d\vec{v}$, and small changes in the electric field, $d\vec{E}$) varies with the magnitude of the applied electric field.

In Cartesian coordinates:

$$dv_x = \frac{\partial v_x}{\partial E_x} dE_x + \frac{\partial v_x}{\partial E_y} dE_y \qquad (13)$$

and $$dv_y = \frac{\partial v_y}{\partial E_x} dE_x + \frac{\partial v_y}{\partial E_y} dE_y$$

Where the particle speed varies with the electric field as in Equation (12), Equation (13) reduces to:

$$dv_x = k\left[\left(E + \frac{E_x^2}{E}\right) dE_x + \left(\frac{E_x E_y}{E}\right) dE_y\right], \qquad (14)$$

and $$dv_y = k\left[\left(\frac{E_x E_y}{E}\right) dE_x + \left(E + \frac{E_y^2}{E}\right) dE_y\right] \qquad (15)$$

To help interpret this, consider the case where $E_y=0$ such that $E_x=E$. In this case Equations (14) and (15) become:

$$dv_x = 2kE \, dE_x \text{ and } dv_y = kE \, dE_y \qquad (16)$$

From Equation (16) one can see that the influence on the particle velocity of perturbations of the electric field has a magnitude proportional to that of the ambient field. A perturbation having the same direction as the electric field has twice the influence on the particle velocity as a perturbation perpendicular to the electric field.

This can be exploited to provide an applied electric field that causes particles to be concentrated. Consider a plane wherein an applied electric field has a constant magnitude, E, and the electric field rotates in direction at an angular frequency w so that the components of the electric field in x and y directions are given by:

$$E_x = E \cos(\omega t) \text{ and } E_y = E \sin(\omega t) \qquad (17)$$

Substituting the values from Equation (17) into Equations (14) and (15) yields a result which is the sum of constant terms, sine and cosine terms having an angular frequency $\omega$, and sine and cosine terms having an angular frequency $2\omega$. A frame of reference can be selected such that only the cosine terms having an angular frequency of $2\omega$ contribute to net particle drift. Evaluating only these terms yields:

$$dv_x = \frac{kE}{2}[\cos(2\omega t)] dE_x, \qquad (18)$$

$$dv_y = \frac{kE}{2}[\cos(2\omega t)] dE_y$$

If a perturbing electric field having the form of a quadrupole field that varies with a frequency $2\omega$ is added to the basic electric field specified by Equation (17) then a net drift of particles can be caused. For a perturbing electric field given by:

$$dE_x = -dE_q x \cos(2\omega t) \text{ and } dE_y = dE_q y \cos(2\omega t) \qquad (19)$$

it can be shown that:

$$\overline{d\vec{v}} = \frac{kE \, dE_q}{4} \vec{r} \qquad (20)$$

Equation (20) shows that for charged particles at all positions $\vec{r}$ there is a time-averaged drift toward the origin with a speed proportional to k, the coefficient that specifies the field-dependence of the mobility, E, the strength of the rotating field, and dEq, the strength of the perturbing quadrupole field.

Figure 2:
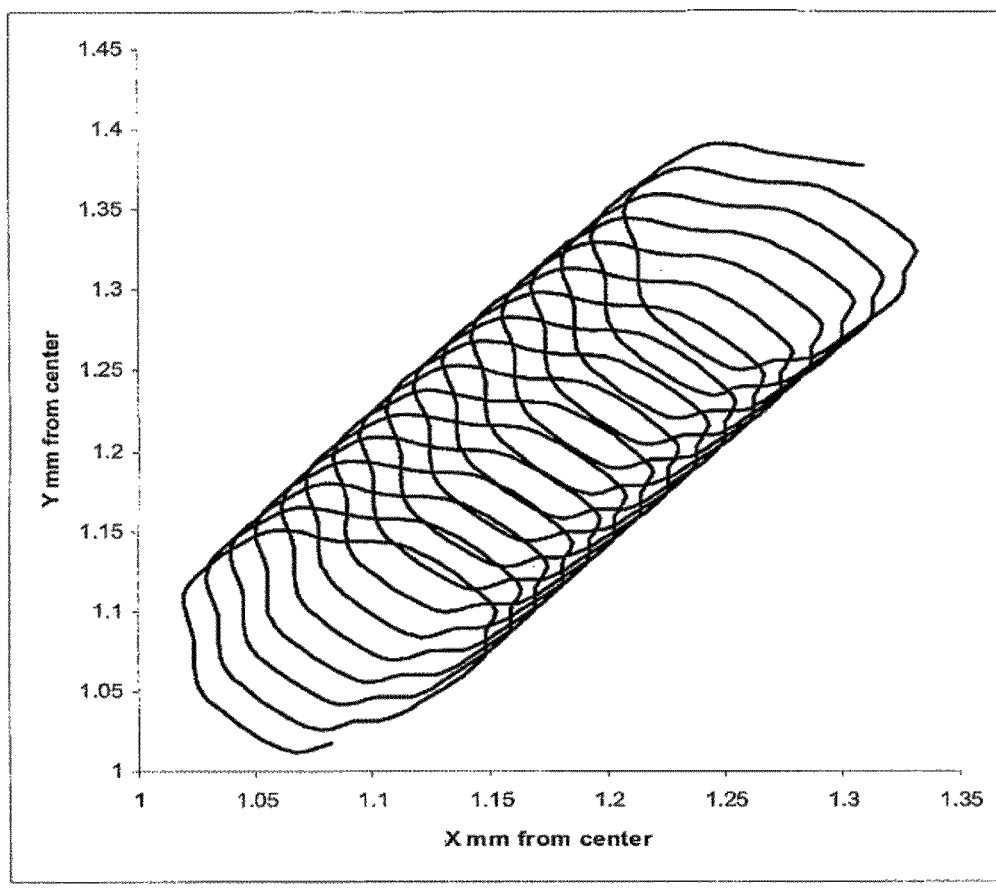
FIG. 2 is a plot showing a numerical simulation of the path of a particle.

The above calculation is for a case where the perturbing quadrupole field has a magnitude that is small in comparison to the rotating field. This is not necessary in general. FIG. 2 shows the result of a numerical simulation of the path of a particle in a case where the rotating electric field and quadrupole electric field are similar in magnitude. Motion begins at the top right hand side of FIG. 2 and progresses toward the bottom left over a period of 200 seconds. The applied electric fields are as described in Table I below. Each loop in the spiral path corresponds to a cycle of 12 voltage patterns each applied for 1 second. The uniform field amplitude is 3845 V/m at the origin (center of the electrode pattern). At the same location, the magnitude of the quadrupole component of the electric field is $4.2 \times 10^5$ V/m$^2$ or about 4200 V/m at a location 1 mm from the origin.

In many situations it is advantageous to concentrate particles in regions that are free of electrodes. Electrochemical processes at electrodes can cause damage to DNA and other sensitive materials. An electrical field that provides a particle focusing effect, as described above, can be provided without the need for electrodes at the location in which the particles become concentrated.

One can estimate the size of the spot into which particles can be concentrated from the Einstein-Smoluchowsky equation for diffusion with drift. A characteristic length scale, R, for the radius of a concentrated spot is given by:

$$R \propto \sqrt{\frac{D}{\mu_s}} \quad (21)$$

where D is the diffusion coefficient for the particles and $\mu_s$ is given by $kEE_q/4$.

Figure 3A:
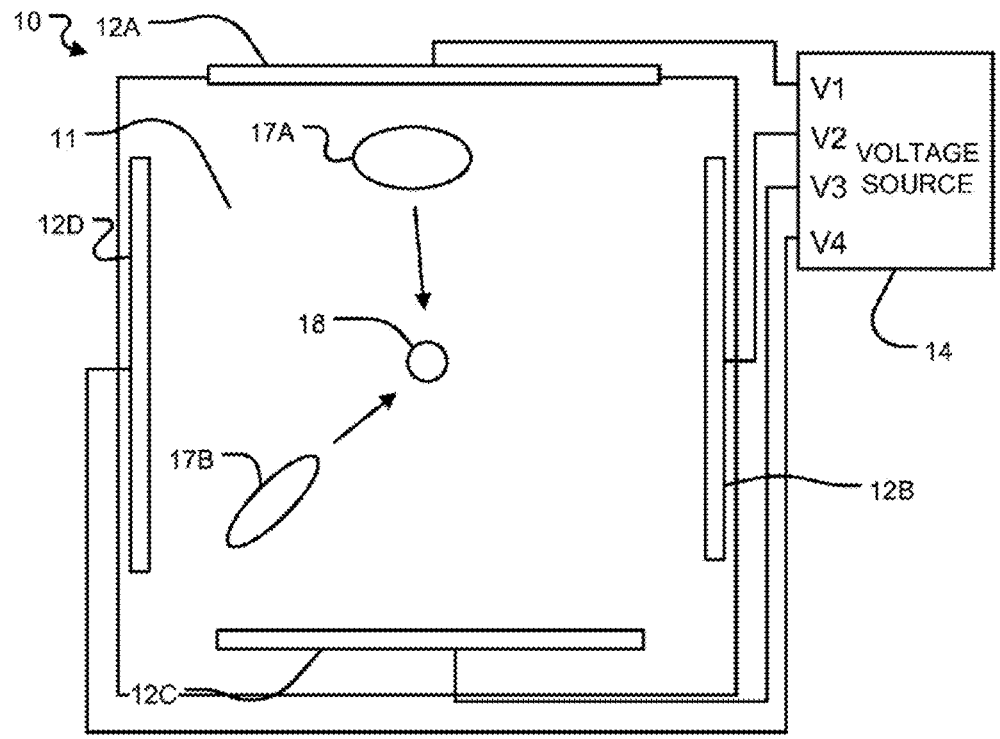
FIGS. 3A, 3B, 3C, 3D and 3E are schematic diagrams of apparatus that may be used to practice embodiments of the invention.

FIG. 3A shows apparatus 10 having a simple arrangement that can be used to practice the invention. A layer 11 of a medium, which may be a gel, such as an agarose gel, is located between four symmetrically arranged electrodes 12A, 12B, 12C, and 12D (collectively electrodes 12). It has been found to be desirable to provide electrodes 12 in the form of mesh electrodes. A power supply 14 applies individually controllable electrical potentials V1, V2, V3, and V4 to electrodes 12A through 12D respectively. Since it is the relative potentials of electrodes 12A through 12D that is significant, any one of electrodes 12A to 12D may be held at a convenient fixed voltage, such as 0 volts, while the voltages applied to the other electrodes are varied, if desired.

Figure 3B:
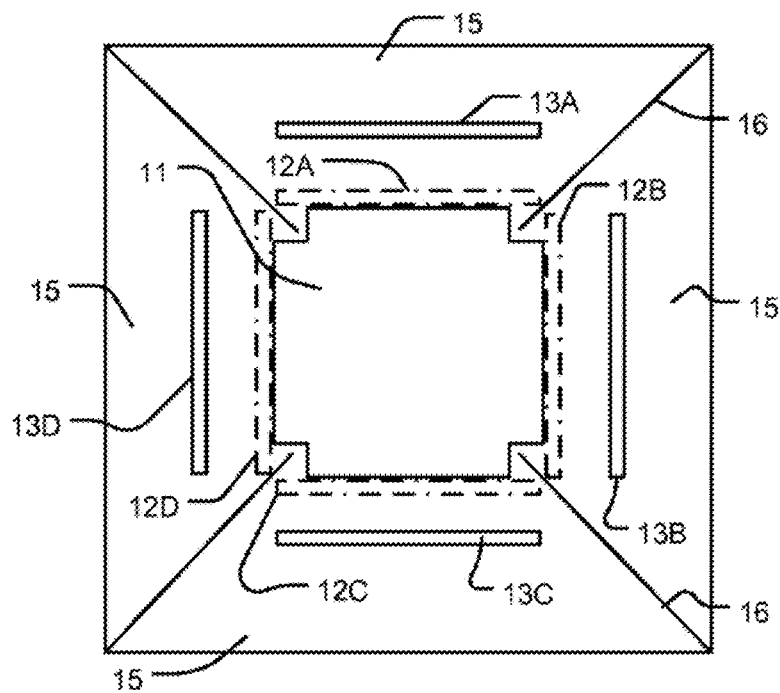

It is generally desirable to control the potentials applied to the electrodes to help stabilize the electric stimuli against small fluctuations due to changing temperature or changing power supply characteristics. Separate electrical potential sensing electrodes may be incorporated to provide feedback to a controller representing the actual electrical potential being applied. FIG. 3B is a schematic view of an apparatus comprising mesh electrodes 12A, 12B, 12C, and 12D and separate potential sensing electrodes 13A, 13B, 13C, and 13D (collectively electrodes 13). Large buffer reservoirs 15 maintain an ample supply of buffer against evaporation for long runs. Insulating barriers 16 separate adjacent reservoirs 15 electrically. Electrodes 13 are located in buffer reservoirs 15 and monitor the potential in the buffer. Feedback from electrodes 13 allows a suitably configured controller 14 to automatically adjust the voltages on mesh electrodes 12 to compensate for varying voltage drops across the mesh electrodes/buffer interface.

The magnitude of the applied voltage is chosen to match the size of the apparatus and the particles being separated. For DNA separations in agarose gels electric driving fields of approximately 50V/cm have been found to give satisfactory performance. The current supplied will depend upon the electrical conductivity and dimensions of the medium.

The application of the potentials causes electrically charged particles in medium 11 to move toward a central region 18. FIG. 3A shows groups 17A and 17B of particles moving toward concentration region 18. As noted above, the precise waveform according to which the applied electric fields vary is not critical to the operation of the invention. In a prototype embodiment of the invention, the potential variation of Equations (16) and (18) was approximated by a series of patterns of discrete voltages applied to electrodes 12A through 12D. In the prototype, each cycle was made up of 12 patterns that were each applied for 1 second before moving to the next pattern. Table 1 shows the voltages applied for each pattern.

TABLE 1

Applied voltages for scadophoresis apparatus of FIG. 3A.

| Pattern | Voltage Patterns | | | |
|---|---|---|---|---|
| | Electrode 12A (V) | Electrode 12B (V) | Electrode 12C (V) | Electrode 12D (V) |
| 1 | 0 | −66 | 0 | −198 |
| 2 | 132 | 132 | 0 | 0 |
| 3 | 132 | 198 | 0 | 198 |
| 4 | 132 | 198 | 0 | 198 |
| 5 | 132 | 0 | 0 | 132 |
| 6 | 0 | −198 | 0 | −66 |
| 7 | 0 | −198 | 0 | −66 |
| 8 | −132 | −132 | 0 | 0 |
| 9 | −132 | 66 | 0 | 66 |
| 10 | −132 | 66 | 0 | 66 |
| 11 | −132 | 0 | 0 | −132 |
| 12 | 0 | −66 | 0 | −198 |

Figure 3C:
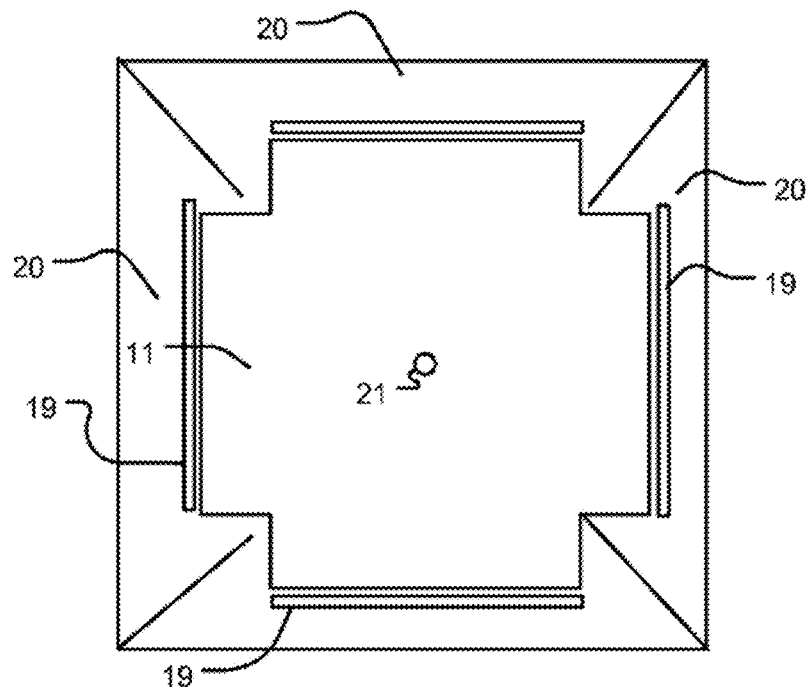

In the prototype embodiment of the invention illustrated schematically in FIG. 3C, medium 11 was in the form of a gel slab made up of 8-11 ml of 0.25% agarose gel (Agarose 2125 OmniPur available from EMD Chemicals of Gibstown N.J., USA) forming a 3.8 cm square on an acrylic base in a 0.1× Tris-acetate-EDTA buffer. Four electrodes were submerged in the gel. Each electrode extended across one third of one side of the gel boat approximately 2.5 mm up from the bottom of the gel boat. DNA was prepared by mixing 8 μl of 500 μg/ml λ phage DNA (48,502 bp, part No. N3011L available from New England Biolabs of Beverly Mass., USA) with 12 μl 0.1×TAE. 5 μl spots of the DNA were pipetted directly onto the gel after the gel had set. A thin covering of TAE was placed on the gel. The voltage patterns of Table 1 were applied to the electrodes. It was found that the DNA spots were all carried to a central area of the gel.

Figure 4A:
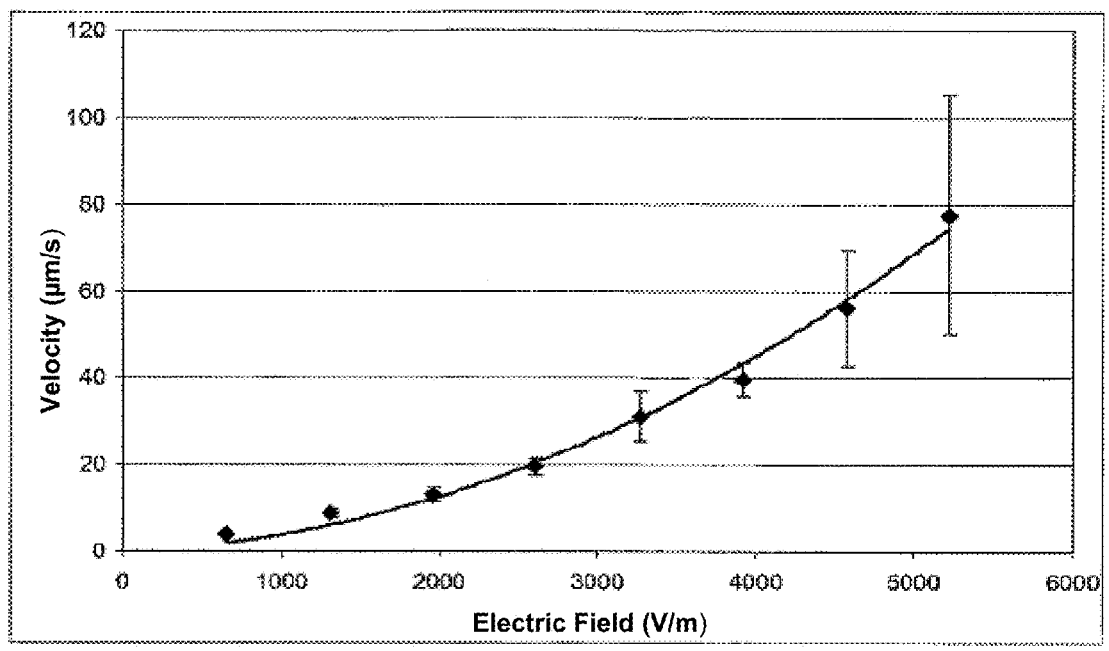
FIG. 4A is an example plot of measured DNA velocity as a function of applied electric field.
Figure 4B:
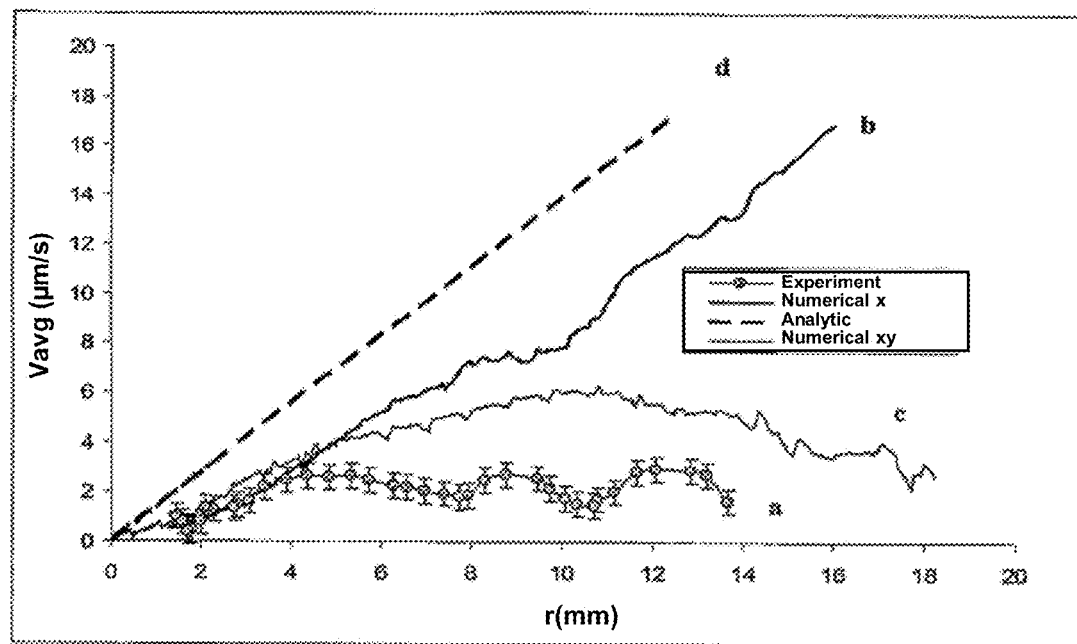
FIG. 4B is a plot illustrating time averaged particle velocity in an apparatus like that of FIG. 3A as a function of radial distance from the origin.

FIG. 4A is an example plot of measured DNA velocity as a function of applied electric field for the λ DNA used in the prototype embodiment. FIG. 4B is a plot showing time averaged drift velocity (averaged over 15 minutes) of the DNA as a function of the radial distance from the origin to which the DNA converged. FIG. 4B includes curve b which is a numerical estimate of the trajectory of a particle starting at a location on the X-axis and curve c which is a numerical estimate of the trajectory of a particle starting at a location X=Y=1.5 cm from the origin.

Figure 4C:
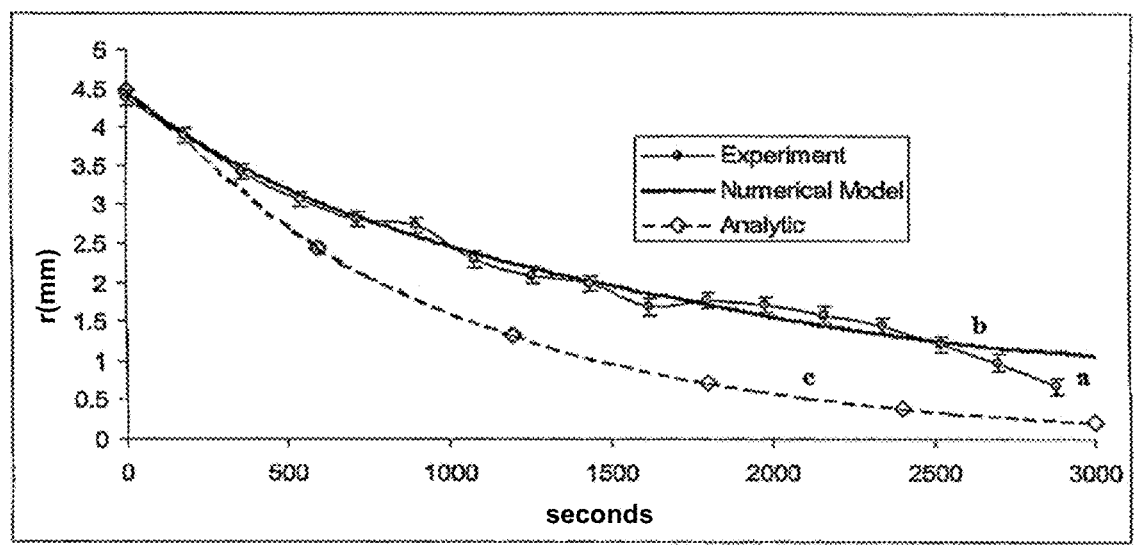
FIG. 4C is a plot showing the measured DNA spot distance from the origin as a function of time.

FIG. 4C is a plot showing the measured DNA spot distance from the origin as a function of time compared to numerical and analytical predictions. The spot position is measured over all spots visible in a given time interval. Spot trajectories for spots starting at different radial distances from the origin are shifted in time so that the start time for spots starting closer to the origin is replaced by the time at which spots starting farther from the origin reach the starting locations of the spots closer to the origin.

In the regime illustrated in FIG. 4C, there was good agreement between the calculated and observed spot trajectories.

For the DNA used in the prototype, D was measured experimentally to be $2\times10^{-12}$ m²/s. $\mu_s$ was measured to have a value of approximately $1\times10^{-3}$ l/s. Using these values, the limiting spot size was calculated to be on the order of 100 μm. Spot radii on the order of 150 to 250 μm have been achieved in experiments.

In another experiment, a homogeneous solution of 400 ng/ml λ DNA in 1% agarose gel (0.01×TAE) was subjected to scodaphoresis. The gel was prepared by mixing 3 ml of 1% agarose gel with 1.5 μl of 500 ng/μl 48,502 bp λ DNA and 1.5 μg ethidium bromide (500 ng/ml final concentration). The gel was allowed to cool to approximately 65° C. and then poured into the gel boat. The gel was arranged in a cross shape, as shown in FIG. 3C. Platinum electrodes 19 0.03 mm in diameter were located in open electrode regions 20 of the apparatus. The electrode regions were free from gel and filled with 0.01×TAE buffer.

The distance between opposing electrodes was approximately 2.4 cm. After approximately 90 minutes, the λ DNA was found to have been concentrated in a region 21 in the center of the gel boat in a spot having a full width at half maximum of about 300 µm. The concentration of the λ DNA in the spot was enhanced by a factor of approximately 3000 to 4000 as compared to the initial concentration of λ DNA in the gel boat. The ability to cause DNA to be concentrated in an area 21 which is away from electrodes is advantageous in various applications.

The concentration factor, F, that can be achieved using a square gel slab having sides of length L is calculated to be approximately:

$$F = \frac{1}{\pi}\left(\frac{L}{200}\,\mu m\right)^2 \quad (22)$$

Therefore, other factors being equal, increasing the dimensions of the gel slab can increase the concentration factor. For example, calculations suggest that a 35 cm×35 cm square gel slab could produce a concentration factor on the order of $10^6$. To achieve the best concentration it may be desirable to take steps to inhibit diffusion of particles out of the 2D surface in which SCODA is being used to concentrate the particles.

Electrophoretic SCODA in two dimensions can be performed conveniently using four electrodes arranged in two opposing pairs, as described above. Other arrangements of three or more electrodes that are not collinear with one another could also be used. For example SCODA could be performed using three electrodes arranged at corners of a triangle. SCODA could also be performed using five or more electrodes arranged around a region of a medium.

Since the passage of electrical current through a medium can lead to heating of the medium and most practical media are electrically conducting to some degree it is desirable to design SCODA apparatus to minimize heating, where practical, and to ameliorate the effects of heating, where necessary. For example, SCODA may be practiced in ways which include one or more of:

cooling the medium through the use of a cooler in physical contact with the medium, cooling a buffer circulating around the medium, blowing cool air over the medium or evaporatively cooling the medium;

making the medium very thin, thereby reducing the electrical current flowing in the medium and improving dissipation of heat from the medium;

placing the medium on a thermally-conductive substrate that acts as a heat sink;

reducing the electrical conductivity of the medium by way of a chemical treatment or by separating from the medium unneeded species that give rise to increased electrical conductivity;

providing a reservoir of buffer and replenishing buffer surrounding the medium as the buffer evaporates (see, for example, FIG. 3B);

providing one or more temperature sensors that monitor temperature of the medium and controlling the temperature of the medium to remain within an acceptable range by controlling the electrical current supplied to electrodes; and, using a driving field other than an electrical field.

Example 2

3D SCODA

Figure 3D:
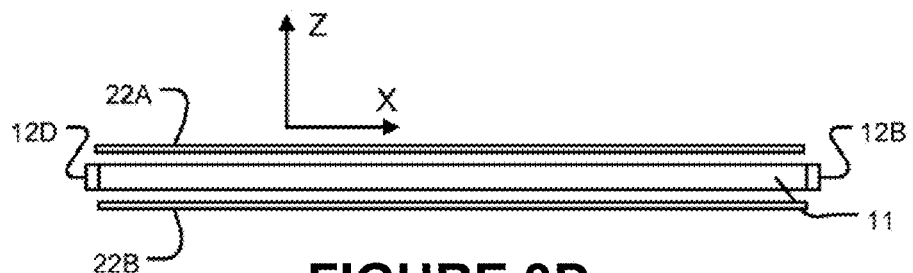

FIG. 3D shows apparatus similar to that of FIG. 3A that has been modified by the provision of additional Z electrodes 22A and 22B. Z electrodes 22A and 22B are each maintained at a DC voltage. For negatively charged particles, Z electrodes 22A and 22B are kept more negative in potential than the 2D SCODA electrodes 12A, 12B, 12C, and 12D. The provision of the Z electrodes provides a focusing force in the Z axis, and a de-focusing force in the XY plane of medium 11. The defocussing force is counteracted by SCODA.

Example 3

3D SCODA

Figure 3E:
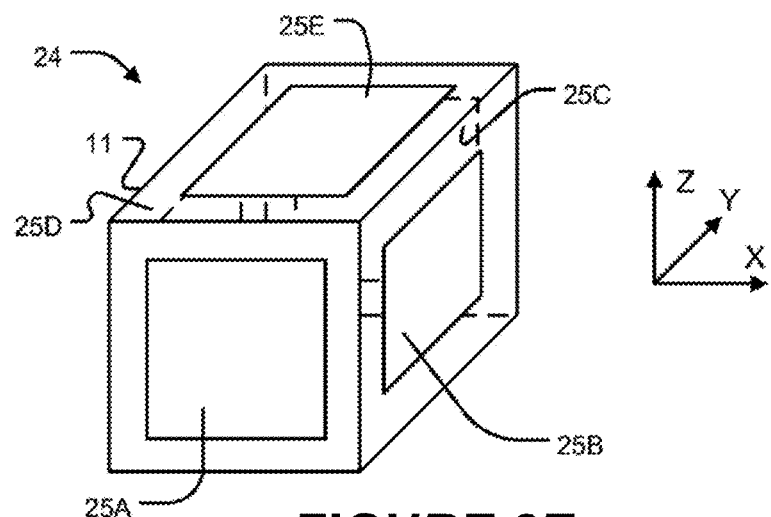

FIG. 3E shows apparatus 24 according to an embodiment of the invention that provides 3D concentration of particles in a cube-shaped block of medium 11 by alternately performing SCODA using electrodes in XY, XZ, and YZ planes. For example, electrodes 25A, 25B, 25C, and 25D are used for concentration in the XY plane. Electrodes 25A, 25E, 25C and another electrode (not visible in FIG. 3E) on the side of medium 11 opposed to electrode 25E are used for concentration in the YZ plane. Electrodes 25B, 25E, 25D and the electrode opposed to electrode 25E are used for concentration in the XZ plane.

Example 4

Size Selection by SCODA

If desired, SCODA processes can be made to select DNA and similar particles by size. This may be achieved by suitably adjusting the diffusion coefficient, D (D can be controlled by choice of medium), and the frequency of the driving field. Using higher driving field frequencies can cause larger particles to be less likely to be concentrated by SCODA. For example, in one experiment applying a driving field having a period of 12 seconds was found to concentrate both long λ DNA and shorter DNA fragments from a 1 kB ladder. It was found that reducing the period of the driving field to approximately 10 ms resulted in concentration of only the shorter DNA fragments but not the longer λ DNA fragments. While the inventors do not wish to be bound by any particular theory of operation, this size selection may be due to the 10 ms period being shorter than the relaxation time for the larger λ DNA fragments and longer than the relaxation time for the shorter DNA fragments.

In the same experiment it was found that SCODA (under these conditions) did not concentrate shorter DNA fragments (smaller than a few hundred bp). The selection out of the small sizes may be due to the smaller fragments having higher values for the diffusion coefficient D.

It is believed that SCODA provides a method for separating supercoiled plasmids from plasmids that are nicked or otherwise degraded.

Example 5

Purification of DNA

Because SCODA can be made selective for different kinds of particles by choosing a suitable medium and/or combination of driving and mobility-varying fields, SCODA can be used to purify materials, such as DNA. SCODA can be applied to cause DNA (or optionally DNA having a particular size range) to concentrate at a spot or along a line while other materials are not concentrated at the spot or line.

For example, in initial experiments, λ DNA was concentrated from a mixture of λ DNA and bovine serum albumin (BSA). There was a 10:1 concentration ratio of BSA to λ DNA. The λ DNA was concentrated into a spot, as described above. The BSA was not concentrated in the spot.

In some embodiments of the invention, denaturing agents, protease, nuclease inhibitors and/or RNAase are added to a mixture of materials from which the particles are to be separated. Such agents may be provides to facilitate one or more of:
 reducing the binding of undesired molecules to fragments of DNA or other
 molecules that are desired to be concentrated;
 reducing the amount of RNA present, if so desired;
 preventing damage to DNA; and/or
 breaking down the undesired molecules into components that will not be
 concentrated by SCODA.

In some cases it may be desirable to use SCODA to separate particles of interest from a mixture which includes materials, such as salts, that cause the medium a high electrical conductivity. For example, bacterial cell cultures are often grown in media having salt contents on the order of up to 0.4M. In cases where it is desired to use electrophoretic SCODA to separate DNA directly from a cell culture, such as an *E. coli* culture, the high electrical conductivity will result in higher electrical currents in the medium. This in turn can lead to heating of the medium. This issue may be addressed by one or some combination of the heating control techniques discussed above.

Example 6

SCODA with Selective Media

The mobility of a particle in a medium may be made dependent upon the presence in the particle of a specific DNA sequence by providing a medium with which DNA interacts by binding interactions. For example, a gel may be made to include DNA oligonucleotides that are complementary to the DNA in the particles that it is desired to concentrate. The complementary DNA oligonucleotides may be covalently bonded to the gel.

If the characteristic time required for the particles to bind to the complementary DNA oligonucleotides is $t_{on}$ and the characteristic time required for the particles to dissociate from the DNA oligonucleotides is $t_{off}$ then the average drift velocity for a particle in the medium is given by:

$$\bar{v} = \mu(E) * E \frac{t_{on}}{t_{on} + t_{off}} \quad (23)$$

where $\mu(E)$ is the field-dependent particle mobility due to reptation effects. Typically, $t_{off}$ is determined by an Arrhenius relationship while $t_{on}$ is determined by diffusive effects. By selecting particles to have lengths of 1000 or more nucleotides, reasonable values for $t_{off}$ of 1 second or less can be achieved with practical values of electric field (for example, electric fields in the range of 100 to 200 V/cm).

Figure 5:
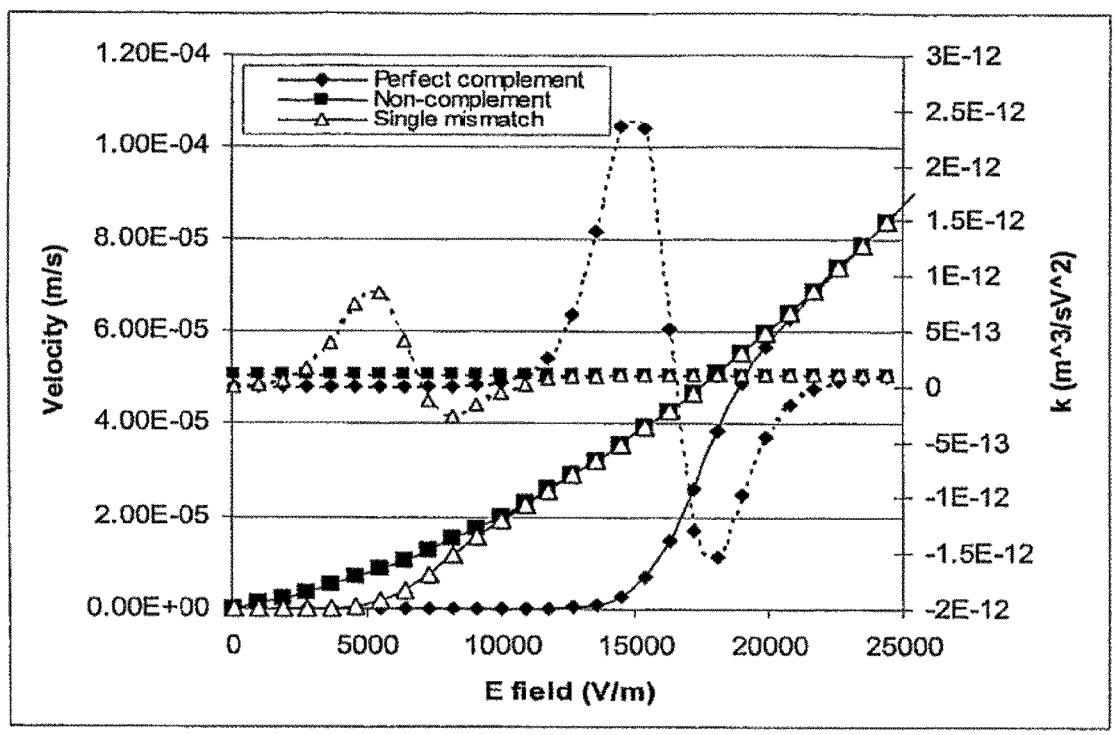
FIG. 5 shows estimated particle velocity as a function of electric field strength for three molecules in a sieving matrix comprising covalently bound oligonucleotides.

FIG. 5 shows estimated particle velocity as a function of electric field strength for three molecules in a sieving matrix comprising covalently bound oligonucleotides. A first one of the molecules is a perfect match to the covalently-bound oligonucleotides, a second one of the molecules has a single nucleotide mismatch to the covalently-bound oligonucleotides and a third one of the molecules is non-complementary to the covalently-bound oligonucleotides. DC velocity is shown in solid lines. The SCODA mobility $\mu_s$ is shown in dashed lines.

It can be seen that there are values for the electric field that result in the SCODA mobility for particles having DNA that binds to the covalently bound oligonucleotides being significantly greater than for other particles. At the electric field identified by line 7 the SCODA mobility for particles that perfectly complement the covalently bound oligonucleotides is 25 times greater than it is for non-complementary and single nucleotide mismatch molecules.

Example 7

Electric Driving Field and Thermal Mobility Varying Field

A demonstration of SCODA was carried out by thermally altering the drag coefficient of current-carrying solute ions in an electrolyte. When applying an AC potential across an electrolyte solution, and synchronously raising and lowering the temperature of the solution, a net transport of ions is expected. If the oscillation frequency of the AC potential differs from the frequency of the thermal oscillations, a detectable component of the ionic current should be present at the difference of the two frequencies, indicating alternating (AC) transport due to SCODA.

Figure 6:
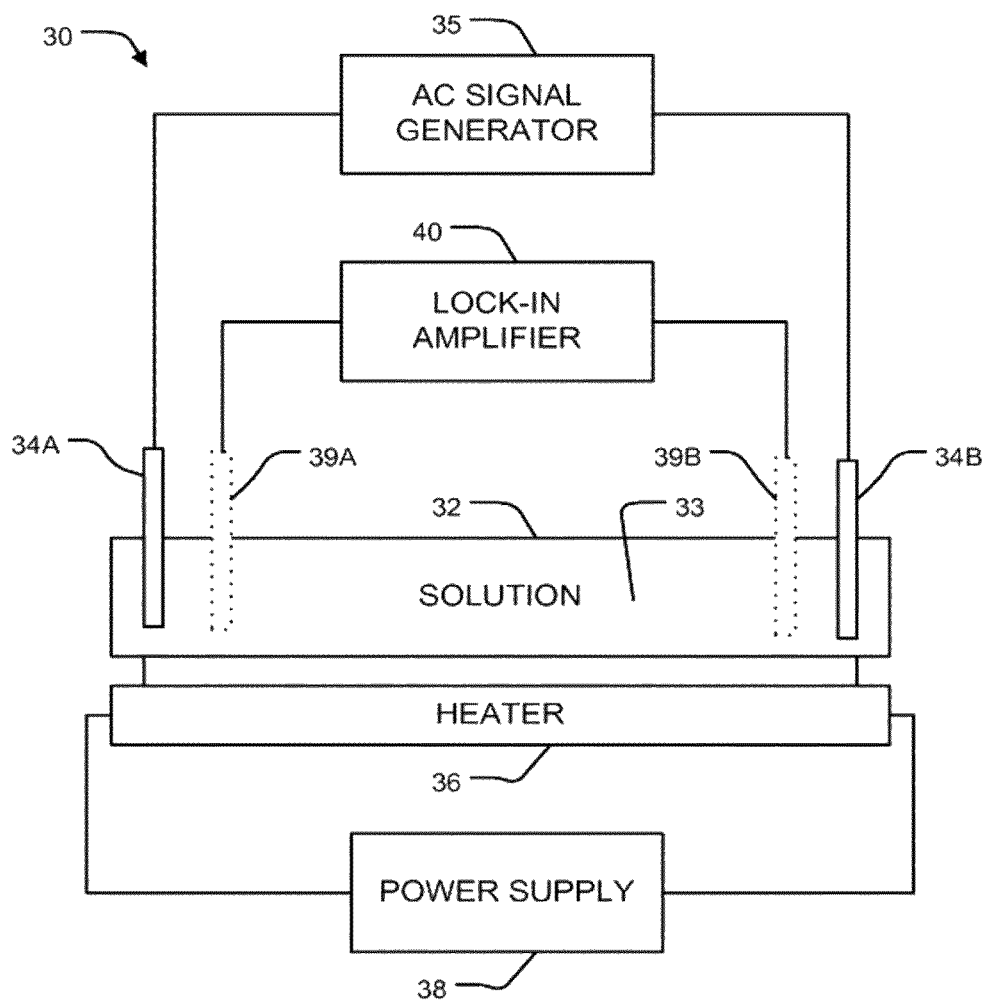
FIG. 6 is a schematic diagram of apparatus that may be used to explore scodaphoresis using an electric driving field and a thermal mobility-varying field.

FIG. 6 shows apparatus 30 that may be used to explore electric-thermal scodaphoresis. Apparatus 30 comprises a chamber 32 holding an ionic solution 33. Electrodes 34A and 34B are immersed in solution 33. A signal generator 35 applies an electrical signal of a first frequency between electrodes 34A and 34B. A heater 36 is in thermal contact with solution 33. Heater 36 is driven by a power supply 38 so that the temperature of solution 33 is made to vary at a second frequency different from the first frequency. A detector 40 such as a lock-in amplifier is connected to electrodes 39A and 39B. Detector 40 detects a signal at a frequency equal to the difference of the first and second frequencies.

In an experimental prototype apparatus, a microscope slide, cover slip and epoxy were used to construct a chamber holding 300 μL of 2.0M NaCl solution. Two gold wire electrodes were glued to the microscope slide 1 cm apart such that they were immersed the NaCl solution. One of the electrodes was grounded and the other connected through a 1 kΩ resistor to an AC amplifier. Nickel-Chromium Alloy wire (NIC60-015-125-25, Omega, Stamford, Conn.) was glued to one side of the microscope cover slip to allow heating of the solution.

During operation, 1.32 A of current was pulsed to the heater in the form of a 50% duty cycle, square wave at 10 Hz. A small fan running continuously was used to cool the microscope slide during off cycles of the heater. A 12 Hz, $3.0V_{RMS}$ sine wave was applied across the resistor and electrodes. These two signals were mixed and the output difference frequency (of 2 Hz) was fed into the reference input of a lock-in amplifier (SR830 DSP, Stanford Research Systems, Sunnyvale, Calif.). To measure the periodic current resulting from SCODA, the voltage across the 1 kΩ resistor was measured with the lock-in amplifier and the 2 Hz component was singled out for analysis. An ionic current oscillating at 2 Hz was detected.

The driven temperature oscillation of the sample solution was measured directly by a thermocouple (0.005-36, Omega) glued to the microscope slide between the electrodes. The 2 Hz component of the thermocouple output was also analyzed using the lock-in amplifier.

We assume the temperature dependent change of the electrolyte's resistance $R_0$ is small compared to both the 1 k$\Omega$ current-monitoring resistor and the DC resistance of the solution ($R_{DC}$). The voltage across the electrodes is:

$$V = V_0 \cos(\omega t), \quad (24)$$
$$V_0 = 4.23 \text{ V},$$
$$\omega_1 = \frac{2\pi}{T_1},$$
$$T_1 = \frac{1}{12} \text{ sec}$$

The resistance of the salt solution is $R = R_{DC} + R_0 \cos(\omega_2 t + \phi)$ where the frequency of the induced thermal oscillation is $\omega_2 = 2\pi/T_2$ with $T_2 = \frac{1}{10}$ s. The total current through the solution is then:

$$I_{TOT} = \frac{V_0 \cos(\omega_1 t)}{R_{DC} + R_0 \cos(\omega_2 t + \varphi)} \quad (25)$$

Assuming $R_0$ is small, Equation (24) yields an expression with a sinusoidal term at the difference frequency $(\omega_2 - \omega_1)$ whose amplitude is given by:

$$I = \frac{V_0 R_0}{2 R_{DC}^2} \quad (26)$$

A current having a magnitude of 4 µA at 2 Hz was observed.

Example 8

Electric Driving Field and Optical Mobility Varying Field

In some cases, one can alter the mobility of particles that it is desired to move by exposing the particles to radiation. In such cases one can practice scodaphoresis by controlling the application of radiation in time with the driving field such that the average mobility of the particles is different for the two directions of the driving field. For example, one could:
  apply radiation while the driving field is forcing the particles in one direction and not apply the radiation when the driving field is forcing the particles in the opposite direction;
  apply radiation of one wavelength or polarization when the driving field is forcing the particles in one direction and apply radiation of a different wavelength or polarization when the driving field is forcing the particles in the opposite direction;
  apply radiation of one intensity while the driving field is forcing the particles in one direction and apply radiation of a reduced intensity when the driving field is forcing the particles in the opposite direction;
  apply radiation having a time-varying intensity g(t) that has a non-zero correlation with the driving field;
  and so on.

In some cases it is not practical or desirable to use radiation to alter the mobility of the particles themselves but it is practical to bind to the particles other molecules that have mobilities that can be controlled by applying radiation. The other molecules may, for example, have conformations that can be changed by applying radiation or may bind to the medium in a manner that can be controlled by applying radiation.

Figure 7A:
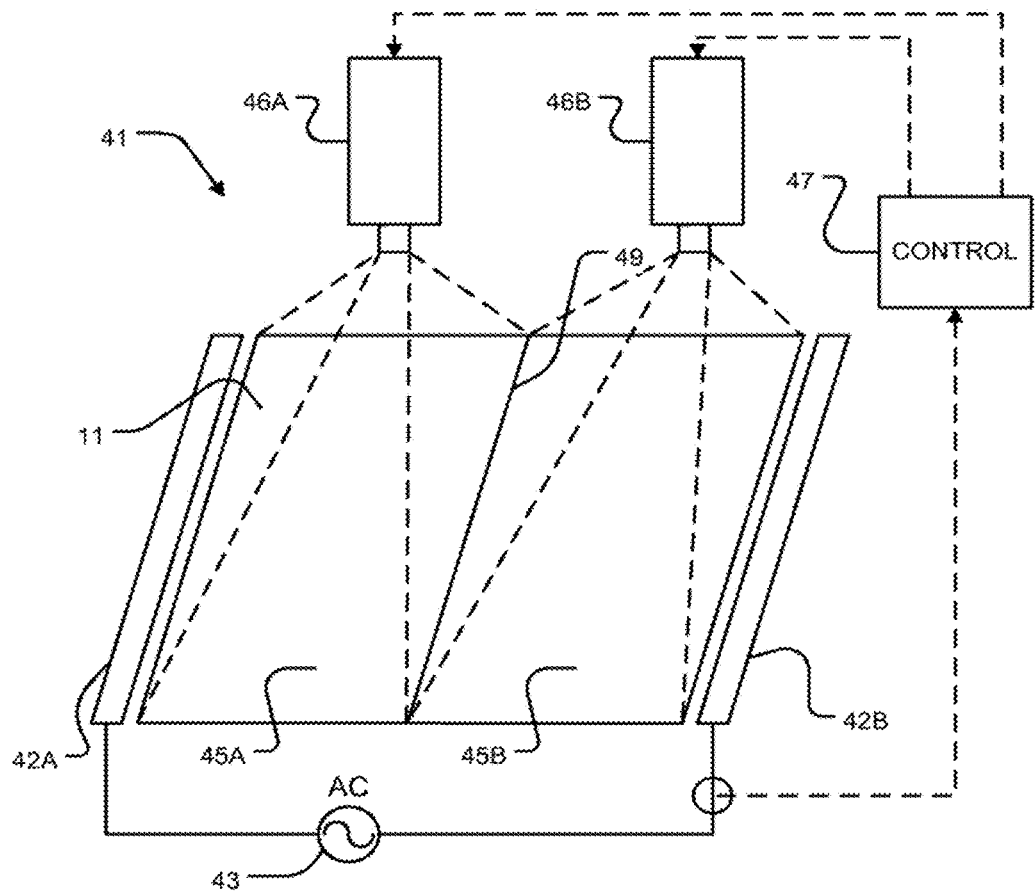
FIG. 7A is a schematic diagram of apparatus that may be used to explore scodaphoresis using an electric driving field and an optical mobility-varying field.
Figure 7B:
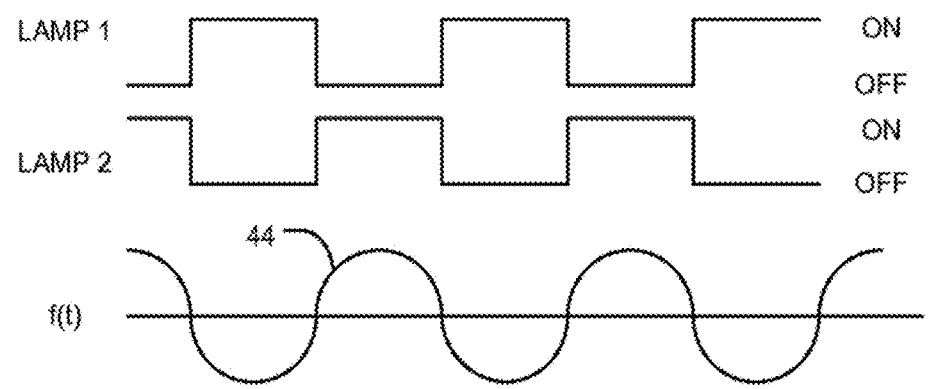
FIG. 7B shows waveforms from the apparatus of FIG. 7A.

In some embodiments, azo-benzene is attached to particles to be subjected to scodaphoresis. Azo-benzene can isomerize from the trans- to cis-form upon exposure to UV light (300-400 nm). The azo-benzene reverts to its trans-form when it is exposed to light having a wavelength greater than 400 nm. In some embodiments, spiro-pyrans are attached to the particles. Exposure of the 'closed' form of spiro-pyrans to UV light induces isomerization to yield an 'open' colored merocyanine species. The spiro-pyrans reverts to its 'closed' form on exposure to visible radiation. The transition between these two forms is accompanied by changes in the polar nature of the molecule.

Where radiation is used to vary the mobility of particles, different radiation fields may be applied in different areas to achieve concentration of the particles. For example, consider the apparatus 41 shown in FIG. 7A. In apparatus 41 a medium 11 is located between two electrodes 42A and 42B. An AC power supply 43 applies an AC electrical signal 44 (FIG. 7B) between electrodes 42A and 42B.

Light projectors 46A and 46B respectively illuminate portions 45A and 45B of medium 11. A control 47 causes light projector 46A to illuminate area 45A only when signal 44 creates an electrical field in a first direction. Control 47 causes light projector 46B to illuminate area 45B only when signal 44 creates an electrical field in a second direction opposed to the first direction. The result is that particles in medium 11 converge on line 49 at the boundary of areas 45A and 45B from both sides.

Many alternative constructions can be used to illuminate areas 45A and 45B in time with a driving field. For example:
  Light from a single lamp could be steered by a suitable optical system to illuminate areas 45A and 45B in alternation;
  Light from one or more lamps could be blocked from areas 45A and 45B in alternation by a suitable arrangement of mechanical or electromechanical filters, shutters, masks or other devices having a controllable light transmission or reflection; and,
  so on.

Focusing in the Y direction may be achieved by rotating the light pattern and electrical field by 90 degrees relative to medium 11.

Electrical/optical SCODA may be used to cause particles to congregate at an array of spots or along a number of lines. This can be achieved by applying a patterned light field to the area of medium 11. This may be used to provide samples of DNA that are concentrated along spots or lines for example. Various biological applications require an array of spots or lines of DNA.

FIGS. 8A through 8D shows a possible arrangement of four masks 50A through 50D that can be used to concentrate particles into an array of 16 spots. Masks 50A and 50B are complementary to one another. Masks 50C and 50D are complementary to one another. Mask 50A is applied while a driving field causes particles to move in a direction 51A. Mask 50B is applied when the driving field causes particles to move in direction 51B. It can be seen that particles will be concentrated along the four lines 52A, 52B, 52C, and 52D if the driving field is alternated between directions 51A and 51B while masks 50A and 50B are applied as described above. Similarly, by alternately applying mask 50C with the driving field in direction 51C and mask 50D with the driving field in direction 51D, particles will be concentrated along the four lines 53A, 53B, 53C, and 53D.

Figure 8E:
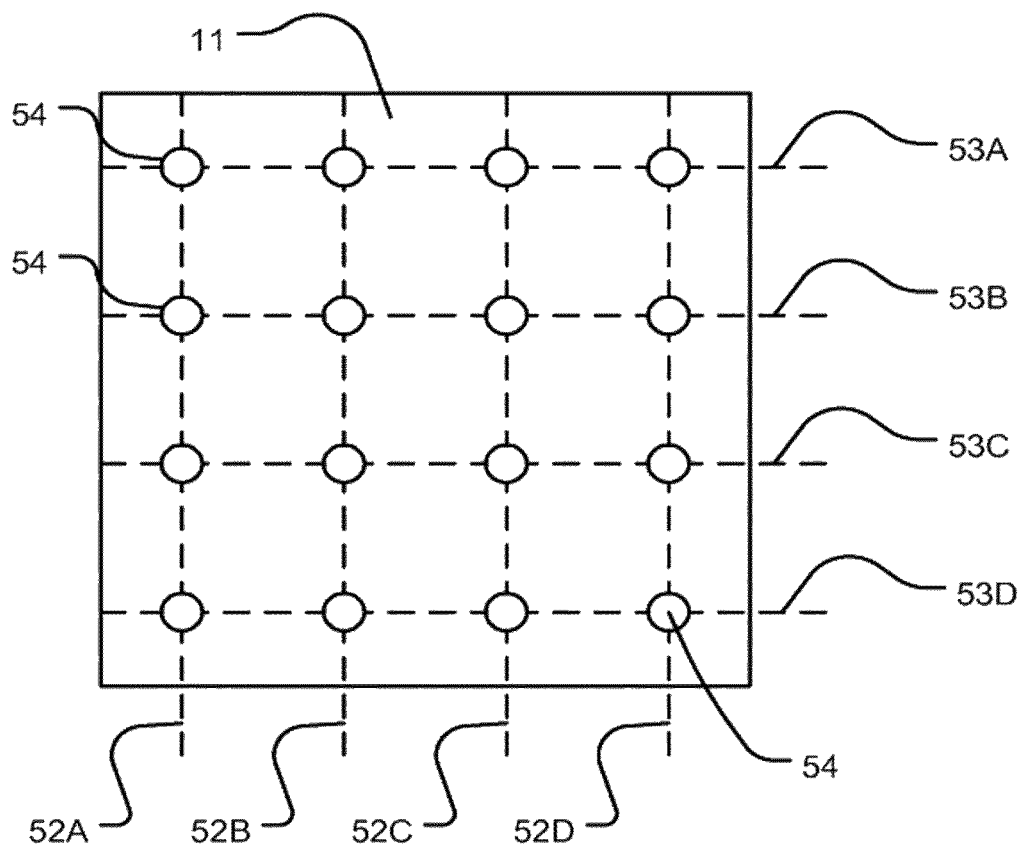
FIG. 8E shows an array of spots at which particles can be concentrated using the masks of FIGS. 8A through 8D.

Eventually, after a number of cycles, particles will be concentrated in spots 54 at the intersections of lines 52A to 52D and lines 53A to 53D as shown in FIG. 8E. The particles may comprise, for example, desired DNA or other molecules having attached azobenzene groups. The order in which masks 50A to 50D are applied (together with their corresponding driving fields) can be varied. In simple embodiments, concentration in the X direction is performed first using masks 50A and 50B and then concentration is performed in the Y direction using masks 50C and 50D.

Example 9

Optical Mobility Variation by Localized Viscosity Change

Particles to be concentrated by SCODA are located in a medium having a viscosity that varies with temperature. The mobility of the particles is dependent on the viscosity of the medium. The particles have an absorption band. Upon absorbing radiant energy having a wavelength in the absorption band, the particles release the absorbed energy as heat.

An alternating driving field of any suitable type is applied to the particles. The particles are illuminated with radiation having a wavelength in the absorption band and an intensity g(t). g(t) is selected so that g(t) has a non-zero correlation with the force f(t) applied to the particle by the driving field. When g(t) has a large value, the rate at which each particle releases thermal energy is larger than it is when g(t) has a smaller value. The thermal energy released by the particles in response to the absorbed radiation heats the surrounding media and locally alters its viscosity and thus the particle mobility.

Example 10

Fluid Flow as Driving Field

A SCODA driving field may be created by causing the medium in which the particles are situated to have a velocity that alternates in direction. For example, the medium may comprise a fluid in a pipe or capillary tube that is caused to flow back and forth in the pipe. The mobility of the particles may then be varied, either by causing the particles to interact with an externally applied field or by causing the particles to interact with a wall of the pipe in which they are located.

For example, consider a back and forth flow of a liquid in a pipe, in which molecules are suspended whose size is comparable to the pipe diameter (e.g. large DNA in a micron size capillary). Now, vary the capillary diameter (e.g. by providing the capillary with flexible walls such as walls of a silicone material and subjecting the capillary to external pressures) such that when the flow is in one direction, the molecules interact more frequently with the capillary wall and are retarded.

Example 11

Use of Cyclic Dilution/Concentration to Vary Mobility

Cyclic dilution/concentration may be used to vary the mobility of particles, especially where the particles are travelling along at or near a surface. The concentration or viscosity of the medium in which the particles are travelling may be modulated over time to correlate with the electrical or other field driving motion of the particles.

Figure 9:
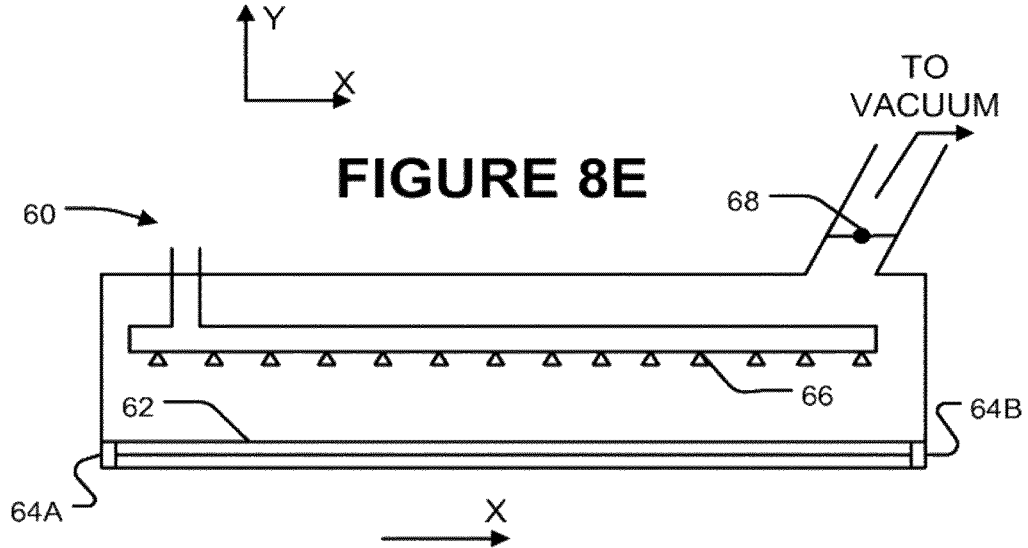
FIG. 9 is a schematic view of apparatus for producing cyclic variations in viscosity of a medium.

FIG. 9 shows apparatus 60 in which particles are travelling along a fluid layer 62. The particles are driven by an alternating electric field applied between electrodes 64A and 64B. A sprayer 66 dilutes fluid layer 62 by applying a solvent when the electric field is in a first direction. A vacuum valve 68 is opened to cause solvent from fluid layer 62 to evaporate, thereby increasing the concentration of fluid layer 62 when the electric field is in a second direction. Valve 68 and sprayer 66 are operated by a suitable control system (not shown).

Example 12

Pathogen Detection

In environmental sampling it is sometimes necessary to determine whether certain pathogens are present within relatively large volumes (e.g. 1 L or 10 L) of fluid (or solid material that can be dissolved in a fluid). Such volumes are too large for PCR to be performed in a cost effective manner in most cases. Filters can be used to concentrate DNA but such filters tend to clog. SCODA may be used to concentrate such pathogens, if present, in a sample. The sample can first be coarsely purified, then introduced into a medium in which particles of interest in the sample can be concentrated by scodaphoresis. For example, the particles may be introduced into a gel by mixing the sample with buffer and gel material to form a large volume gel. The buffer may include detergents or other agents to help lyse the pathogens and release their DNA into solution.

2D or 3D SCODA can them be performed to concentrate all or most of the DNA in the volume at a central location. The DNA at the central location is contained in a volume of gel that is manageable by normal means. The concentrated DNA may then be PCR amplified to detect specific pathogens. DNA can optionally be extracted from the gel using, for example, a commercial kit (e.g. Qiagen™) or using the I-ZIFE extraction methods described below before performing PCR amplification. In the alternative, a piece of the gel including the concentrated DNA may be subjected to PCR. The gel tends to melt during the PCR reaction does not significantly adversely affect the PCR amplification in some applications.

Example 13

Magnetic Control of Particle Mobility

Figure 10A:
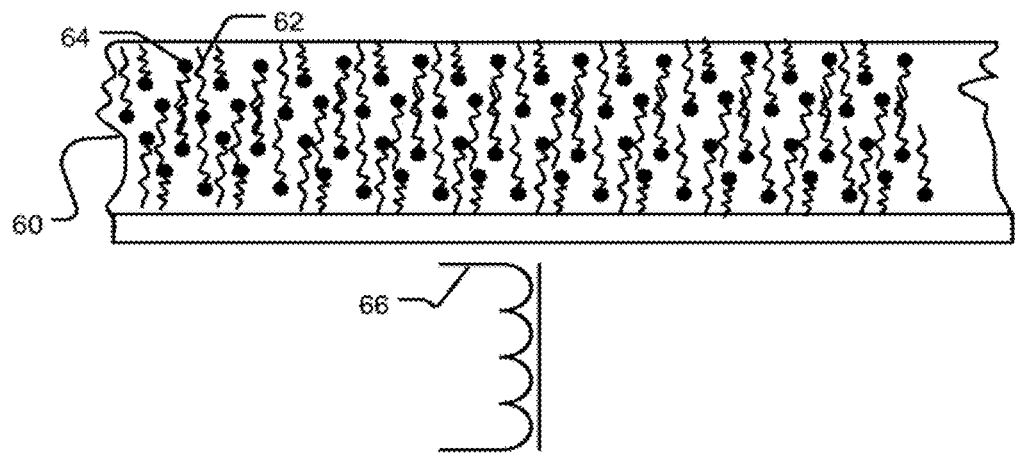
FIGS. 10A, 10B, 10C, and 10D show schematically apparatus for using magnetic fields to alter the mobility of particles.
Figure 10B:
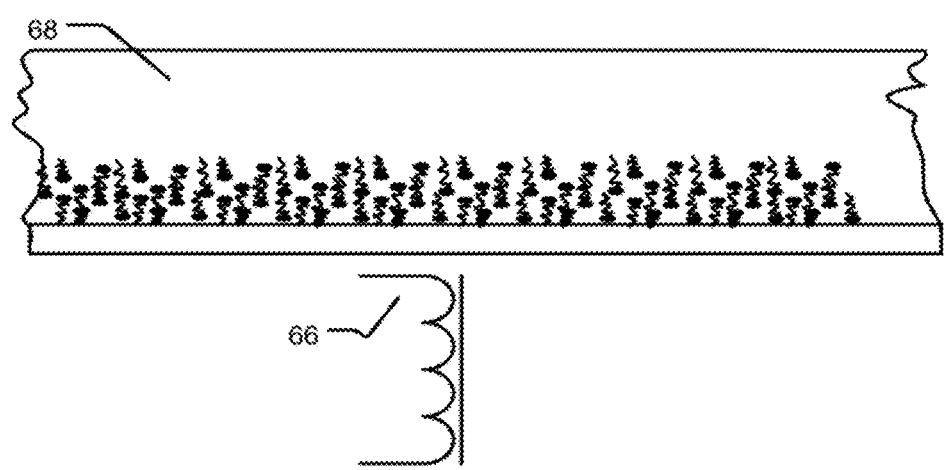

FIG. 10A shows a medium 60 comprising a polymer matrix. The medium includes polymers 62 linked to magnetic beads 64. The magnetic beads could be of the type currently available and used for DNA extractions. A magnetic field generated by a suitable magnet 66 could be turned on to pull magnetic beads 64 and the associated polymers 62 to one side of the medium as shown in FIG. 10B. the result is that a region 68 of the medium becomes less viscous. The magnetic particles could be released by switching off the magnetic field to resume the situation illustrated in FIG. 10A wherein the medium in region 68 is more viscous than it is with the magnetic field on.

The magnetic field may be patterned in two dimensions and changed over time such that the viscosity of the medium is a function of both time and position in the medium.

Figure 10C:
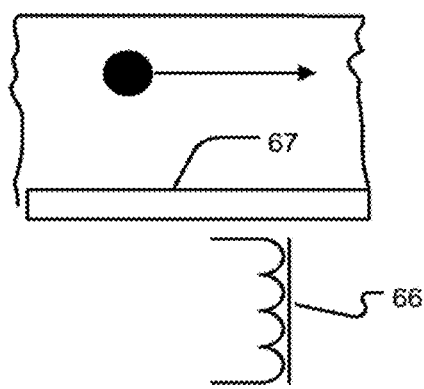
Figure 10D:
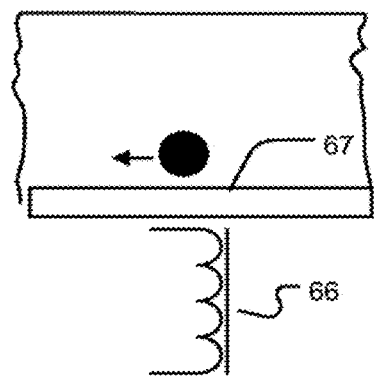

In an alternative embodiment illustrated in FIGS. 10C and 10D, the particles being transported are themselves magnetic. The driving field, may, for example, be an electrical field. A magnetic field could be switched on periodically to drive the particles toward a drag-inducing surface 67. The magnetic field could be switched off to release the particles from surface 67.

In other embodiments, the medium comprises a magneto-rheological fluid so that the medium has a viscosity that inherently varies with the applied magnetic field.

Example 14

Acceleration as a Driving Field

A gravitationally induced flow in a density gradient may be used as a driving field. consider, for example, a tube filled with a medium, such as a solution in which heavier or lighter particles are suspended. The tube is located in a centrifuge so that the particles tend to travel toward one end of the tube. The orientation of the tube is periodically reversed. A suitable mobility-varying field could be applied in time with the reversals of orientation so that the particles are caused to achieve net motion in one direction along the tube.

Example 15

SCODA for Desalination

Consider an electrically insulating capillary filled with a saline solution. If the fluid in the capillary is caused to flow then a parabolic velocity profile is established in the capillary. Fluid flows more quickly at the center of the capillary than near the capillary walls. If an electric field is established across the capillary, ions will build up preferentially within a Debye length (charge screening length) of the capillary walls as required to cancel the applied electric field. This changes the radial distribution of ions in the capillary and thus changes the average velocity of the ions. If the fluid flow is caused to reverse periodically and the electric field is applied only for one direction of flow then there will be a net transport of ions in one direction along the capillary until the SCODA induced drift is counteracted by diffusion from the accumulated ion density gradient along the capillary.

By applying a slight DC bias to the AC fluid flow in a direction opposite to the direction of ion transport, the fluid emerging from the capillary will have a reduced ion content.

Some Possible Variations to SCODA Methods and Apparatus

As described in Example 6 above, where the driving field and mobility varying field are not synchronized with one another, the result is that there is a flow of particles back and forth between two locations as the relative phases of the driving and mobility-varying fields vary. This ability to move particles back and forth between two locations at a controllable frequency may be useful in various contexts.

As will be apparent to those skilled in the art in the light of the foregoing disclosure, many alterations and modifications are possible in the practice of this invention without departing from the spirit or scope thereof. For example:

It is not necessary to generate one of the driving and mobility-varying fields. A suitable existing field, which could comprise a field already present for some other purpose or even noise could be used for one of f(t) or g(t). This existing field can be detected and a second field may be applied in time with the detected field so that the mobility of particles is altered in time with a driving field to produce a net drift.

Physically rotating electrodes at constant voltage could be used to simulate the rotating field used for 2D SCODA.

Small DC biases can be used to shift the position of focused spots. Some embodiments of the invention provide wells in the medium at locations where particles are expected to be concentrated by SCODA. The wells may be filled with a suitable buffer solution. Particles can diffuse into the wells as a result of SCODA induced concentration gradient. Particles can be extracted from the wells with a pipette or other transfer device.

Example 16

Particle Extraction Methods and Apparatus

Various methods for moving and/or concentrating particles are described above. Often, after particles have been concentrated, it is desirable to remove the particles from the medium in which they have been concentrated. For example, where DNA is concentrated in a gel, it is often desirable to extract the DNA from the gel for subsequent processing.

The following description explains methods and apparatus which may be used to extract particles from a medium. These methods and apparatus may be called "interface zero integrated field electrophoresis" ("IZIFE") methods and apparatus. IZIFE may be used to extract particles that have been moved to a location and/or concentrated by a SCODA method IZIFE also has more general application in extracting particles from media.

IZIFE exploits differences in the mobility properties of particles in different media (such as a gel medium and a buffer medium). Some charged particles (such as molecules of DNA) exhibit an electrophoretic mobility in gel solution (such as agarose gel) that depends on the magnitude of the electric field applied. Such particles can be caused to drift in one direction in such media by applying an electric field that varies asymmetrically with time. However, when those particles are in buffer or free solution, they have an electrophoretic mobility which is constant or at least has a much lower dependence on electric field strength. Therefore, the particles stop drifting if they are carried into a medium where they have a mobility that does not vary with applied field.

Application of ZIFE (zero-integrated-field-electrophoresis) to a gel containing charged particles will cause the particles to drift in the direction that yields the greater mobility. If the particles enter a region containing a buffer or free solution, they will stop drifting. Continued application of a zero time-averaged electric field causes no net drift on the particles in the buffer solution. Therefore, the particles tend to become concentrated in the buffer solution adjacent to the interface between the buffer solution and the gel.

The extraction methods detailed herein permit particles to be extracted from a medium. The invention may be applied to extracting charged biopolymers such as DNA, RNA and polypeptides from electrophoresis media, for example. Some embodiments of the invention use ZIFE to move particles from a medium, such as an electrophoresis gel, into an adjacent fluid. ZIFE is a form of Alternating Current (AC) electrophoresis where, the polarity of an applied electric field reverses periodically and the time-averaged electric field is zero. The intensity of the electric field is greater in one polarity than in the other.

Figure 11:
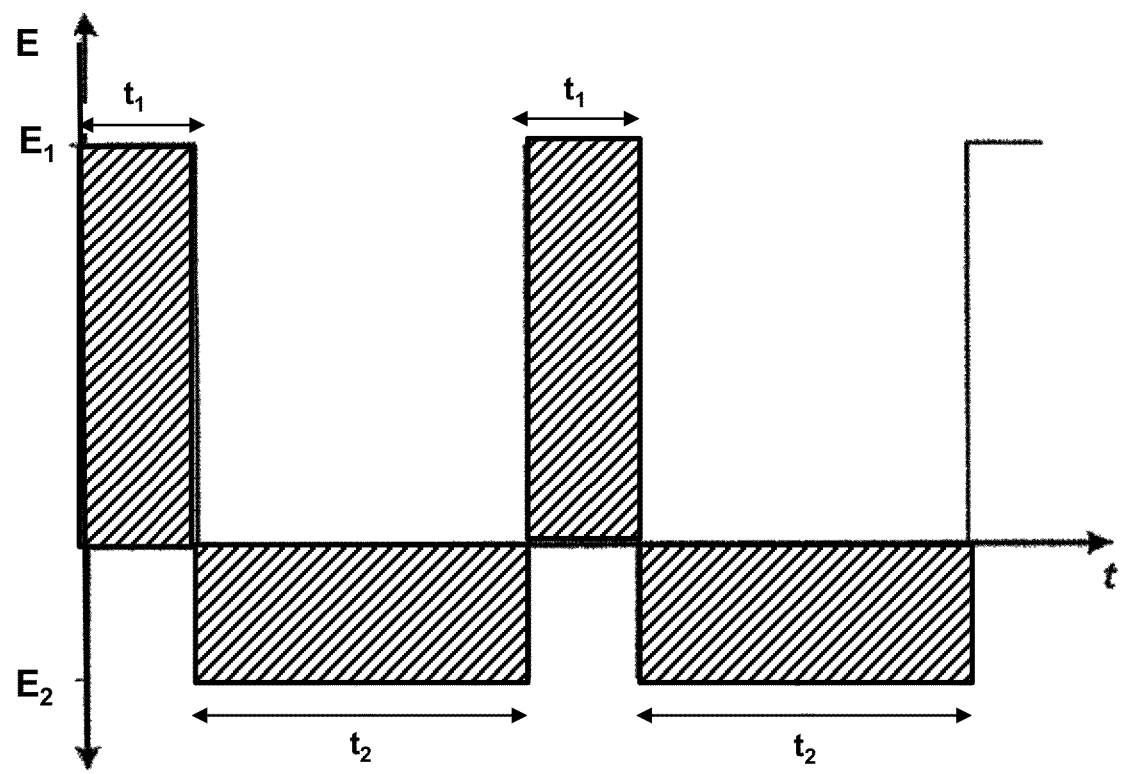
FIG. 11 is a graphical illustration of an exemplary electric field pulse used in ZIFE.

FIG. 11 is a graphical illustration of an exemplary electric field pulse used in ZIFE. As shown in FIG. 11, the pulse comprises an electric field $E_1$ applied in the positive, or "forward", direction for a time $t_1$, followed by an electric field $E_2$ applied in the negative, or "reverse", direction for a time $t_2$. If $E_2 = -E_1/r_\in$ (where $r_\in$ is the field ratio), and $t_2 = t_1 r_\in$, then the time-averaged electric field is zero. The time-averaged electric field is graphically represented by the shaded areas in FIG. 11. The "positive" shaded areas (corresponding to $E_1$) cancel the "negative" shaded areas (corresponding to $E_2$). Overall there is a zero net electric field. If the time-averaged electric field is exactly zero, then the ZIFE process is unbiased. If the time-averaged electric field deviates from zero, then the ZIFE process is biased.

As discussed above, the velocity v of a particle moving in a local electric field of amplitude E and having an electrophoretic mobility µ is given by:

$$v = \mu E \quad (27)$$

For linear systems, µ is constant. Particles having constant electrophoretic mobility have no net migration in a medium (i.e. their net velocity is zero) when ZIFE is applied to the medium. By contrast, in non-linear systems, particles have an electrophoretic mobility that is dependent on electric field amplitude. In such non-linear systems, there is a net migration of the particles in the direction that yields the greater mobility. In such a non-linear system, the particle velocity may be given by:

$$v = \mu(E)E \quad (28)$$

Suppose that charged particles in a medium have a field-dependent electrophoretic mobility of the form:

$$\mu(E) = \mu_0 + kE \quad (29)$$

It can be seen that the mobility of these particles increases with the amplitude of the electric field E. The distance d traveled by the particles under the influence of a constant electric field E is given by d=vt. If an electric field pulse of the form shown in FIG. 11 is applied, the particles will travel a greater distance during $t_1$ (while the pulse has the greater field amplitude) than the distance traveled during $t_2$. This can be shown by applying Equations (27) and (29) to the distance traveled by the particles. Hence, there is a net drift of particles in the "forward" direction, i.e. the direction in which the electric field of amplitude $E_1$ is applied.

This net drift behavior has been demonstrated by DNA molecules in agarose gels. In such gels, DNA molecules have an electrophoretic mobility of the form given by Equation (28). The field dependence of mobility arises from interactions between the DNA molecules and the gel. Therefore, ZIFE can be applied to DNA in an agarose gel to direct particles made up of DNA in a desired direction.

By contrast, application of ZIFE to DNA molecules in a buffer or free solution does not produce a net migration of DNA. This is because the mobility of DNA molecules in buffer solution is not field dependent. The differences in mobility properties of DNA in two media (e.g. a buffer and a gel) can be exploited to move particles from within one medium into another medium where the particles can be accumulated. This can be done by applying a ZIFE field across an interface between the two media.

Consider, for example, applying a ZIFE field across an interface between a gel in which there are DNA molecules and a buffer solution. Applying ZIFE to the molecules of DNA in the gel causes the molecules to migrate in the gel toward the gel-buffer interface. Once those molecules enter the buffer, the molecules will stop migrating. The ZIFE field may have a small bias in the direction which tends to move the molecules from the buffer toward the gel. This bias tends to prevent the molecules from diffusing too far away from the interface after they enter the buffer. The bias may prevent the molecules from encountering the electrode used to create the ZIFE field. The bias is small enough that the particles in the gel continue to move toward the interface (i.e. the ZIFE velocity is not overcome by the net drift resulting from the bias).

Figure 12A:
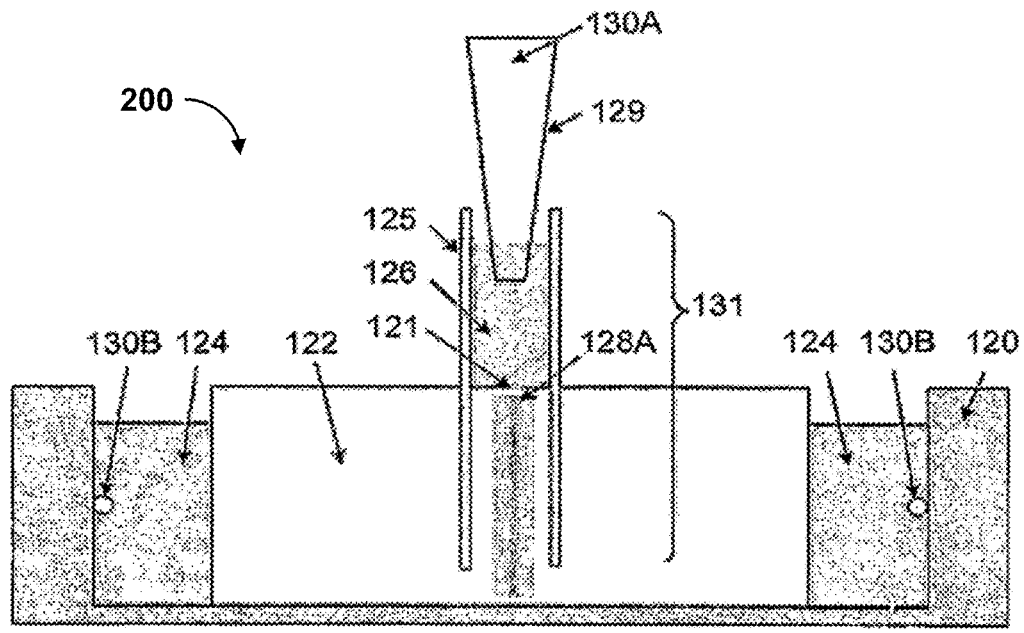
FIG. 12A is a cross-sectional elevation view of an extraction apparatus in accordance with a particular embodiment of the present invention, illustrating molecules of DNA in a solution prior to extraction.
Figure 12B:
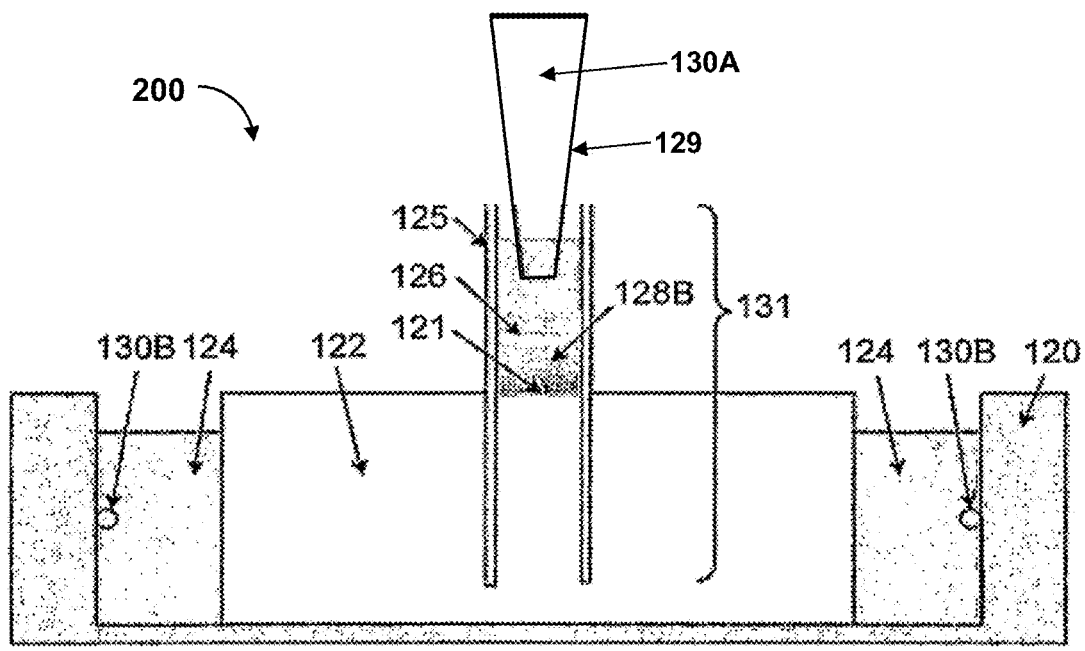
FIG. 12B is a cross-sectional elevation view of the apparatus of FIG. 12A, illustrating molecules of DNA extracted from a solution and concentrated in a small amount of buffer.

Apparatus according to one embodiment of the invention is shown in FIGS. 12A and 12B. FIG. 12A shows molecules of DNA in a gel, prior to extraction, and FIG. 12B shows molecules of DNA concentrated in a buffer, after extraction from the gel. An extraction apparatus 200 comprises a gel boat 120 (which may be shaped as a rectangular box) containing a gel 122, such as agarose gel. Gel 122 fills a substantial volume of gel boat 120. Preferably gel 122 is separated from each of electrodes 130B by a buffer solution in a reservoir 124. Reservoirs 124 are separated from one another so that the buffer does not provide short circuit paths between electrodes 130B.

As shown in FIG. 12A, prior to extraction, molecules of DNA 128A are concentrated in a column in gel 122. Molecules 128A are typically not concentrated in such form when left in their natural state. Prior to being concentrated, molecules 128A are typically distributed throughout gel 122. Molecules 128A may be concentrated into a column as shown in FIG. 12A through the use of SCODA, as described above. In the alternative, molecules 128A may be concentrated by another method. For example, the molecules to be extracted may be the molecules of a band of DNA separated by conventional DC electrophoresis or PFGE Concentration of molecules 128A in a region of gel 122 is not required prior to extraction. However, concentration is preferable to facilitate more efficient extraction of the molecules.

A capillary 125 containing a small amount of buffer solution is inserted into gel 122 so as to surround the molecules 128A to be extracted. Capillary 125 may be inserted by a robotic device which permits the location of insertion to be carefully controlled and which inserts the capillary with minimal disturbance of the gel. The robotic device may comprise a multi-axis positioner, such as an X-Y positioner, that positions capillary 125 over a desired location in a medium and then longitudinally extends the capillary into the medium. After capillary 125 is inserted into gel 122, the top portion of capillary 125 contains buffer solution, while the bottom portion of capillary 125 contains gel 122. The buffer solution in capillary 125 provides an extraction reservoir 126 adjacent to gel 122. Extraction reservoir 126 meets gel 122 at a buffer-gel boundary 121. The arrangement of buffer and gel in capillary 125 forms a buffer-gel interface 131. A pipette 129 is provided above capillary 125 to suction molecules 128A after they have migrated into extraction reservoir 126.

To provide the electric fields required for electrophoresis, an electrode 130A is located near the tip of pipette 129. Electrode 130A is preferably located sufficiently far from the interface that the extracted molecules do not encounter electrode 130A while the ZIFE field is being applied. A plurality of electrodes 130B are located in buffer reservoir 124. The electrodes may be made of platinum, for example. More electrodes may be provided than those shown in FIGS. 12A and 12B.

The tip of pipette 129 is filled with a small amount of buffer so as to provide conductivity between electrodes 130A and 130B when the pipette is inserted in capillary 125. In one embodiment, electrodes 130B are ganged to a fixed common potential (for example, electrodes 130B may be grounded), while electrode 130A is set to a different potential. A varying electric field can be applied across buffer-gel interface 131 by varying the potential of electrode 130A.

To perform Interface-ZIFE, a zero time-averaged pulsed electric field is applied across buffer-gel interface 131. The pulsed electric field may be of the form shown in FIG. 11, for example. To cause molecules 128A to migrate in the desired direction (i.e. toward extraction reservoir 126), an electric field having an amplitude $E_1$ is applied in the direction toward extraction reservoir 126, while an electric field having an amplitude $E_2$ is applied in the opposite direction. $E_1$ and $E_2$ are chosen such that the particles to be extracted have a greater mobility under the influence of $E_1$ than they do under the influence of $E_2$. For typical molecules and media $E_1 > E_2$. The polarity is selected so that the particles are driven toward interface 131 under the influence of $E_1$.

Application of Interface-ZIFE across buffer-gel interface 131 will cause molecules 128A in gel 122 to drift toward extraction reservoir 126. After some time, some of the molecules 128A will cross buffer-gel boundary 121 and enter into the buffer in extraction reservoir 126. Once these molecules reach extraction reservoir 126, Interface-ZIFE has no net drift effect on the molecules and the molecules thus stop drifting. Eventually all (or most) of molecules 128A will cross the buffer-gel boundary 121 and migrate into extraction reservoir 126. Molecules 128A become concentrated in the buffer adjacent the interface.

FIG. 12B shows molecules 128B (corresponding to molecules 128A in FIG. 12A) that have migrated from gel 122 into extraction reservoir 126. Thus, Interface-ZIFE can be used to collect and concentrate molecules 128B in extraction reservoir 126. Pipette 129 or another device can then suction molecules 128B from extraction reservoir 126, thereby completing the extraction process.

Figure 13:
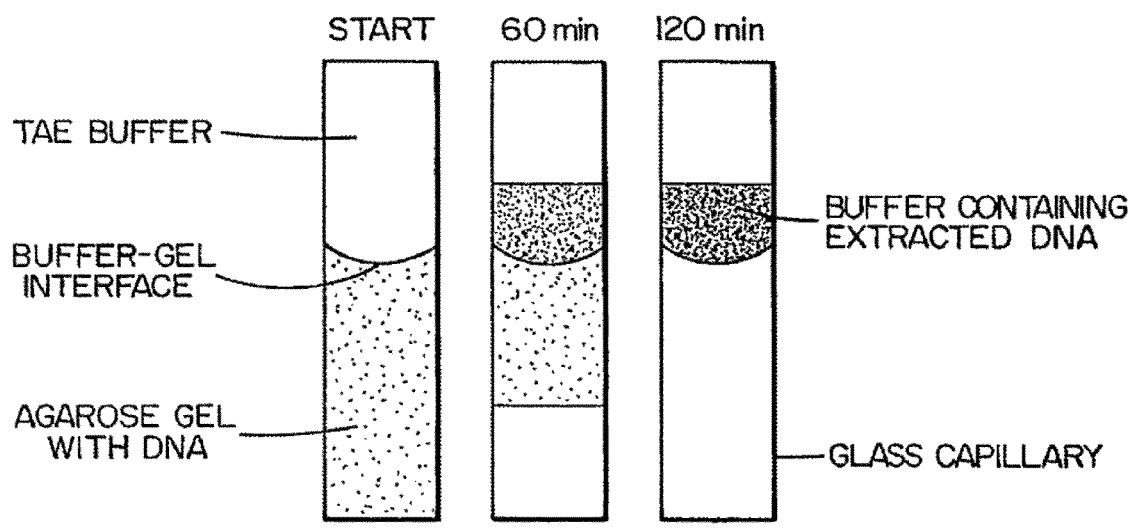
FIG. 13 shows a glass capillary in an extraction experiment using the apparatus and method in accordance with a particular embodiment of the invention.

FIG. 13 shows a glass capillary in an extraction experiment in which DNA mixed with a liquid gel was allowed to set within a capillary tube. Buffer was added to an upper portion of the capillary. The techniques described above were used to extract the DNA. An image of the capillary was captured at various times (0 minutes, 60 minutes, 120 minutes) to show the effects of Interface-ZIFE applied to a buffer-gel interface. The buffer is a TAE (Tris-Acetate-EDTA) buffer and the gel is an agarose gel containing DNA. To perform this experiment, 100 μL of liquid 1% agarose gel, mixed with 5 μL λ DNA and 2.5 μg EtBr, was pipetted into the lower portion of a 2.5 mm inner diameter glass capillary and allowed to solidify. The upper portion of the capillary was filled with approximately 50 μL of 0.1×TAE buffer and a first platinum electrode was inserted into the buffer. The bottom of the capillary was then submerged in a shallow reservoir of 0.1×TAE buffer with a second platinum electrode.

Interface-ZIFE was performed with these conditions: periodically, a voltage $V_1=200$ V was applied to the first electrode for a time $t_1=8$ s, then a voltage $V_2=-100$ V was applied to the second electrode for $t_2=16$ s. The electric field was pulsed for 2 hours. The electrodes were separated by 5 cm. Over the course of the experiment, the upper half of the capillary remained filled with buffer and the DNA remained in a relatively small volume (approximately 20 μL). As shown by the images of the capillary, there is a progressive migration of DNA through a gel and concentration of the DNA in a small amount of buffer above the gel.

If extraction reservoir 126 is sufficiently small, then molecules 128B that are concentrated in a region in extraction reservoir 126 will leave their concentrated region only by diffusion, which is slow over long distances. Convective mixing of molecules 128B and extraction buffer 126 should be minimized to maintain molecules 128B in their concentrated region. To minimize convective mixing, capillary 125 should preferably have a small diameter. Moreover, extraction buffer 126 and gel 122 are preferably kept at the same temperature.

In one embodiment, pipette 129 comprises a mechanized pipetter with built-in electrode 130A. The mechanized pipetter aspirates buffer into a disposable pipette tip, then partially dispenses the buffer to cover the gel inside capillary 125 so that there is conductivity between electrodes 130A and 130B. Computer monitoring may be used to monitor the current between electrodes 130A and 130B during extraction, and detect such problems as bubbles or evaporation that may create an open circuit between the electrodes. After extraction is complete, the remaining buffer in the pipette tip is disposed of, and the pipette tip may return to capillary 25 to extract further samples of particles. Mechanized pipetting may reduce unnecessary pipette tip motion so that there is minimal mixing of the concentrated particles with the surrounding buffer. This minimizes the extraction volume and hence increases final concentration of the particles to be extracted.

In another embodiment, instead of inserting a capillary filled with buffer into the gel, the gel may be cast with a cavity. The cavity is filled with a buffer solution, and a pipette having an electrode is inserted into the buffer. The cavity functions similarly to the capillary in collecting the particles for extraction. Molecules may be caused to enter such a cavity from the surrounding medium by generating a concentration gradient between the medium and the cavity by SCODA.

Figure 14:
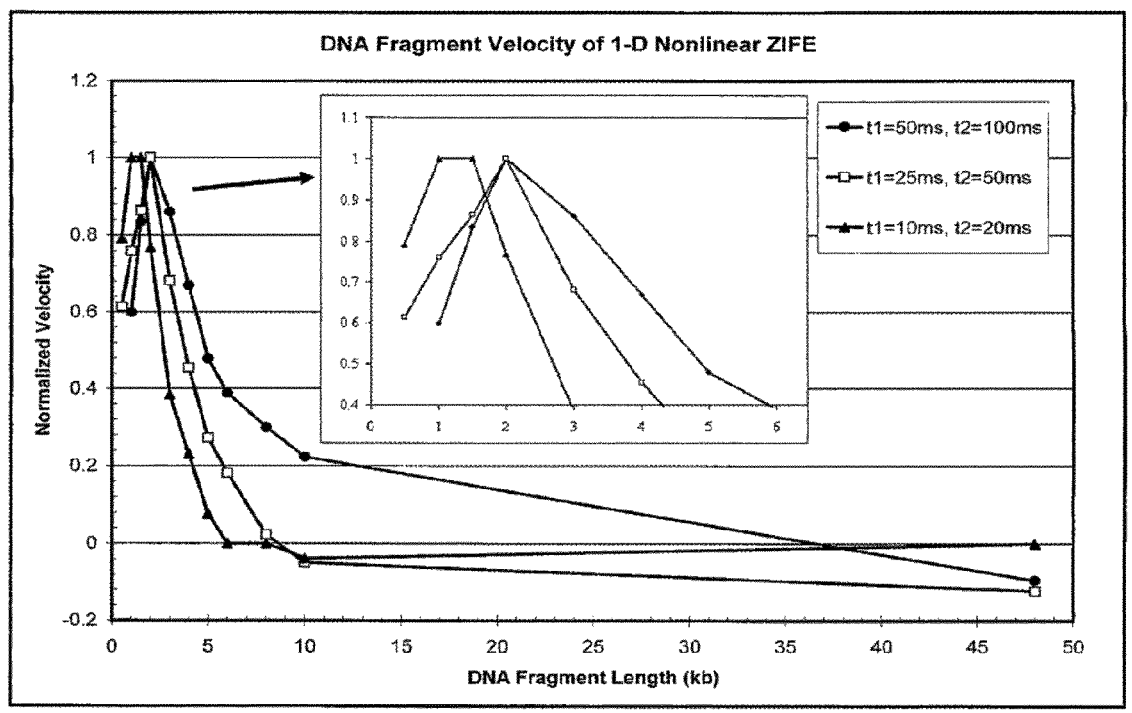
FIG. 14 is a graph illustrating the DNA fragment velocity during an experiment as a function of fragment length and cycle times.

Interface-ZIFE extraction of DNA mixtures from gels may be applied to selectively extract DNA fragments according to their size. If cycle times $t_1$ and $t_2$ for the electric field pulse are chosen to be sufficiently small, the relaxation or re-orientation time of the DNA molecules becomes significant and introduces a length-dependence in the migration velocity of the molecules. FIG. 14 is a graph illustrating the DNA fragment velocity during an experiment as a function of fragment length and cycle times $t_1$ and $t_2$. In that experiment, DNA fragments of different lengths were linearly separated using standard DC electrophoresis in a 1% agarose gel (0.1×TAE). ZIFE was then applied (in a direction perpendicular to that in which the DC electrophoresis was performed) to observe non-linear velocity of the fragments.

Figure 15:
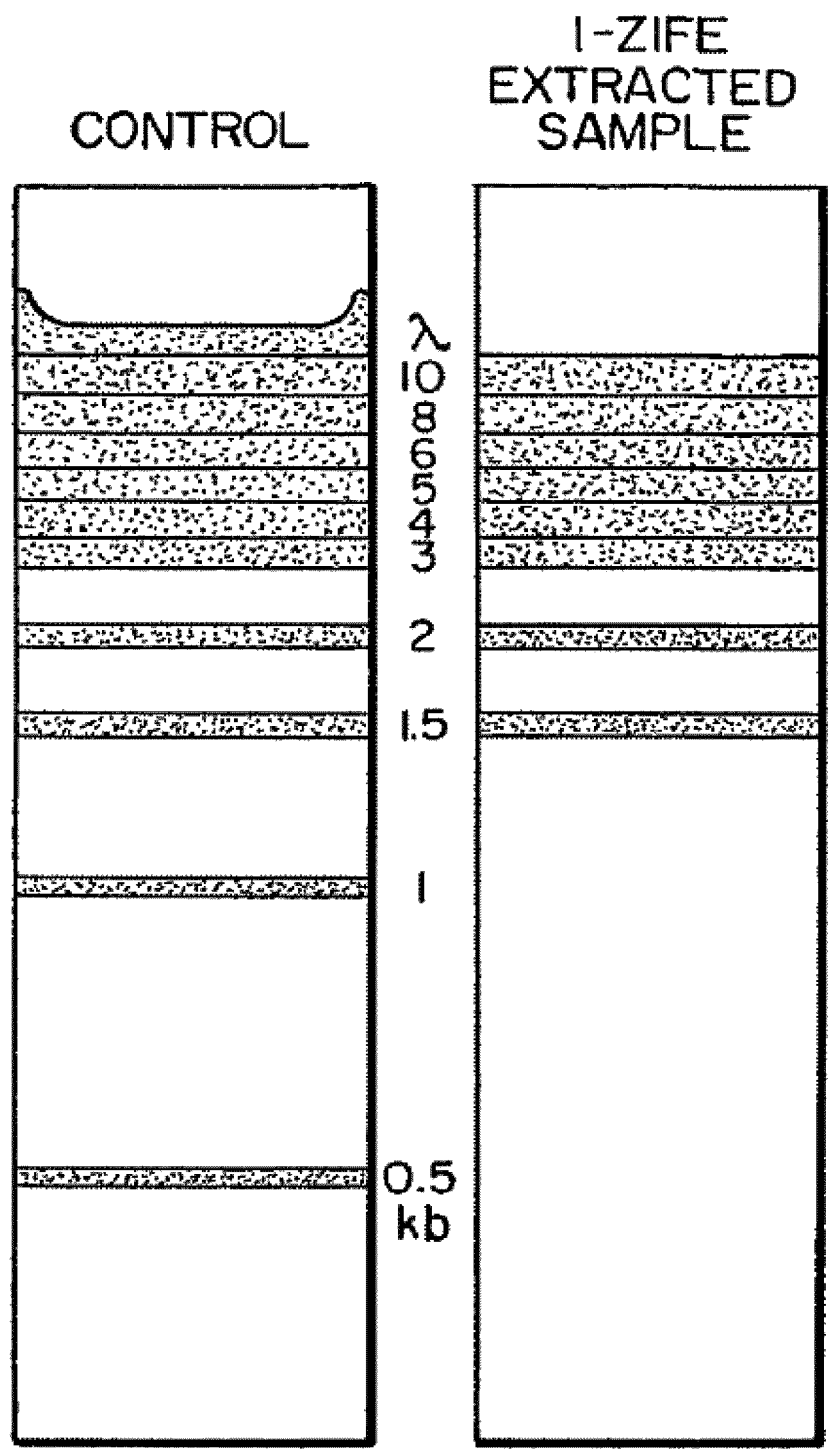
FIG. 15 shows a comparison between a DNA fragment mix and the fragment distribution of the same mix, after extraction.

FIG. 15 shows a comparison between a DNA fragment mix and the fragment distribution of the same mix, after Interface-ZIFE extraction. The mix comprised 2 μL λ DNA (48 kb, 500 ng/μL) and 4 μL 1 kb DNA ladder (0.5-10 kb, 500 ng/μL) and was run in 100 μL of 1% agarose gel applying the Interface-ZIFE extraction method described above. A pulsed electric field was applied, generated by a voltage $V_1=200$ V applied to the electrode in the pipette for a time of $t_1=25$ ms, which alternated with a voltage $V_2=-100$ V applied to the electrodes in the gel for a time of $t_2=50$ ms. The pulsed electric field was applied for 3 hours. This process extracted DNA into 0.1× TAE buffer which was mixed with loading dye and inserted into the well of a 1% agarose gel, along with a control from the original mix, for standard DC electrophoresis. The λ DNA band and short (less than 1 kb) fragments were not extracted from the gel. The size selection of Interface-ZIFE may be applied to longer fragments (100-200 kb) as well.

Parameters that can be varied to optimize extraction speed, extraction efficiency and DNA fragment length selectivity, include: magnitude of the electric pulsed field; frequency (cycle times) of the electric pulsed field; composition of the buffer in extraction reservoir 126; composition of gel 122; operating temperature; and the degree of concentration of molecules 128A.

The methods and apparatus disclosed herein may be applied for extracting charged particles from a medium where the particles are concentrated in a particular region of the medium (such as DNA molecules concentrated in a column or pillar in gel). However, the methods and apparatus are not limited to such application. They may also be employed to extract charged particles that are uniformly dispersed in the medium, located or concentrated in particular regions or bands, or otherwise distributed in the medium. Using the methods and apparatus disclosed herein, charged particles, and in particular biopolymers (for example, DNA, RNA and polypeptides), may be extracted from acrylamide, linear poly-acrylamide, POP (Perkin Elmer), agarose gels, entangled liquid solutions of polymers, viscous or dense solutions, solutions of polymers designed to bind specifically to the molecules whose motion is being directed, simple aqueous solutions, and the like. Interface-ZIFE used in conjunction with SCODA-based electrophoresis (for concentrating the DNA in a region) can be used to extract bacterial artificial chromosomes, plasmids and high molecular weight or genomic DNA.

IZIFE can be used to extract only selected particles from a medium. Particles having velocities that depend only linearly on the magnitude of an applied driving field will simply oscillate back and forth when exposed to an IZIFE driving field. Such particles will therefore remain in the medium while other particles having velocities having a non-linear dependence on applied field can be extracted from the medium. In some cases the IZIFE driving field can be constructed so that different particle species drift toward the second medium at different rates. The concentration of the different species at the interface between the media will therefore vary over time. A species which has a high net drift velocity under IZIFE will be extracted from the first medium before a species which has a lower net drift velocity.

By terminating IZIFE before slower species have been extracted from the first medium, the relative concentration of species having faster net drift velocities can be increased. By removing faster species that have accumulated at the interface before slower drifting species have arrived at the interface, one can increase the relative concentration at the interface of species having slower net drift velocities under IZIFE Example 17

Some Possible Variant Particle Extraction Methods and Apparatus

As will be apparent to those skilled in the art in the light of the foregoing disclosure, many alterations and modifications are possible in the practice of this invention without departing from the spirit or scope thereof, including but not limited to the following:

The extraction of uncharged, or electrically neutral, molecules may be accomplished using the methods and apparatus disclosed herein if those molecules are carried by charged molecules. For example, neutral proteins that interact with charged micelles may be extracted electrophoretically through their interaction with the micelles.

The waveform used for implementing ZIFE may be biased in one direction or the other. Biased ZIFE may facilitate selective separation of the particles according to their size.

Instead of using IZIFE to extract particles from a first medium into a second medium, one could use SCODA to extract particles from the first medium into a second medium. In some such embodiments a SCODA driving field that alternates in direction is directed across an interface between the first and second media. The SCODA driving field may, for example, be directed substantially perpendicularly to the interface. A SCODA mobility-varying field may be selected such that the mobility-varying field affects the mobility of the particles in the first medium so as to cause the particles in the first medium to travel in a direction toward the second medium. The mobility-varying field may be selected to affect the mobility of the particles the second medium to a degree substantially less than it affects the mobility of the particles in the first medium. In the best case, the mobility-varying field does not affect the mobility of particles in the second medium. In this example, the SCODA effect causes particles to be transported from the first medium into the second medium where the particles become concentrated at the interface between the first and second media. In an alternative embodiment, the mobility-varying field is applied only to those particles that are within the first medium so that the particles drift by SCODA into the second medium and become concentrated in the second medium.

Example 18

Separation of Differentially Modified Molecules

In some embodiments, molecules that are identical except for the presence or absence of a chemical modification that alters the binding affinity of the molecule for a probe are separated using affinity SCODA. Some embodiments of affinity SCODA are sufficiently sensitive to separate two molecules that have only a small difference in binding affinity for the immobilized affinity agent. Examples of such molecules include differentially modified molecules, such as methylated and unmethylated nucleic acids, methylated or acetylated proteins, or the like.

For example, it has been previously shown that methylation of cytosine residues increases the binding energy of hybridization relative to unmethylated DNA sequences. RNA sequences would be expected to display a similar increase in the binding energy of hybridization when methylated as compared to unmethylated sequences. The inventors have shown that one embodiment of affinity SCODA can be used to separate nucleic acid sequences differing only by the presence of a single methylated cytosine residue. Other chemical modifications would be expected to alter the binding energy of a nucleic acid and its complimentary sequence in a similar manner. Modification of proteins, such as through methylation, can also alter the binding affinity of a protein of interest with a protein, RNA or DNA aptamer, antibody, or other molecule that binds to the protein at or near the methylation site. Accordingly, embodiments of affinity SCODA can be used to separate differentially modified molecules of interest. While the examples herein are directed to methylation enrichment, affinity SCODA can also be applied to enrichment and selection of molecules with other chemical differences, including, e.g., acetylation.

Affinity SCODA, and sequence-specific SCODA, may be used to enrich a specific sequence of methylated DNA out of a background of methylated and unmethylated DNA. In this application of affinity SCODA, the strength of the SCODA focusing force may be related to the binding energy of the target DNA to the bound oligonucleotides. Target molecules with a higher binding energy may be made to focus more strongly than targets with lower binding energy. Methylation of DNA has previously been documented to slightly increase the binding energy of target DNA to its complementary sequence. Small changes in binding energy of a complementary oligonucleotide may be exploited through affinity SCODA to preferentially enrich for methylated DNA. SCODA operating conditions may be chosen, for example as described above, such that the methylated DNA is concentrated while unmethylated DNA of the same sequence is washed off the gel.

Some embodiments can separate molecules with a difference in binding energy to an immobilized affinity agent of less than kT, the thermal excitation energy of the target molecules. Some embodiments can separate molecules with a difference in binding energy to an immobilized affinity agent of less than 0.19 kcal/mol. Some embodiments can separate molecules with a difference in binding energy to an immobilized affinity agent of less than 2.6 kcal/mol. Some embodiments can separate molecules with a difference in binding energy to an immobilized affinity agent of less than 3.8 kcal/mol. Some embodiments can separate molecules that differ only by the presence of a methyl group. Some embodiments can separate nucleic acid sequences that differ in sequence at only one base.

Example 19

Mobility of a Target in an Affinity Matrix

The interactions between a target and immobilized probes in an affinity matrix can be described by first order reaction kinetics:

$$[T]+[P] \rightleftharpoons [T \ldots P] \tag{30}$$

Here [T] is the target, [P] the immobilized probe, [T ... P] the probe-target duplex, $k_f$ is the forward (hybridization) reaction rate, and $k_r$ the reverse (dissociation) reaction rate. Since the mobility of the target is zero while it is bound to the matrix, the effective mobility of the target will be reduced by the relative amount of target that is immobilized on the matrix:

$$\mu_{effective} = \mu_0 \frac{[T]}{[T]+[T \ldots P]} \tag{31}$$

where $\mu_0$ is the mobility of the unbound target. Using reasonable estimates for the forward reaction rate and an immobilized probe concentration that is significantly higher than the concentration of the unbound target, it can be assumed that the time constant for hybridization should be significantly less than one second. If the period of the mobility-altering field is maintained at longer than one second, it can be assumed for the purposes of analysis that the binding kinetics are fast and equation (30) can be rewritten in terms of reaction rates:

$$k_f[T][P] = k_r[T \ldots P] \tag{32}$$

$$[T] = \frac{k_r}{k_f} \frac{[T \ldots P]}{[P]} \tag{33}$$

Inserting (33) into equation (31) and simplifying yields:

$$\mu_{effective} = \mu_0 \frac{1}{1 + \frac{k_f}{k_r}[P]} \tag{34}$$

From this result it can be seen that the mobility can be altered by modifying either the forward or reverse reaction rates. Modification of the forward or reverse reaction rates can be achieved in a number of different ways, for example by adjusting the temperature, salinity, pH, concentration of denaturants, concentration of catalysts, by physically pulling duplexes apart with an external electric field, or the like. In one exemplary embodiment described in greater detail below, the mechanism for modifying the mobility of target molecules moving through an affinity matrix is control of the matrix temperature.

To facilitate analysis, it is helpful to make some simplifying assumptions. First it is assumed that there are a large number of immobilized probes relative to target molecules. So long as this is true, then even if a large fraction of the target molecules become bound to the probes the concentration of free probes, [P], will not change much and it can be assumed that [P] is constant. Also, it is assumed that the forward reaction rate $k_f$ does not depend on temperature. This not strictly true, as the forward reaction rate does depend on temperature. Secondary structure in the immobilized probe or in the target molecule can result in a temperature dependent forward reaction rate. However, in embodiments operating at a temperature range near the duplex melting temperature the reverse reaction rate has an exponential dependence on temperature and the forward reaction rate has a much weaker temperature dependence, varying by about 30% over a range of 30° C. around the melting temperature. It is additionally assumed that the target sequence is free of any significant secondary structure. Although this final assumption would not always be correct, it simplifies this initial analysis.

To determine the temperature dependence of the reverse reaction rate, an Arrhenius model for unbinding kinetics is assumed. This assumption is justified by recent work in nanopore force spectroscopy.

$$k_r = A e^{\frac{\Delta G}{k_b T}} \tag{35}$$

Here A is an empirically derived constant, $\Delta G$ is the probe-target binding energy, $k_b$ is the Boltzmann constant, and T the temperature. Inserting this into (34), rewriting the free energy $\Delta G$ as $\Delta H - T\Delta S$, and collecting constant terms allows the mobility to be rewritten as:

$$\mu_{effective} = \mu_0 \frac{1}{1 + \beta e^{\frac{-\Delta H + T\Delta S}{k_b T}}} \tag{36}$$

Figure 16:
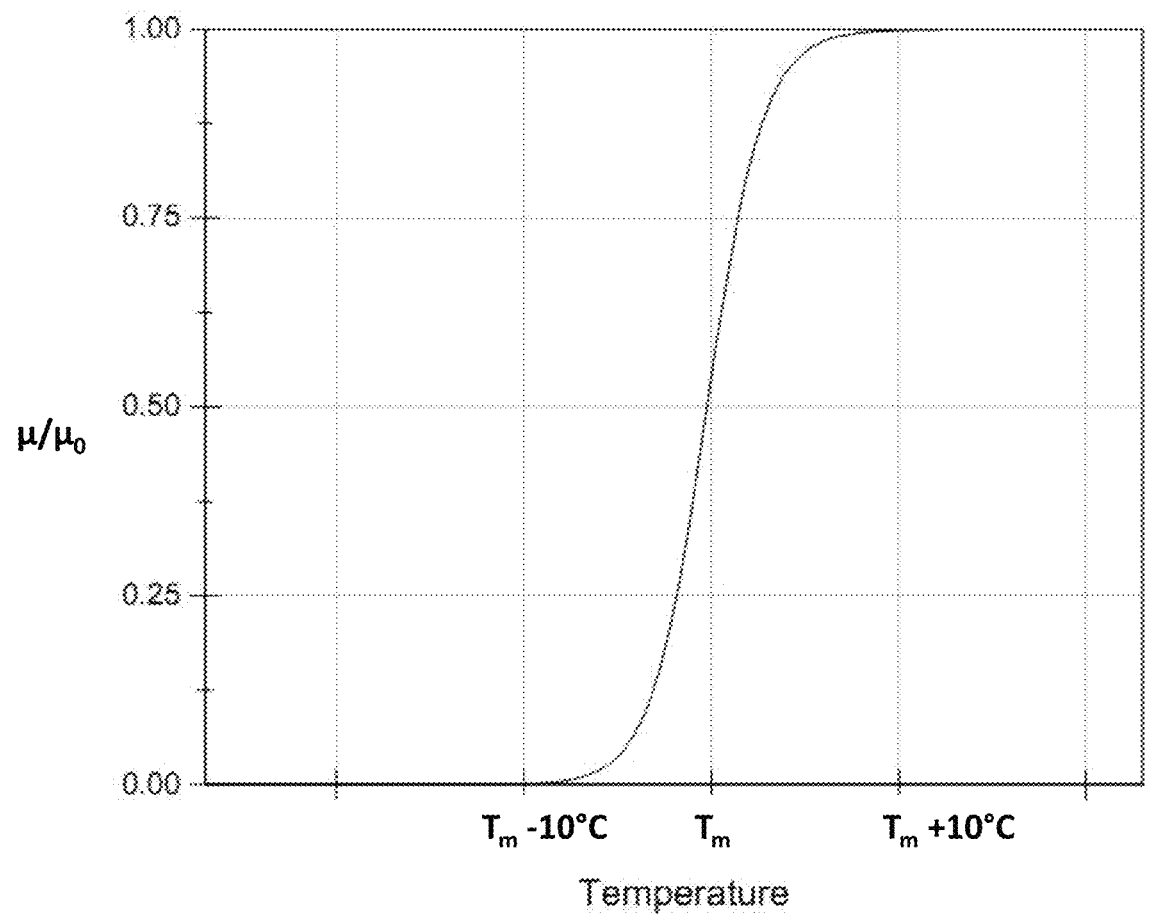
FIG. 16 shows a plot of equation (36) near the duplex melting temperature, $T_m$, illustrating the relative change in mobility as a function of temperature.

Equation (36) describes a sigmoidal mobility temperature dependence. The shape of this curve is shown in FIG. 16. At low temperature the mobility is nearly zero. This is the regime where thermal excitations are insufficient to drive target molecules off of the affinity matrix. At high temperature target molecules move at the unbound mobility, where the thermal energy is greater than the binding energy. Between these two extremes there exists a temperature range within which a small change in temperature results in a large change in mobility. This is the operating regime for embodiments of affinity SCODA that utilize temperature as the mobility altering parameter.

In embodiments of affinity SCODA used to separate nucleic acids based on sequence, i.e. sequence-specific SCODA, this temperature range tends to lie near the melting temperature of the probe-target duplex. Furthermore, the speed of concentration is proportional to k, which is a measure of how much the mobility changes during one SCODA cycle. Operating near the probe-target duplex melting temperature, where the slope of the mobility versus temperature curve is steepest, maximizes k for a given temperature swing during a SCODA cycle in embodiments where temperature is used as the mobility altering parameter.

In some embodiments, affinity SCODA may be conducted within a temperature gradient that has a maximum amplitude during application of SCODA focusing fields that varies within about ±20° C., within about ±10° C., within about ±5° C., or within about ±2° C. of the melting temperature of the target molecule and the affinity agent.

It is possible to describe affinity SCODA in one dimension by replacing the time dependent mobility of equation (30) with the temperature dependent mobility of equation (36) and a time dependent temperature:

$$T(x, t) = T_m + T_a \left(\frac{x}{L}\right) \sin(\omega t + \phi) \tag{37}$$

Here, the temperature oscillates around $T_m$, the probe target melting temperature, and $T_a$ is the maximum amplitude of the temperature oscillations at $x=\pm L$. To get an analytical expression for the drift velocity, $v_d=\mu E$, as a function of temperature, a Taylor expansion of equation (36) is performed around $T_m$:

$$\mu_{effective} = \mu(T_m) - \frac{\mu_b \beta \Delta H e^{\frac{-\Delta H + T\Delta S}{k_b T_m}}}{k_b T_m^2 \left(1 + \beta e^{\frac{-\Delta H + T\Delta S}{k_b T_m}}\right)^2} (T - T_m) + O((T - T_m)^2) \tag{38}$$

which can be rewritten as:

$$\mu_{effective} = \mu(T_m) + \alpha(T - T_m) + O((T - T_m)^2) \tag{39}$$

Here the first term in the Taylor expansion has been collected into the constant $\alpha$. Combining (37) and (39) into an expression for the mobility yields an expression similar to (40):

$$\mu(t) = \mu(T_m) + \left(\frac{\alpha T_a x}{L}\right) \sin(\omega t + \phi) \tag{40}$$

Equation (40) can be used to determine the time averaged drift velocity for both the one dimensional and two dimensional cases by simply replacing k with:

$$\alpha \frac{T_a}{L} = \frac{\mu_o \beta \Delta H e^{\frac{-\Delta H + T\Delta S}{k_b T_m}}}{k_b T_m^2 \left(1 + \beta e^{\frac{-\Delta H + T\Delta S}{k_b T_m}}\right)^2} \left(\frac{T_a}{L}\right) \tag{41}$$

The drift velocity is then given by:

$$\overline{v}_d(x, t) = \frac{\alpha T_a x}{2L} E_0 \cos(\phi) \tag{42}$$

in one dimension, and:

$$\overline{v}_d = \frac{E_0 \alpha T_a r}{2L} (\cos(\phi)\hat{r} + \sin(\phi)\hat{\theta}) \tag{43}$$

in two dimensions. This result shows that if a two dimensional gel is functionalized with immobilized probes (i.e. an affinity matrix), then by combining a rotating temperature gradient with a rotating dipole electric field, all target molecules should be forced towards a central region in the gel, thus concentrating a target molecule that binds to the immobilized probes.

Example 20

Molecular Separation with Affinity SCODA

In some embodiments, affinity SCODA is used to separate two similar molecules (e.g. the same molecule that has been differentially modified, or which differs in sequence at only one or a few locations) with differing binding affinities for the immobilized probe. Beginning with two molecular species, each with a different binding energy to the immobilized probes, these two molecular species can be separated by superimposing a washing motive force over the driving and mobility altering fields used to produce SCODA focusing, to provide net motion of molecules that have a lesser binding affinity for the immobilized probe (i.e. the molecules that have a higher binding affinity for the immobilized probe are preferentially focused during the application of the SCODA focusing fields). In some embodiments, the washing force is a small applied DC force, referred to herein as a DC bias.

In the one dimensional case when a small DC force is applied as a washing or bias force, the electric field becomes:

$$E(x,t)=E_0 \sin(\omega t)+E_b \tag{44}$$

where $E_b$ is the applied DC bias. The final drift velocity has superimposed on the SCODA focusing velocity a constant velocity proportional to the strength of the bias field:

$$\overline{v}_d(x, t) = \frac{\alpha T_a x}{2L} E_0 \cos(\phi) + \mu(T_m) E_b \tag{45}$$

This drift velocity will tend to move the final focus location either to the left or right depending on the direction of bias. The amount by which this bias moves a focus off center depends on the strength of the interaction between the target and probe molecules. The differential strength of the target-probe interaction can therefore serve as a mechanism to enable molecular separation of two highly similar species.

Figure 17:
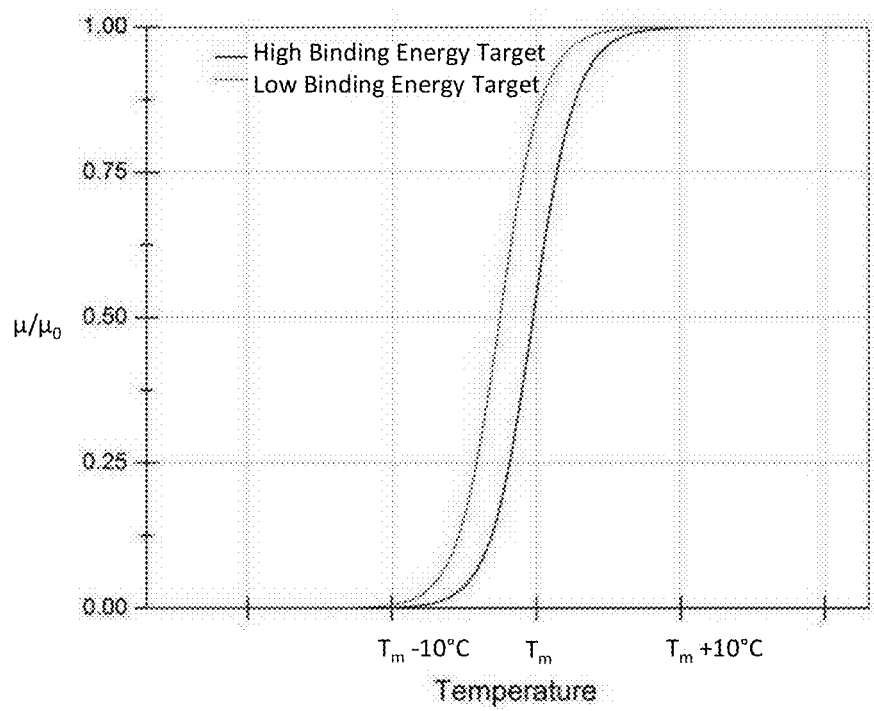
FIG. 17 shows a plot of mobility versus temperature for two different molecules with different binding energies to immobilized probe molecules. The mobility of the high binding energy target is shown by the curve on the right, while the mobility of the low binding energy target is shown by the curve on the left.

Consider two molecules that have different binding affinities for an immobilized probe. Reducing the probe-target binding energy, $\Delta G$ in equation (36), will serve to shift the mobility versus temperature curve to the left on the temperature scale as shown in FIG. 17. The mobility of the high binding energy target is shown by the curve on the right, while the mobility of the low binding energy target is shown by the curve on the left.

If the SCODA system in this exemplary embodiment is operated at the optimal focusing temperature for the higher binding energy molecule, $T_m$ in FIG. 17, then the mobility of the lower binding energy molecule will be higher and will have weaker temperature dependence. In terms of equation (45) the molecule with lower binding energy will have a larger value of $\mu(T_m)$ and a smaller value of $\alpha$. This means that a lower binding energy molecule will have a lower SCODA drift velocity and a higher velocity under DC bias, resulting in a different final focus location than the high binding energy molecule as illustrated in FIG. 18.

Figure 18:
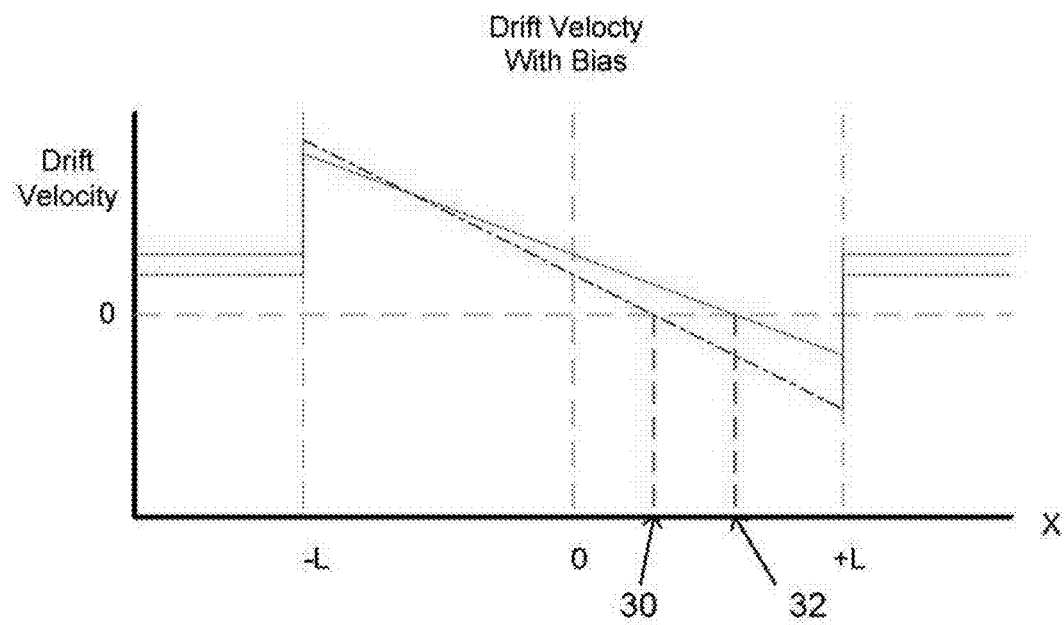
FIG. 18 shows the effect of an applied DC washing bias on molecules with two different binding energies. The solid curve represents the drift velocity of a target molecule with a lower binding energy to the bound probes than the molecules represented by the dashed curve.

FIG. 18 shows the effect of an applied DC bias on molecules with two different binding energies for the immobilized probe according to one embodiment. The solid curve represents the drift velocity of a target molecule with a lower binding energy to the bound probes than the molecules represented by the dashed curve. The final focus location is the point where the drift velocity is equal to zero. The molecules represented by the solid curve have both a lower SCODA drift velocity and a higher DC velocity compared to the molecules represented by the dashed curve. When SCODA focusing is combined with a DC bias the lower binding energy molecules will focus further away from the unbiased focus at x=0, resulting in two separate foci, one for each molecular species. The final focus position for the high binding energy molecule is indicated by reference numeral 30. The final focus position for the low binding energy molecule is indicated by reference numeral 32.

The two dimensional case is the same as the one dimensional case, the superimposed velocity from the applied washing bias moves the final focus spot off center in the direction of the washing bias.

In some embodiments, if the difference in binding energies between the molecules to be separated is large enough and a sufficiently high washing bias is applied, the low binding energy molecules can be washed off of the affinity matrix while molecules with higher binding energy are retained in the affinity matrix, and may be captured at a focus location within the affinity matrix (i.e. preferentially focused) through the application of SCODA focusing fields.

Example 21

Generation of a Time Varying Temperature Gradient

Embodiments of affinity SCODA that use variations in temperature as the mobility altering field may use a periodically varying temperature gradient to produce a convergent velocity field. A periodically varying temperature gradient may be provided in any suitable manner, for example by the use of heaters or thermoelectric chillers to periodically heat and cool regions of the medium, the use of radiative heating to periodically heat regions of the medium, the application of light or radiation to periodically heat regions of the medium, Joule heating using the application of an electric field to the medium, or the like.

A periodically varying temperature gradient can be established in any suitable manner. For example, a temperature gradient may allow a particle increased mobility (i.e. at a higher temperature) when a driving field is applied toward the focus spot than when a driving field is applied away from the focus spot. In some embodiments, the temperature gradient is rotated to produce a convergent velocity field in conjunction with the application of a time-varying driving force.

In some embodiments, Joule heating using an electric field is used to provide a temperature gradient. In some embodiments, the electric field used to provide Joule heating to provide a temperature gradient is the same as the electric field that provides the driving field. In some embodiments, the magnitude of the electric field applied is selected to produce a desired temperature gradient within an affinity matrix.

In some embodiments, a spatial temperature gradient is generated using a quadrupole electric field to provide the Joule heating. In some such embodiments, a two dimensional gel with four electrodes is provided. Voltages are applied to the four electrodes such that the electric field in the gel is non-uniform, containing regions of high electric field (and consequently high temperature) and low electric field. The electric field is oriented such that the regions of high electric field tend to push negatively charged molecules towards the center of the gel, while regions of low electric field tend to push such molecules away from the center of the gel. In some such embodiments, the electric field that provides the temperature gradient through Joule heating is also the electric field that applies a driving force to molecules in the gel.

Figure 19:
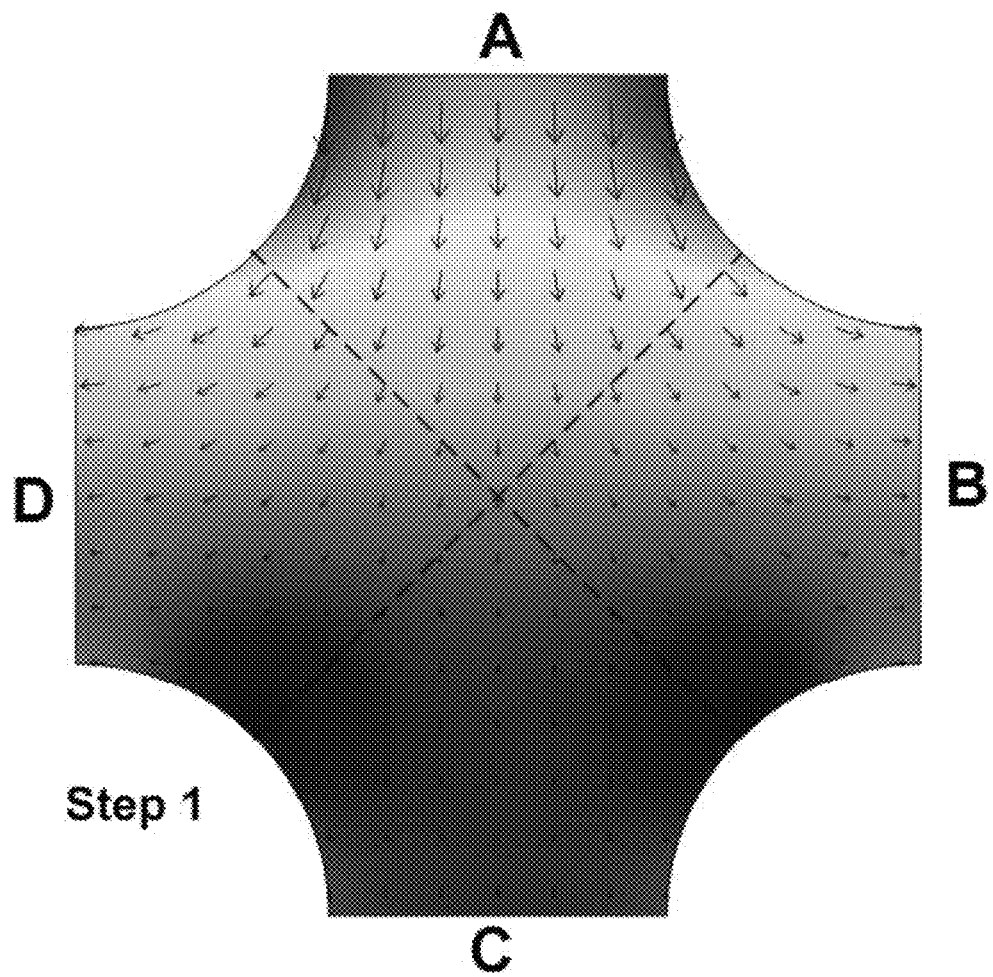
FIG. 19 shows an example of an electric field pattern suitable for two dimensional SCODA based concentration in some embodiments. Voltages applied at electrodes A, B, C, and D, are −V, 0, 0, and 0 respectively. Arrows represent the velocity of a negatively charged analyte molecule such as DNA. Color intensity represents electric field strength.

An example of such a field pattern is illustrated in FIG. 19. Voltages applied at electrodes A, B, C and D in FIG. 19 are −V, 0, 0, and 0 respectively. Arrows represent the velocity of a negatively charged analyte molecule. Color intensity represents electric field strength. The regions near electrode A have a high electric field strength, which decreases towards electrode C. The high field regions near electrode A tend to push negatively charged molecules towards the center of the gel, while the lower field regions near electrodes B, C, and D tend to push negatively charged molecules away from the center of the gel. In embodiments in which the electric field also provides the temperature gradient, the affinity matrix will become hotter in regions of higher field strength due to Joule heating. Hence, regions of high electric field strength will coincide with regions of higher temperature and thus higher mobility. Accordingly, molecules in the high electric field regions near electrode A will tend to move a greater distance toward the center of the gel, while molecules in the lower electric field regions near electrodes B, C, and D have a lower mobility (are at a cooler temperature) and will move only a short distance away from the center of the gel.

Figure 20:
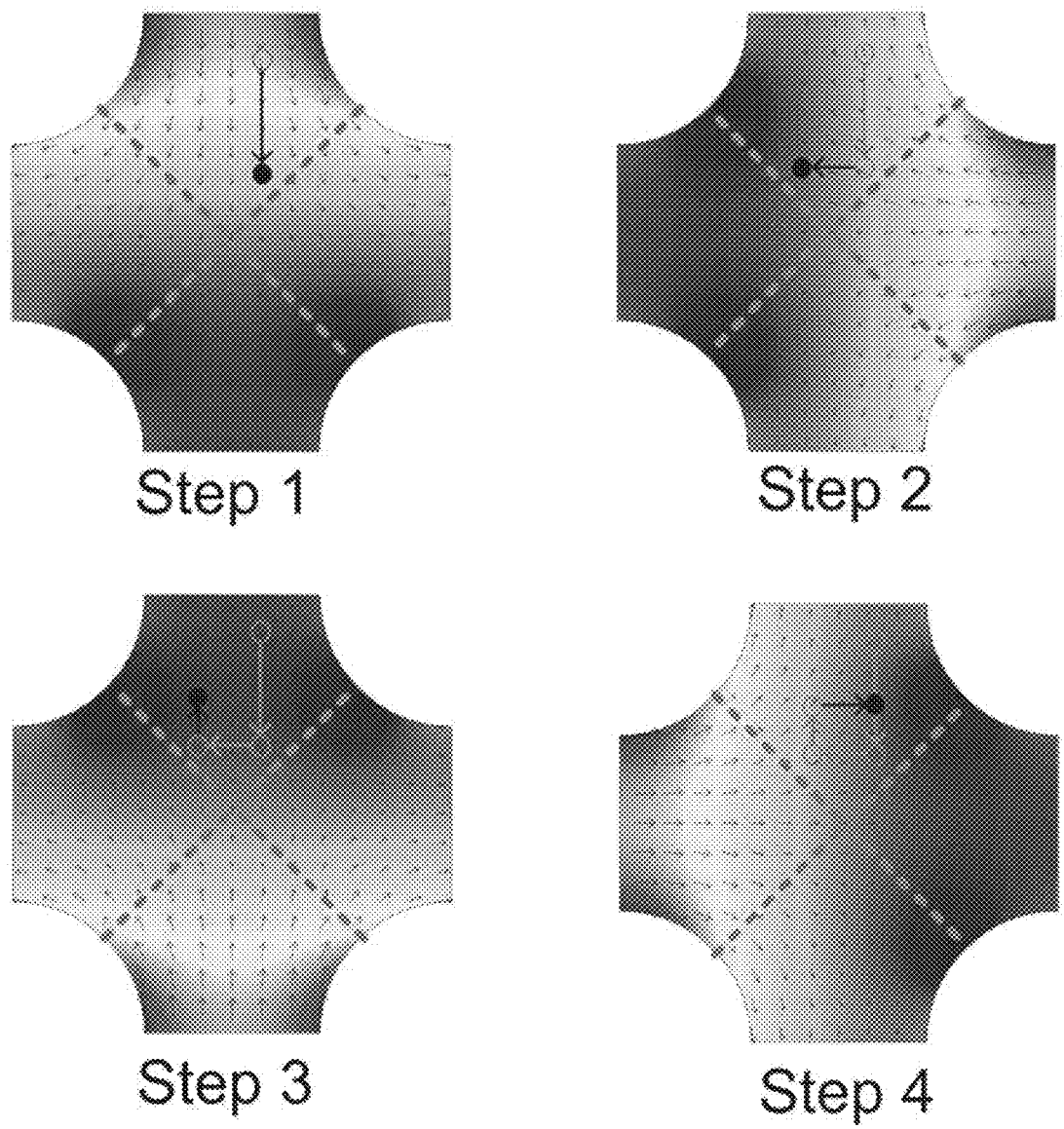
FIG. 20 shows stepwise rotation of the electric field leading to focusing of molecules whose mobility increases with temperature in one embodiment of affinity SCODA. A particle path is shown by the arrows.

In some embodiments, the electric field pattern of FIG. 19 is rotated in a stepwise manner by rotating the voltage pattern around the four electrodes such that the time averaged electric field is zero as shown in FIG. 20. This rotating field will result in net migration towards the center of the gel for any molecule that is negatively charged and has a mobility that varies with temperature. In some embodiments, the electric field pattern is varied in a manner other than rotation, e.g. by sequentially shifting the voltage pattern by 180°, 90°, 180°, and 90°, or by randomly switching the direction of the electric field. As shown above, the mobility of a molecule moving through an affinity matrix depends on temperature, not electric field strength. The applied electric field will tend to increase the temperature of the matrix through Joule heating; the magnitude of the temperature rise at any given point in the matrix will be proportional to the square of the magnitude of the electric field.

In embodiments in which the thermal gradient is provided by Joule heating produced by the electric field that also provides the driving field, the oscillations in the thermal gradient will have the same period as the electric field oscillations. These oscillations can drive affinity SCODA based concentration in a two dimensional gel.

FIG. 20 illustrates the stepwise rotation of the electric field leading to focusing of molecules whose mobility increases with temperature or electric field according to such an embodiment. A particle path for a negatively charged molecule is shown. After four steps the particle has a net displacement toward the center of the gel. Molecules that do not experience a change in mobility with changing temperature or electric field will experience zero net motion in a zero time averaged electric field.

Example 22

Theoretical Predictions of Focusing and Separation

In some embodiments, the electric field and subsequently the Joule heating within an affinity SCODA gel are controlled by both the voltage applied to the source electrodes, and the shape of the gel. For example, superimposed rotating dipole and quadrupole fields can be used to drive electrophoretic SCODA concentration. The ratio of the strength of these two fields, the dipole to quadrupole ratio (DIQ), has an impact on the efficiency of SCODA focusing with a maximum at around DIQ=4.5, however the optimum is relatively flat with the SCODA force staying relatively constant for values between 1.75 and 10. One convenient choice of DIQ is 2. With this particular choice, only two distinct potentials need to be applied to the source electrodes, which can be achieved by connecting one electrode to a common voltage rail, grounding the other three, and rotating this pattern in a stepwise manner through the four possible configurations as shown in Table 2. Although analog amplifiers can be used and were used in the examples described herein, using a D/Q ratio of 2 allows one to use discrete MOSFET switches, which simplifies and reduces the required size and complexity of the power supplies.

TABLE 2

Voltage pattern for SCODA focusing with D/Q = 2.

|  | Electrode A | Electrode B | Electrode C | Electrode D |
|---|---|---|---|---|
| Step 1 | −V | 0 | 0 | 0 |
| Step 2 | 0 | −V | 0 | 0 |
| Step 3 | 0 | 0 | −V | 0 |
| Step 4 | 0 | 0 | 0 | −V |

A starting point for a sequence specific gel geometry was the four-sided gel geometry used for the initial demonstration of electrophoretic SCODA. This geometry can be defined by two numbers, the gel width and the corner radius. The inventors started by using a geometry that had a width of 10 mm and a corner radius of 3 mm. An electro-thermal model of this geometry was implemented in COMSOL MULTIPHYSICS® modeling software (COMSOL, Inc, Burlington Mass., USA) to estimate the electric field and temperature profiles within the gel and establish whether or not those field and temperature profiles could drive concentration of a target with a temperature dependent mobility. The model used simultaneously solves Ohm's Law and the heat equation within the domain, using the power density calculated from the solution of Ohm's Law as the source term for the heat equation and using the temperature solution from the heat equation to determine the temperature dependent electrical conductivity of the electrolyte in the gel.

Figure 21:
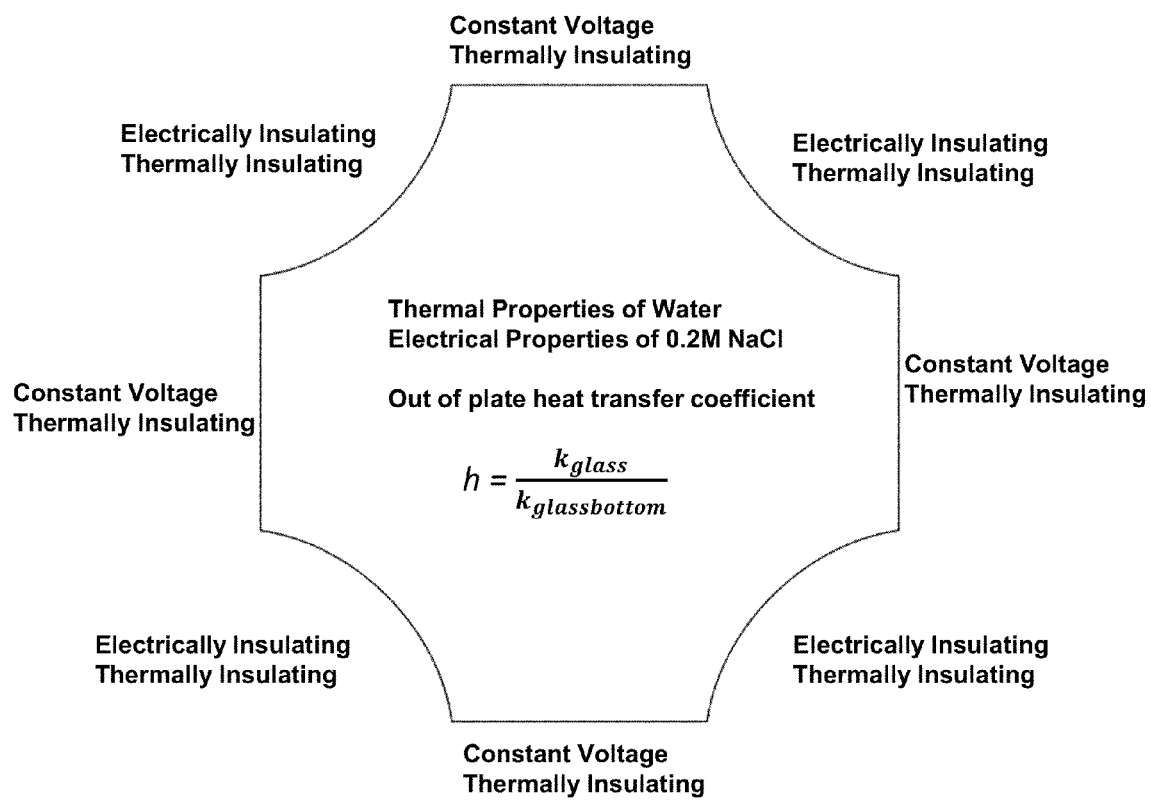
FIG. 21 shows the gel geometry including boundary conditions and bulk gel properties used for electrothermal modeling.
Figure 22:
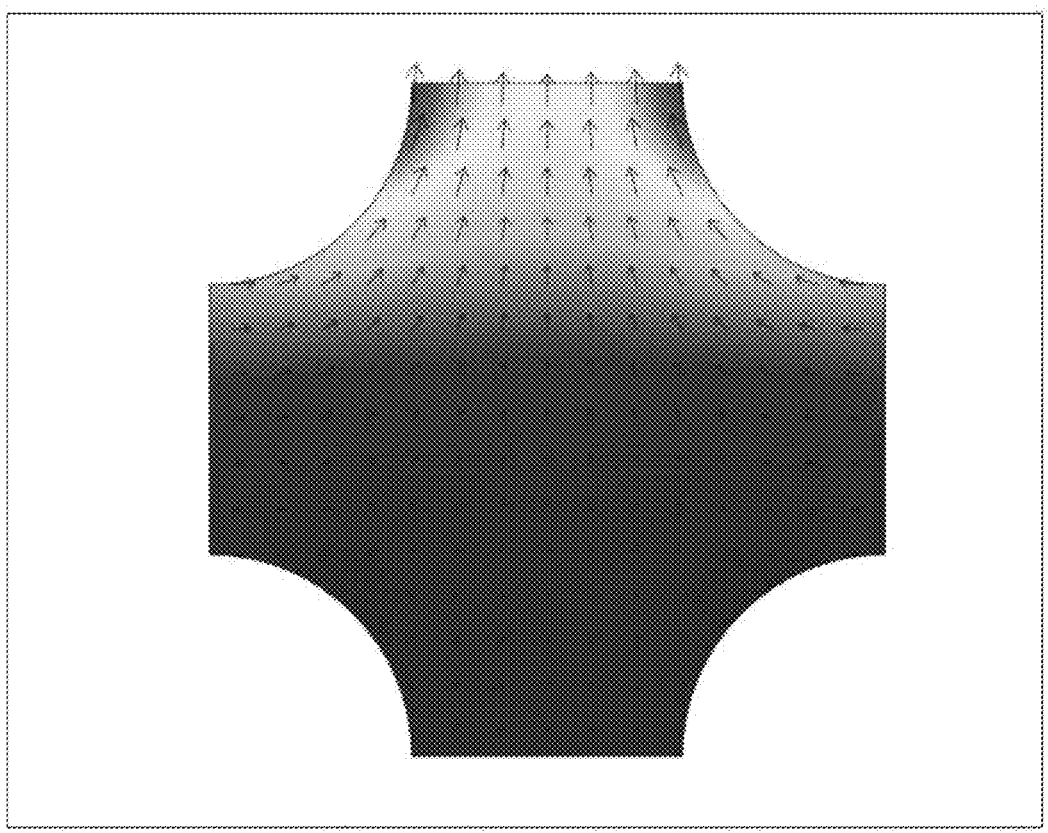
FIG. 22 shows the results of an electrothermal model for a single step of the SCODA cycle in one embodiment. Voltage applied to the four electrodes was −120 V, 0 V, 0 V, 0 V. Spreader plate temperature was set to 55° C. (328 K).

To obtain an accurate estimate of the temperature profile within the gel, the heat conducted out of the top and bottom of the gel are modeled. Boundary conditions and other model parameters are illustrated in FIG. 21. The thermal properties of water and electrical properties of 0.2 M NaCl were used. The gel cassettes are placed on an aluminum spreader plate that acts as a constant temperature reservoir. To model heat flow into the spreader plate the heat transfer coefficient of the glass bottom, given by k/t, was used. The temperature and electric field profiles solved by this model for a single step of the SCODA cycle are shown in FIG. 22. The voltage applied to the four electrodes was −120 V, 0 V, 0 V, 0 V, and the spreader plate temperature was set to 55° C. (328 K). The color map indicates gel temperature and the vector field shows the relative magnitude and direction of the electric field within the gel. Note that as DNA is negatively charged its migration direction will be opposite to the direction of the electric field.

Using experimentally determined values of mobility versus temperature for a given molecule and the thermal model described above, it is possible to determine the SCODA velocity everywhere in the gel for that particular molecule by taking the time average of the instantaneous drift velocity integrated over one complete cycle:

$$\vec{v}_s = \frac{1}{\tau}\int_0^\tau \mu(T(\vec{r},t))\vec{E}(\vec{r},t)dt \tag{46}$$

where μ is the temperature dependent mobility, E the electric field and τ the period of the SCODA cycle. The temperature and electric field were solved for four steps in the SCODA cycle and coupled with the mobility function in equation (36). In this manner, the SCODA velocity everywhere in the gel can be calculated. Since discrete steps are being used, if it is assumed that the period is long enough that the phase lag between the electric field and temperature can be neglected, then the integral in equation (46) becomes a sum:

$$\vec{v}_s = \frac{\Sigma \mu(T_i(\vec{r}))\vec{E}_i(\vec{r})t_i}{\Sigma t_i} \tag{47}$$

where the velocity is summed over all four steps in the cycle.

Figure 23:
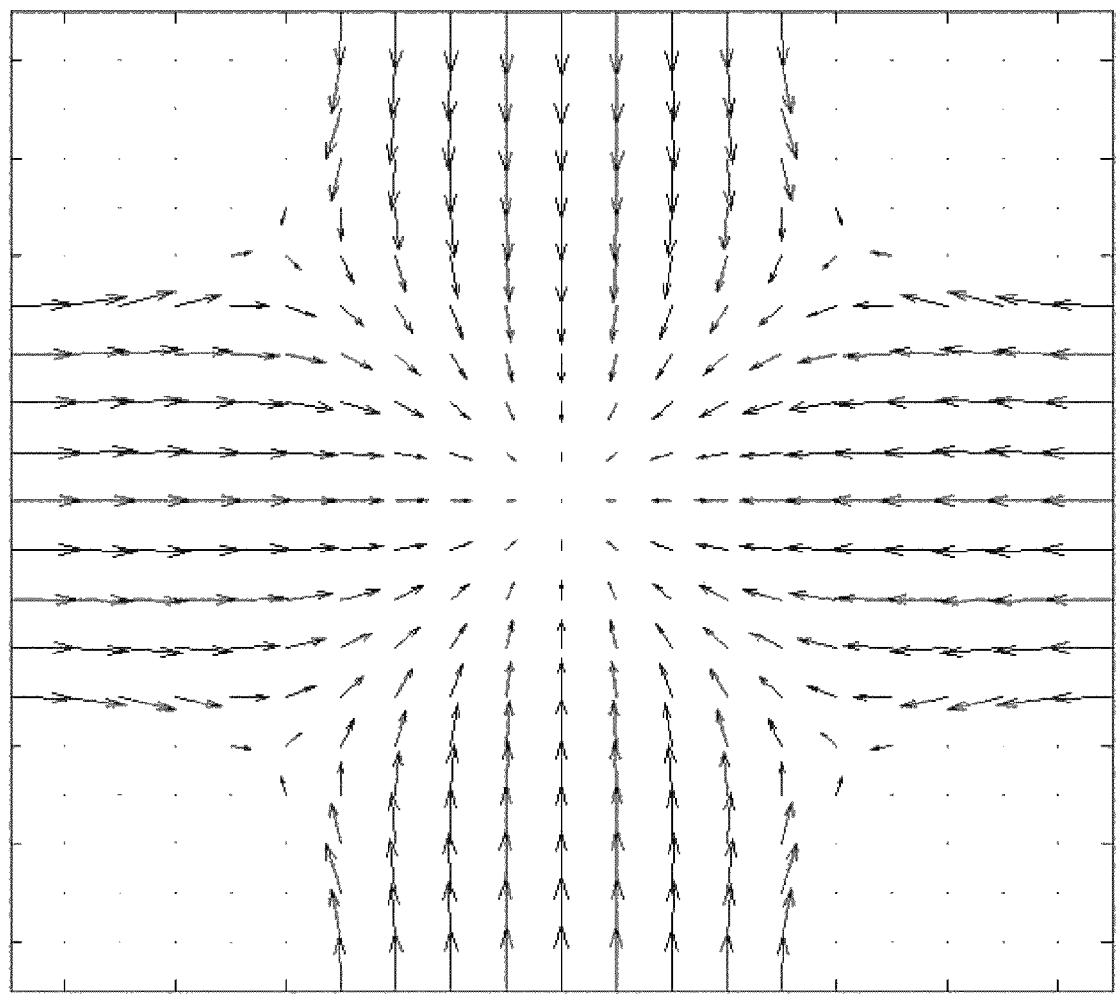
FIG. 23 shows SCODA velocity vector plots in one exemplary embodiment of the invention.

As an example, FIG. 23 shows a vector plot of the SCODA velocity using the experimentally determined mobility versus temperature curve for the perfect match target shown in FIG. 25 (example described below) and the temperature and electric field values calculated above.

The velocity field plotted in FIG. 23 shows a zero velocity point at the geometric center of the gel, with the velocity at all other points in the gel pointing towards the center. Thus, target molecules can be collected within the gel at the center of the electric field pattern.

In embodiments that are used to separate two similar molecules based on differences in binding affinity for the immobilized probe, a washing force is superimposed over the SCODA focusing fields described above. In some embodiments, the washing force is a DC electric field, described herein as a DC bias. For molecules having affinity to the immobilized probe, the SCODA focusing force applied by the SCODA focusing fields described above will tend to counteract movement of a molecule caused by the washing field, i.e. the SCODA focusing fields will tend to exert a restoring force on the molecules and the molecules will be preferentially focused as compared with molecules having a smaller binding affinity. Molecules that have a smaller binding affinity to the immobilized probe will have a greater mobility through the affinity matrix, and the restoring SCODA force will be weaker. As a result, the focus spot of molecules with a smaller binding affinity will be shifted. In some cases, the restoring SCODA force will be so weak that such molecules with a smaller binding affinity will be washed out of the affinity matrix altogether.

In order to enrich for a specific biomolecule from a population of other similar biomolecules using affinity SCODA, one may operate SCODA focusing electric fields with a superimposed DC bias. The DC bias may move the focused molecules off center, in such a way that the molecules with a lower binding energy to the immobilized binding sites move further off center than the molecules with higher binding energies, thus causing the focus to split into multiple foci. For molecules with similar binding energies, this split may be small while washing under bias. The DC bias may be superimposed directly over the focusing fields, or a DC field may be time multiplexed with the focusing fields.

In one exemplary embodiment used to separate nucleic acids having similar sequences, a DC bias is superimposed over the voltage pattern shown in Table 2, resulting in the voltage pattern shown below in Table 3. In some embodiments, the DC bias is applied alternately with the SCODA focusing fields, i.e. the SCODA focusing fields are applied for a period of time then stopped, and the DC bias is applied for a period of time then stopped.

TABLE 3

Applied voltages for focusing under a DC bias. Shown are values for a 120 V SCODA focusing potential superimposed over a 10 V DC bias.

|  | Electrode A | Electrode B | Electrode C | Electrode D |
|---|---|---|---|---|
| Step 1 | −120 | 5 | 10 | 5 |
| Step 2 | 0 | −115 | 10 | 5 |
| Step 3 | 0 | 5 | −110 | 5 |
| Step 4 | 0 | 5 | 10 | −115 |

Figure 24A:
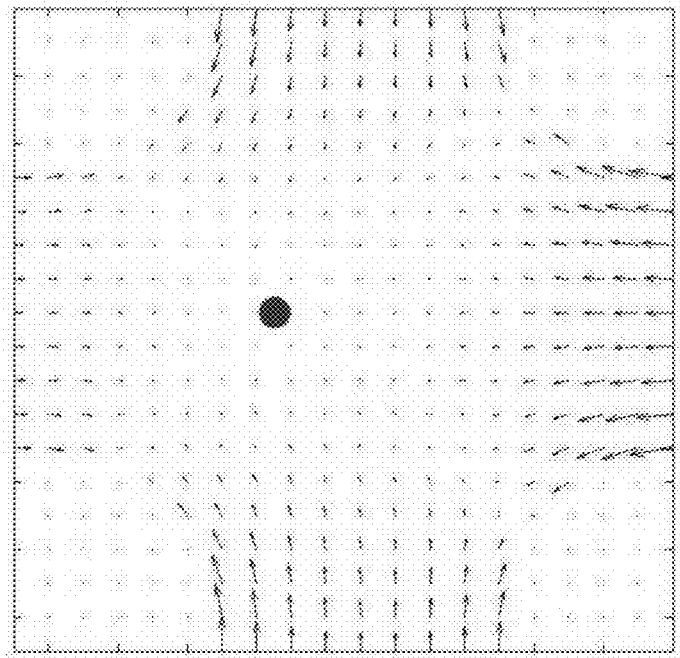
FIGS. 24A and 24B show predictions of SCODA focusing under the application of a DC washing bias in one embodiment.
Figure 24B:
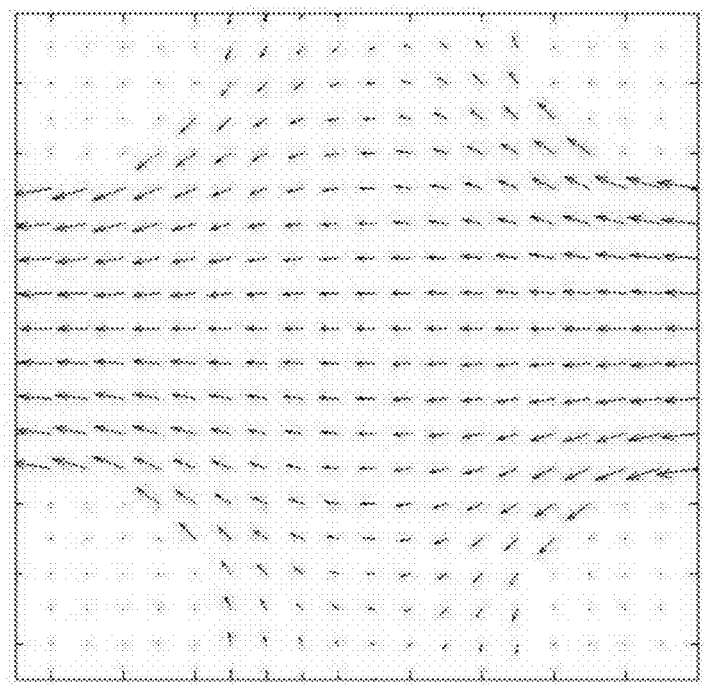

The resulting velocity plots of both the perfect match and single base mismatch targets in the presence of the applied DC bias are shown in FIGS. 24A and 24B, respectively. Electric field and temperature were calculated using COMSOL using a spreader plate temperature of 61° C. Velocity was calculated using equation (47) and the experimentally obtained data fits shown in FIG. 25 (see description below). The zero velocity location of the perfect match target has been moved slightly off center in the direction of the bias (indicated with a circular spot), however the mismatch target has no zero velocity point within the gel. These calculations show that it is possible to completely wash a target with a smaller binding affinity from the immobilized probe from the gel area while capturing the target with a higher binding affinity, enabling selective purification, concentration and/or detection of a specific sequence, even where the nucleotide targets differ in sequence at only one position.

In some embodiments, the optimal combination of the driving field and the mobility altering field used to perform SCODA focusing where there is a maximum difference in focusing force between similar molecules is empirically determined by measuring the velocity of sample molecules through a medium as a function of the mobility varying field. For example, in some embodiments the mobility of a desired target molecule and a non-desired target molecule at various temperatures is measured in an affinity matrix as described above, and the temperature range at which the difference in relative mobility is greatest is selected as the temperature range for conducting affinity SCODA. In some embodiments, the focusing force is proportional to the rate at which the velocity changes with respect to the perturbing field dv/df, where v is the molecule velocity and f the field strength. One skilled in the art may maximize dv/df so as to maximize SCODA focusing and to enable fast washing of contaminants that do not focus. To maximally separate two similar molecules, affinity SCODA may be carried out under conditions such that $dv_a/df - dv_b/df$ (where $v_a$ is the velocity of molecule a, and $v_b$ is the velocity of molecule b) is maximized.

In some embodiments, the strength of the electric field applied to an affinity matrix is calculated so that the highest temperature within the gel corresponds approximately to the temperature at which the difference in binding affinity between two molecules to be separated is highest.

In some embodiments, the temperature at which the difference in binding affinity between the two molecules to be separated is highest corresponds to the temperature at which the difference between the melting temperature of a target molecule and the affinity agent and the melting temperature of a non-target molecule and the affinity agent is highest. In some embodiments, the maximum difference between the melting temperature of a target molecule and the affinity agent and the melting temperature of a non-target molecule and the affinity agent is less than about 9.3° C., in some embodiments less than about 7.8° C., in some embodiments less than about 5.2° C., and in some embodiments less than about 0.7° C.

In some embodiments, the ratio of target molecules to non-target molecules that can be separated by affinity SCODA is any ratio from 1:1 to 1:10,000 and any value therebetween, e.g. 1:100 or 1:1,000. In some embodiments, after conducting affinity SCODA, the ratio of non-target molecules relative to target molecules that is located in a focus spot of the target molecules has been reduced by a factor of up to 10,000 fold.

Example 22

Phase Lag Induced Rotation

In some embodiments, to separate molecules with different affinities for the immobilized affinity agent, a DC bias is superimposed over the SCODA focusing fields as described above. If the separation in binding energy is great enough then the mismatched target can be washed entirely off of the gel. The ability to wash weakly focusing contaminating fragments from the gel can be affected by the phase lag induced rotation discussed above, where the SCODA velocity of a two dimensional system was given by:

$$\vec{v}_{SCODA} = |v_{SCODA}|(\cos(\phi)\hat{r} + \sin(\phi)\hat{\theta}) \qquad (48)$$

where φ is the phase lag between the electric field oscillations and the mobility varying oscillations. Aside from reducing the proportion of the SCODA velocity that contributes to concentration this result has additional implications when washing weakly focusing contaminants out of an affinity matrix. The rotational component will add to the DC bias and can result in zero or low velocity points in the gel that can significantly increase the time required to wash mismatched targets from the gel.

To counteract the effects of a rotational component of motion that may arise in embodiments in which there is a phase lag between the electric field oscillations and the mobility varying oscillations, the direction in which the SCODA focusing fields are applied may be rotated periodically. In some embodiments, the direction in which the SCODA focusing fields are rotated is altered once every period.

Example 23

Optical Feedback

In some embodiments where one molecule of interest (e.g., a target nucleic acid) is concentrated in an affinity matrix while a second, similar, molecule (e.g., the non-target nucleic acid) is washed off of the affinity matrix, optical feedback may be used to determine when washing is complete and/or to avoid running the target out of the affinity matrix.

The two foci of similar molecules may be close together geographically, and optical feedback may be used to ensure the molecule of interest is not washed off the gel. For example, using a fluorescent surrogate for the molecule of interest or the contaminating molecules (or both) one can monitor their respective positions while focusing under bias, and use that geographical information to adjust the bias ensuring that the molecule of interest is pushed as close to the edge of the gel as possible but not off, while the contaminating molecule may be removed from the gel.

In some embodiments, the molecules to be separated are differentially labeled, e.g. with fluorescent tags of a different color. Real-time monitoring using fluorescence detection can be used to determine when the non-target molecule has been washed off of the affinity matrix, or to determine when the foci of the target molecule and the non-target molecule are sufficiently far apart within the affinity matrix to allow both foci to be separately extracted from the affinity matrix.

In some embodiments, fluorescent surrogate molecules that focus similarly to the target and/or non-target molecules may be used to perform optical feedback. By using a fluorescent surrogate for a target molecule, a non-target molecule, or both a target molecule and a non-target molecule, the respective positions of the target molecule and/or the non-target molecule can be monitored while performing affinity focusing under a washing bias. The location of the surrogate molecules within the affinity matrix can be used to adjust the washing bias to ensure that the molecule of interest is pushed as close to the edge of the gel as possible but not off, while the contaminating molecule may be washed off the gel.

In some embodiments, fluorescent surrogate molecules that focus similarly to the target and/or non-target molecules but will not amplify in any subsequent PCR reactions that may be conducted can be added to a sample to be purified. The presence of the fluorescent surrogate molecules within the affinity matrix enables the use of optical feedback to control SCODA focusing conditions in real time. Fluorescence detection can be used to visualize the position of the fluorescent surrogate molecules in the affinity matrix. In embodiments where the fluorescent surrogate mimics the focusing behavior of the target molecule, the applied washing force can be decreased when the fluorescent surrogate approaches the edge of the affinity matrix, to avoid washing the target molecule out of the affinity matrix. In embodiments where the fluorescent surrogate mimics the focusing behavior of the non-target molecule that is to be separated from the target molecule, the applied washing force can be decreased or stopped after the fluorescent surrogate has been washed out of the affinity matrix, or alternatively when the location of the fluorescent surrogate approaches the edge of the affinity matrix.

Example 24

Separation of Differentially Modified Molecules

In some embodiments, molecules that are identical except for the presence or absence of a chemical modification that alters the binding affinity of the molecule for a probe are separated using affinity SCODA. Some embodiments of affinity SCODA are sufficiently sensitive to separate two molecules that have only a small difference in binding affinity for the immobilized affinity agent. Examples of such molecules include differentially modified molecules, such as methylated and unmethylated nucleic acids, methylated or acetylated proteins, or the like.

For example, it has been previously shown that methylation of cytosine residues increases the binding energy of hybridization relative to unmethylated DNA sequences. RNA sequences would be expected to display a similar increase in the binding energy of hybridization when methylated as compared with unmethylated sequences. The inventors have shown that one embodiment of affinity SCODA can be used to separate nucleic acid sequences differing only by the presence of a single methylated cytosine residue. Other chemical modifications would be expected to alter the binding energy of a nucleic acid and its complimentary sequence in a similar manner. Modification of proteins, such as through methylation, can also alter the binding affinity of a protein of interest with a protein, RNA or DNA aptamer, antibody, or other molecule that binds to the protein at or near the methylation site. Accordingly, embodiments of affinity SCODA can be used to separate differentially modified molecules of interest. While the examples herein are directed to methylation enrichment, affinity SCODA can also be applied to enrichment and selection of molecules with other chemical differences, including e.g. acetylation.

Affinity SCODA, and sequence-specific SCODA, may be used to enrich a specific sequence of methylated DNA out of a background of methylated and unmethylated DNA. In this application of affinity SCODA, the strength of the SCODA focusing force may be related to the binding energy of the target DNA to the bound oligonucleotides. Target molecules with a higher binding energy may be made to focus more strongly than targets with lower binding energy. Methylation of DNA has previously been documented to slightly increase the binding energy of target DNA to its complementary sequence. Small changes in binding energy of a complementary oligonucleotide may be exploited through affinity SCODA to preferentially enrich for methylated DNA. SCODA operating conditions may be chosen, for example as described above, such that the methylated DNA is concentrated while unmethylated DNA of the same sequence is washed off the gel.

Some embodiments can separate molecules with a difference in binding energy to an immobilized affinity agent of less than kT, the thermal excitation energy of the target molecules. Some embodiments can separate molecules with a difference in binding energy to an immobilized affinity agent of less than 0.19 kcal/mol. Some embodiments can separate molecules with a difference in binding energy to an immobilized affinity agent of less than 2.6 kcal/mol. Some embodiments can separate molecules with a difference in binding energy to an immobilized affinity agent of less than 3.8 kcal/mol. Some embodiments can separate molecules that differ only by the presence of a methyl group. Some embodiments can separate nucleic acid sequences that differ in sequence at only one base.

Example 25

Applications of Affinity SCODA

Systems and methods for separating, purifying, concentrating and/or detecting differentially modified molecules as described above can be applied in fields where detection of biomarkers, specific nucleotide sequences or differentially modified molecules is important, e.g. epigenetics, fetal DNA detection, pathogen detection, cancer screening and monitoring, detection of organ failure, detection of various disease states, and the like. For example, in some embodiments affinity SCODA is used to separate, purify, concentrate and/or detect differentially methylated DNA in such fields as fetal diagnostic tests utilizing maternal body fluids, pathogen detection in body fluids, and biomarker detection in body fluids for detecting cancer, organ failure, or other disease states and for monitoring the progression or treatment of such conditions.

In some embodiments, a sample of bodily fluid or a tissue sample is obtained from a subject. Cells may be lysed, genomic DNA is sheared, and the sample is subjected to affinity SCODA. In some embodiments, molecules concentrated using affinity SCODA are subjected to further analysis, e.g. DNA sequencing, digital PCR, fluorescence detection, or the like, to assay for the presence of a particular biomarker or nucleotide sequence. In some embodiments, the subject is a human.

It is known that fetal DNA is present in maternal plasma, and that differential methylation of maternal versus fetal DNA obtained from the maternal plasma can be used to screen for genetic disorders (see e.g. Poon et al., 2002, *Clinical Chemistry* 48:1, 35-41). However, one problem that is difficult to overcome is discrimination between fetal and maternal DNA. Affinity SCODA as described above may be used to preferentially separate, purify, concentrate and/or detect DNA which is differentially methylated in fetal DNA versus maternal DNA. For example, affinity SCODA may be used to concentrate or detect DNA which is methylated in the fetal DNA, but not in maternal DNA, or which is methylated in maternal DNA but not fetal DNA. In some embodiments, a sample of maternal plasma is obtained from a subject and subjected to affinity SCODA using an oligonucleotide probe directed to a sequence of interest. The detection of two foci after the application of SCODA focusing fields may indicate the presence of DNA which is differentially methylated as between the subject and the fetus. Comparison to a reference sample from a subject that exhibits a particular genetic disorder may be used to determine if the fetus may be at risk of having the genetic disorder. Further analysis of the sample of DNA obtained through differential modification SCODA through conventional methods such as PCR, DNA sequencing, digital PCR, fluorescence detection, or the like, may be used to assess the risk that the fetus may have a genetic disorder.

One embodiment of the present systems and methods is used to detect abnormalities in fetal DNA, including chromosome copy number abnormalities. Regions of different chromosomes that are known to be differentially methylated in fetal DNA as opposed to maternal DNA are concentrated using affinity SCODA to separate fetal DNA from maternal DNA based on the differential methylation of the fetal DNA in a maternal plasma sample. Further analysis of the separated fetal DNA is conducted (for example using qPCR, DNA sequencing, fluorescent detection, or other suitable method) to count the number of copies from each chromosome and determine copy number abnormalities.

Most cancers are a result of a combination of genetic changes and epigenetic changes, such as changes in DNA methylation (e.g. hypomethylation and/or hypermethylation of certain regions, see e.g. Ehrich, 2002, *Oncogene* 21:35, 5400-5413). Affinity SCODA can be used to separate, purify, concentrate and/or detect DNA sequences of interest to screen for oncogenes which are abnormally methylated. Embodiments of affinity SCODA are used in the detection of biomarkers involving DNA having a different methylation pattern in cancerous or pre-cancerous cells than in healthy cells. Detection of such biomarkers may be useful in both early cancer screening, and in the monitoring of cancer development or treatment progress. In some embodiments, a sample obtained from a subject, e.g. a sample of a bodily fluid such as plasma or a biopsy, may be processed and analyzed by differential modification SCODA using oligonucleotide probes directed to a sequence of interest. The presence of two foci during the application of SCODA fields may indicate the presence of differential methylation at the DNA sequence of interest. Comparison of the sample obtained from the subject with a reference sample (e.g. a sample from a healthy patient and/or a sample known to originate from cancerous or pre-cancerous tissue) can indicate whether the cells of the subject are at risk of being cancerous or pre-cancerous. Further analysis of the sample of DNA obtained through differential modification SCODA through conventional methods such as PCR, DNA sequencing, digital PCR, fluorescence detection, or the like, may be used to assess the risk that the sample includes cells that may be cancerous or pre-cancerous, to assess the progression of a cancer, or to assess the effectiveness of treatment.

In some embodiments, a specific nucleotide sequence is captured in the gel regardless of methylation (i.e. without selecting for a particular methylation status of the nucleic acid). Undesired nucleotide sequences and/or other contaminants may be washed off the gel while the specific nucleotide sequence remains bound by oligonucleotide probes immobilized within the separation medium. Then, differential methylation SCODA is used to focus the methylated version of the sequence while electrically washing the unmethylated sequence toward a buffer chamber or another gel where it can then be recovered. In some embodiments, the unmethylated sequence could be preferentially extracted.

In some embodiments, biomolecules in blood related to disease states or infection are selectively concentrated using affinity SCODA. In some embodiments, the biomolecules are unique nucleic acids with sequence or chemical differences that render them useful biomarkers of disease states or infection. Following such concentration, the biomarkers can be detected using PCR, sequencing, or similar means. In some embodiments, a sample of bodily fluid or tissue is obtained from a subject, cells are lysed, genomic DNA is sheared, and affinity SCODA is performed using oligonucleotide probes that are complimentary to a sequence of interest. Affinity SCODA is used to detect the presence of differentially methylated populations of the nucleic acid sequence of interest. The presence of differentially methylated populations of the target sequence of interest may indicate a likelihood that the subject suffers from a particular disease state or an infection.

In some embodiments, the focusing pattern of the target nucleic acid produced by affinity SCODA from a subject is compared with the focusing pattern of the target nucleic acid produced by affinity SCODA from one or more reference samples (e.g. an equivalent sample obtained from a healthy subject, and/or an equivalent sample obtained from a subject known to be suffering from a particular disease). Similarities between the focusing pattern produced by the sample obtained from the subject and a reference sample obtained from a subject known to be suffering from a particular disease indicate a likelihood that the subject is suffering from the same disease. Differences between the focusing pattern produced from the sample obtained from the subject and a reference sample obtained from a healthy subject indicate a likelihood that the subject may be suffering from a disease. Differences in the focusing pattern produced from the sample obtained from the subject and a reference sample obtained from a healthy subject may indicate the presence of a differential modification or a mutation in the subject as compared with the healthy subject.

Example 26

Use of Multiple Affinity Agents to Capture Multiple Target Molecules

In some embodiments, affinity SCODA is used to separate, purify, concentrate and/or detect more than one sequence per sample. The examples described herein demonstrate that it is possible to concentrate target DNA at probe concentrations as low as 1 µM, as well as with probe concentrations as high as 100 µM. In some embodiments, multiplexed concentration is be performed by immobilizing a plurality of different affinity agents in the medium to provide an affinity matrix. In some embodiments, at least two different affinity agents are immobilized within a medium to separate, purify, concentrate and/or detect at least two different target molecules. In some embodiments, each one of the affinity agents is an oligonucleotide probe with a different sequence. In some embodiments, anywhere between 2 and 100 different oligonucleotide probes are immobilized within a medium to provide an affinity matrix, and anywhere between 2 and 100 different target molecules are separated, purified, concentrated and/or detect simultaneously in a single affinity gel. Each one of the target molecules may be labeled with a different tag to facilitate detection, for example each one of the target molecules could be labeled with a different color of fluorescent tag.

In some embodiments where the binding energy between each of the two or more affinity agents and the two or more target molecules differs, the two or more target molecules may be differentially separated within the affinity matrix by the application of SCODA focusing fields at an appropriate temperature. In some embodiments, a first target molecule with a lower melting temperature for its corresponding affinity agent may be preferentially separated from a second target molecule with a relatively higher melting temperature for its corresponding affinity agent. In some such embodiments, the first molecule is preferentially concentrated by conducting SCODA focusing at a temperature that is sufficiently low that a second target molecule with a relatively higher melting temperature for its corresponding affinity agent does not focus efficiently (i.e. a temperature at which the mobility of the second target molecule within the affinity matrix is relatively low), but sufficiently high to enable efficient focusing of the first molecule. In some such embodiments, the first and second molecules are differentially separated through the application of a washing bias, e.g. a DC bias, at a temperature that is sufficiently low that the second target molecule is not displaced or is displaced only slowly by the washing bias, but sufficiently high that the first target molecule is displaced or is displaced at a higher velocity by the washing bias.

Example 27

Apparatus for Performing Affinity SCODA

In some embodiments, affinity SCODA is performed on an electrophoresis apparatus comprising a region for containing the affinity matrix, buffer reservoirs, power supplies capable of delivering large enough voltages and currents to cause the desired effect, precise temperature control of the SCODA medium (which is a gel in some embodiments), and a two color fluorescence imaging system for the monitoring of two different molecules in the SCODA medium.

Example 28

Affinity SCODA with Single Base Mismatch

To verify the predicted temperature dependent mobility expressed in equation (36), experiments were performed to measure the response of target DNA velocity to changes in temperature. Initial experiments were done with 100 nucleotide oligonucleotides as target DNA. Oligonucleotides are single stranded so do not need to be denatured to interact with the affinity gel. The oligonucleotides are also sufficiently short that they have a negligible field dependent mobility. Longer nucleic acid molecules, e.g. greater than about 1000 nucleotides in length, may be difficult to separate based on sequence, as longer molecules have a tendency to focus in a non-sequence-specific manner from the electrophoretic SCODA effect in embodiments using Joule heating provided by an electric field to provide the temperature gradient.

To perform these measurements a polyacrylamide gel (4% T, 2% C) in 1×TB (89 mM tris, 89 mM boric acid) with 0.2 M NaCl and 10 µM acrydite probe (SEQ ID NO.:1) oligo was cast in a one dimensional gel cassette containing only two access ports. Polymerization was initiated through the addition of 2 µl of 10% w/v APS and 0.2 µl TEMED per ml of gel.

Mobility measurements were performed on two different 100 nucleotide oligonucleotides differing by a single base containing sequences with a perfect match (PM) (SEQ ID NO.:2) to the probe and a single base mismatch (sbMM) (SEQ ID NO.:3). These target oligonucleotides were end labeled with either 6-FAM or Cy5 (IDT DNA). Probe and target sequences used for these experiments are shown in Table 4. The regions of the PM and sbMM target oligonucleotides that are complementary to the immobilized probe are shown in darker typeface than the other portions of these oligonucleotides. The position of the single base mismatch is underlined in the sbMM target sequence.

TABLE 4

Probe and target oligonucleotide sequences used for sequence specific SCODA.

| | Sequence |
|---|---|
| Probe (SEQ ID NO.: 1) | 5' ACT GGC CGT CGT TTT ACT 3' |
| PM Target (SEQ ID NO.: 2) | 5' CGA TTA AGT TGA GTA ACG CCA CTA TTT TCA CAG TCA TAA CCA TGT AAA ACG ACG GCC AGT GAA TTA GCG ATG CAT ACC TTG GGA TCC TCT AGA ATG TAC C 3' |
| sbMM Target (SEQ ID NO.: 3) | 5' CGA TTA AGT TGA GTA ACG CCA CTA TTT TCA CAG TCA TAA CCA TGT AAA ACT ACG GCC AGT GAA TTA GCG ATG CAT ACC TTG GGA TCC TCT AGA ATG TAC C 3' |

The probe sequence was chosen to be complementary to pUC19 for subsequent experiments with longer targets, discussed below. The 100 nucleotide targets contain a sequence complementary to the probe (perfect match: PM) or with a single base mismatch (sbMM) to the probe with flanking sequences to make up the 100 nucleotide length. The flanking sequences were designed to minimize the effects of secondary structure and self-hybridization. Initial sequences for the regions flanking the probe binding site were chosen at random. Folding and self-hybridization energies were then calculated using MFOLD (M. Zuker, "Mfold web server for nucleic acid folding and hybridization prediction,". *Nucleic Acids Res.* 31 (13), 3406-3415, 2003, incorporated herein by reference), and the sequences were altered one base at a time to minimize these effects ensuring that the dominant interactions would be between target strands and the probe.

Table 5 shows the binding energies and melting temperatures for the sequences shown in Table 4 calculated using MFOLD. The binding energy, $\Delta G$, is given as $\Delta H - T\Delta S$, where $\Delta H$ is the enthalpy and $\Delta S$ the entropy in units of kcal/mol and kcal/mol K respectively. The following parameter values were used for calculation of the values in Table 5: temperature=50° C., $[Na^+]$=0.2 M, $[Mg^{2+}]$=0 M, strand concentration=10 μM. The largest $T_m$ for non-probe-target hybridization is 23.9° C. and the greatest secondary structure $T_m$ is 38.1° C. Both of these values are far enough below the sbMM target-probe $T_m$ that they are not expected to interfere target-probe interactions.

TABLE 5

Binding energies and melting temperatures for Table 4 sequences.

| | Probe (SEQ ID NO.: 1) | PM Target (SEQ ID NO.: 2) | sbMM Target (SEQ ID NO.: 3) | Secondary Structure |
|---|---|---|---|---|
| Probe (SEQ ID NO.: 1) | −35.4 + 0.1012 * T $T_m$ = 12.2° C. | −145.3 + 0.4039 * T $T_m$ = 65.1° C. | −126.8 + 0.3598 * T $T_m$ = 55.8° C. | −20.3 + 0.07049 * T $T_m$ = 14.8° C. |
| PM Target (SEQ ID NO.: 2) | −145.3 + 0.4039 * T $T_m$ = 65.1° C. | −40.2 + 0.1124 * T $T_m$ = 23.9° C. | −40.2 + 0.1111 * T $T_m$ = 20.9° C. | −24.3 + 0.07808 * T $T_m$ = 38.1° C. |
| sbMM Target (SEQ ID NO.: 3) | −126.8 + 0.3598 * T $T_m$ = 55.8° C. | −40.2 + 0.1111 * T $T_m$ = 20.9° C. | −40.2 + 0.1124 * T $T_m$ = 23.9° C. | −24.3 + 0.07808 * T $T_m$ = 38.1° C. |

To measure the velocity response as a function of temperature the fluorescently labeled target was first injected into the gel at high temperature (70° C.), and driven under a constant electric field into the imaging area of the gel. Once the injected band was visible the temperature of the spreader plate was dropped to 55° C. An electric field of 25 V/cm was applied to the gel cassette while the temperature was ramped from 40° C. to 70° C. at a rate of 0.5° C./min. Images of the gel were taken every 20 sec. Image processing software written in LABVIEW® (National Instruments, Austin Tex.) was used to determine the location of the center of the band in each image and this position data was then used to calculate velocity.

Figure 25:
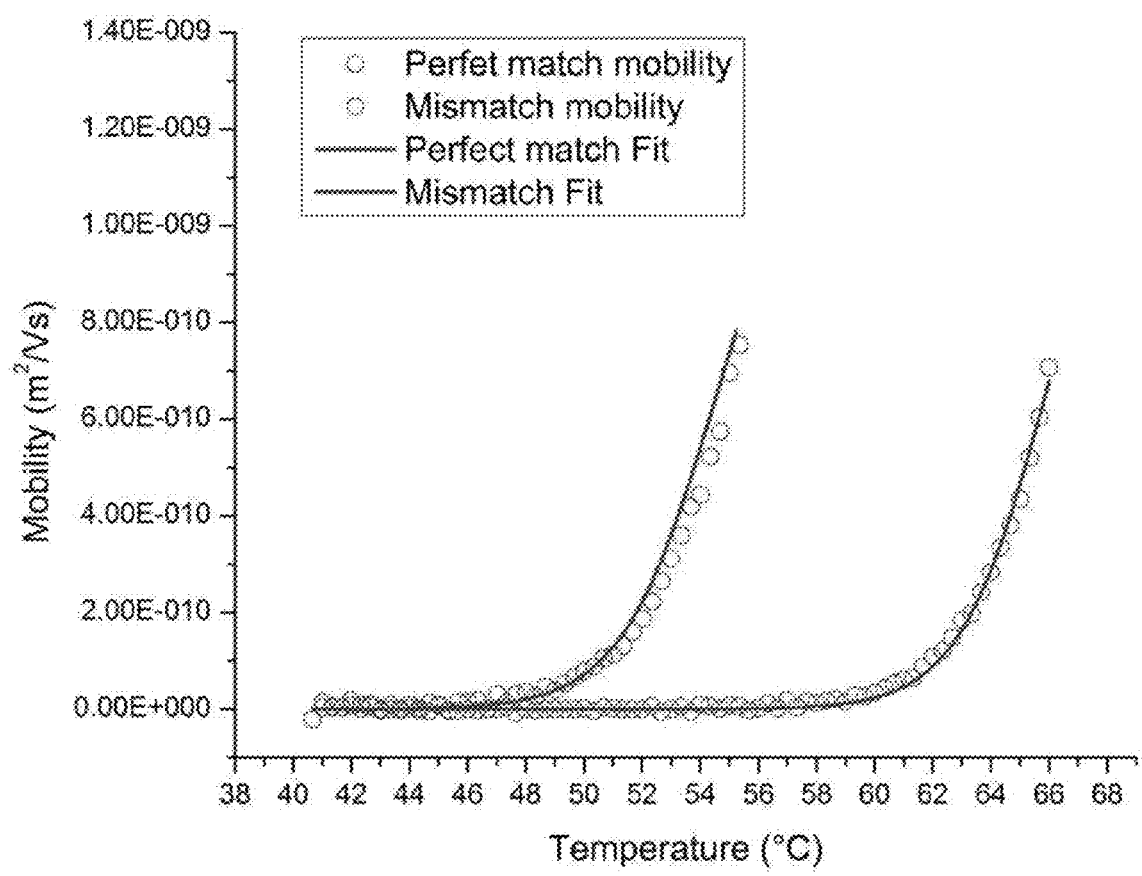
FIG. 25 shows the results of the measurement of temperature dependence of DNA target mobility through a gel containing immobilized complementary oligonucleotide probes for one exemplary separation.

FIG. 25 shows a plot of target DNA mobility as a function of temperature. Using the values for the probe and target sequences shown in Table 5, the velocity versus temperature curves were fit to equation (36) to determine the two free parameters: the mobility $\mu_0$, and β a constant that depends on the kinetics of the hybridization reaction.

A fit of the data shown in FIG. 25 shows good agreement with the theory of migration presented above. Data for the mismatch mobility are shown as the curve on the left, and data for the perfect match mobility are shown as the curve on the right. The $R^2$ value for the PM fit and MM fits were 0.99551 and 0.99539 respectively. The separation between the perfect match and single base mismatch targets supports that there is an operating temperature where the focusing speed of the perfect match target is significantly greater than that of the mismatched target enabling separation of the two species through application of a DC bias field as illustrated in FIG. 18.

Example 29

Selective Separation of Molecules Using Affinity SCODA

A 4% polyacrylamide gel containing 10 μM acrydite modified probe oligos (Integrated DNA Technologies, www.idtdna.com) was cast in a gel cassette to provide an affinity matrix. Equimolar amounts of the perfect match and single base mismatch targets were injected into the affinity gel at 30° C. with an electric field of 100 V/cm applied across the gel such that both target molecules would be initially captured and immobilized at the gel buffer interface. The temperature was then increased to 70° C. and a constant electric field of 20 V/cm applied to the gel to move the target into the imaging area of the gel. The temperature was then dropped to 62° C. and a 108 V/cm SCODA focusing field superimposed over an 8 V/cm DC bias as shown in Table 6 was applied to the four source electrodes with a period of 5 seconds. The rotation direction of the SCODA focusing field was altered every period.

TABLE 6

Focusing plus bias potentials applied.

| | Electrode A | Electrode B | Electrode C | Electrode D |
|---|---|---|---|---|
| Step 1 | −108 | 4 | 8 | 4 |
| Step 2 | 0 | −104 | 8 | 4 |
| Step 3 | 0 | 4 | −100 | 4 |
| Step 4 | 0 | 4 | 8 | −104 |

Figure 26:
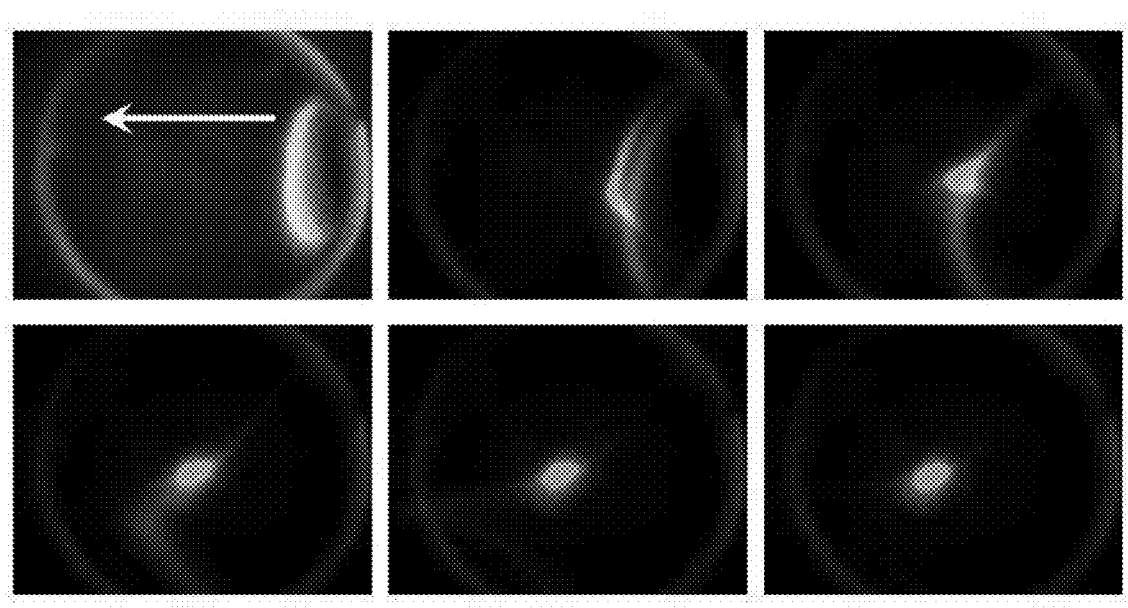
FIG. 26 shows a time series of affinity SCODA focusing under the application of DC bias according to one embodiment. Perfect match DNA is tagged with 6-FAM (green) (leading bright line that focuses to a tight spot) and single base mismatch DNA is tagged with Cy5 (red) (trailing bright line that is washed from the gel). Images taken at 3 minute intervals. The first image was taken immediately following injection.

FIG. 26 shows images of concentration taken every 2 minutes. The perfect match target was tagged with 6-FAM and shown in green (leading bright spot which focuses to a tight spot), the mismatch target was tagged with Cy5 and is shown in red (trailing bright line that is washed from the gel). The camera gain was reduced on the green channel after the first image was taken. DNA was injected into the right side of the gel and focusing plus bias fields were applied. The perfect match target (green) experiences a drift velocity similar to that shown in FIG. 24A and moves towards a central focus location. The more weakly focusing mismatch target (red) experiences a velocity field similar to that shown in FIG. 24B and is pushed off the edge of the gel by the bias field. The direction of application of the applied washing field is indicated by the white arrow.

This experiment verifies the predictions of FIGS. 24A and 24B demonstrating that it is possible to generate two different velocity profiles for two DNA targets differing by only a single base enabling preferential focusing of the target with the higher binding energy to the gel. The images in FIG. 26 confirm that there are two distinct velocity profiles generated for the two different sequences of target DNA moving through an affinity matrix under the application of both a SCODA focusing field and a DC bias. A dispersive velocity field is generated for the single base mismatch target and a non-dispersive velocity field is generated for the perfect match target. This example demonstrates that it is possible to efficiently enrich for targets with single base specificity, and optionally wash a non-desired target off of an affinity matrix, even if there is a large excess of mismatch target in the sample.

Example 30

Optimization of Operating Conditions

Different parameters of the SCODA process may be optimized to achieve good sample enrichment at reasonable yields. In embodiments having immobilized (and negatively charged) DNA in the gel, a relatively high salinity running buffer was found to provide both efficient and stable focusing, as well as minimizing the time required to electrokinetically inject target DNA from an adjacent sample chamber into the SCODA gel.

Example 31

Optimization of Buffer Salinity

Early attempts of measuring the temperature dependent mobility of molecules in an affinity gel as well as the first demonstrations of sequence specific SCODA were performed in buffers used for electrophoretic SCODA. These are typically standard electrophoresis buffers such as tris-borate EDTA (TBE), often diluted 4 to 6 fold to reduce the gel conductivity, enabling the application of high electric fields within thermal limitations imposed by Joule heating, resulting in shorter concentration times. Although it is possible to achieve sequence specific SCODA based concentration in a 1×TBE buffer (89 mM tris, 89 mM boric acid, 2 mM disodium EDTA), conditions can be further optimized for performance of sequence specific SCODA due to the relatively low concentration of dissociated ions at equilibrium in 1×TBE buffer. A low concentration of dissociated ions results in slow hybridization kinetics, exacerbates ionic depletion associated with immobilizing charges (oligonucleotide probes) in the gel, and increases the time required to electrokinetically inject target DNA into the gel. Calculations using 89 mM tris base and 89 mM boric acid, with a pKa of 9.24 for boric acid and a pKa of 8.3 for tris shows a concentration of 1.49 mM each of dissociated tris and dissociated boric acid in 1×TBE buffer.

Example 32

Effect of Salt Concentration on DNA Hybridization

In embodiments used to separate nucleic acids, the presence of positive counter ions shields the electrostatic repulsion of negatively charged complementary strands of nucleic acid, resulting in increased rates of hybridization. For example, it is known that increasing the concentration of $Na^+$ ions affects the rate of DNA hybridization in a non-linear manner. The hybridization rate increases by about 10 fold when [NaCl] is increased from 10 mM to 1 M of [NaCl], with most of the gain achieved by the time one reaches about 200 mM. At low concentrations of positive counter ions, below about 10 mM, the rate of hybridization is more strongly dependent on salt concentration, roughly proportional to the cube of the salt concentration. Theoretical calculations suggest that the total positive counter ion concentration of 1×TBE is around 5.5 mM (1.5 mM of dissociated tris, and 4 mM of $Na^+$ from the disodium EDTA). At this ion concentration it was possible to achieve focusing however the slow hybridization rates resulted in weak focusing and large final focus spot sizes.

A slow rate of hybridization can lead to weak focusing through an increase in the phase lag between the changes in electric field and changes in mobility. Equation (43) describes the SCODA velocity as being proportional to $\cos(\phi)$, where $\phi$ represents the phase lag between the mobility oscillations and the electric field oscillations. In the case of ssSCODA a phase lag can result from both a slow thermal response as well as from slow hybridization kinetics.

This phase lag results in slower focusing times and larger spot sizes since the final spot size is a balance between the inward SCODA-driven drift, and outward diffusion-driven drift. Faster focusing times are always desirable as this tends to reduce the overall time to enrich a target from a complex mixture. A smaller spot size is also desirable as it improves the ability to discriminate between different molecular species. As discussed above, when performing SCODA focusing under application of a DC bias, the final focus spot will be shifted off center by an amount that depends on both the mobility of the target and the speed of focusing, both of which depend on the strength of the interaction between the target and the gel bound probes. The amount of separation required to discriminate between two similar molecules when focusing under bias therefore depends on the final focus spot diameter. Smaller spot diameters should improve the ability to discriminate between two targets with similar affinity to the gel bound probes.

At the low rates of hybridization achieved with 1×TBE buffer, reliable focusing was only achievable with probe concentrations near 100 µM. Increasing the salt concentration from around 5 mM to 200 mM through the addition of NaCl, while keeping the probe concentration at 100 µM had the effect of reducing the final focus spot size as shown in FIGS. 27A-D. All images in FIGS. 27A-D were taken after a similar amount of focusing time (approximately 5 min), however the increased salinity resulted in increased Joule heating, which required a four fold reduction of field strength to prevent boiling when focusing with 200 mM NaCl. Probe concentrations are 100 µM, 10 µM, 1 µM, and 100 µM, respectively in FIGS. 27A, 27B, 27C, and 27D. The buffer used in FIGS. 27A, 27B, and 27C was 1×TB with 0.2 M NaCl. The buffer used in FIG. 27D was 1×TBE. Focusing was not reliable at 10 µM and 1 µM probe in 1×TBE and these results are not shown. Under equivalent conditions in this example, addition of 200 mM NaCl to the gel also allowed for focusing of complementary targets at 100 fold lower probe concentrations.

Equation (43) states that the focusing speed is proportional to the electric field strength, so that fact that comparable focusing times are achieved with a four-fold reduction in electric field strength suggests that the field normalized focusing speed is considerably faster under high salinity conditions.

Although the total time for focusing was not reduced by the addition of 200 mM NaCl, focusing at lower electric field strength may be desirable in some embodiments because lower field strength can limit the degree of non-specific electrophoretic SCODA that may occur in an affinity matrix in some embodiments. For example, all target nucleic acid molecules will focus irrespective of their sequence in the affinity gels used for sequence specific SCODA in embodiments where the thermal gradient is established by an electric field due to electrophoretic SCODA. The speed of electrophoretic SCODA focusing increases with electric field, so decreasing the field strength will have the effect of reducing the non-specific SCODA focusing speed, allowing one to wash non-target DNA molecules from the gel more easily by applying a DC bias.

Example 33

Ion Depletion and Bound Charges

The rate at which ions are depleted (or accumulated) at a boundary increases as the fraction of charges that are immobile increases. The 100 μM probe concentration required to achieve efficient concentration in 1×TBE results in 2 mM of bound negative charges within the gel when a 20 nucleotide probe is used, which is comparable to the total amount of dissolved negative ions within the gel (around 5.5 mM). This high proportion of bound charge can result in the formation of regions within the gel that become depleted of ions when a constant electric field is placed across the gel as it is during injection and during SCODA focusing under DC bias.

A high salinity running buffer can therefore help to minimize many of the ion depletion problems associated with immobilizing charges in an ssSCODA gel by enabling focusing at lower probe concentrations, as well as reducing the fraction of bound charges by adding additional free charges.

Example 34

Denaturation of Double Stranded DNA

Target DNA will not interact with the gel immobilized probes unless it is single stranded. The simplest method for generating single stranded DNA from double stranded DNA is to boil samples prior to injection. One potential problem with this method is that samples can re-anneal prior to injection reducing the yield of the process, as the re-annealed double stranded targets will not interact with the probes and can be washed off of the gel by the bias field. Theoretical calculations show that the rate of renaturation of a sample will be proportional to the concentration of denatured single stranded DNA. Provided target concentration and sample salinity are both kept low, renaturation of the sample can be minimized.

To measure the effect of target concentration on renaturation and overall efficiency, fluorescently labeled double stranded PCR amplicons complementary to gel bound probes were diluted into a 250 μL volume containing about 2 mM NaCl and denatured by boiling for 5 min followed by cooling in an ice bath for 5 min. The sample was then placed in the sample chamber of a gel cassette, injected into a focusing gel and concentrated to the center of the gel. After concentration was complete the fluorescence of the final focus spot was measured, and compared to the fluorescence of the same quantity of target that was manually pipetted into the center of an empty gel cassette. This experiment was performed with 100 ng ($2 \times 10^{11}$ copies) and 10 ng ($2 \times 10^{10}$ copies) of double stranded PCR amplicons. The 100 ng sample resulted in a yield of 40% and the 10 ng sample resulted in a yield of 80%. This example confirms that lower sample DNA concentration will result in higher yields.

Example 35

Phase Lag Induced Rotation

Figure 28:
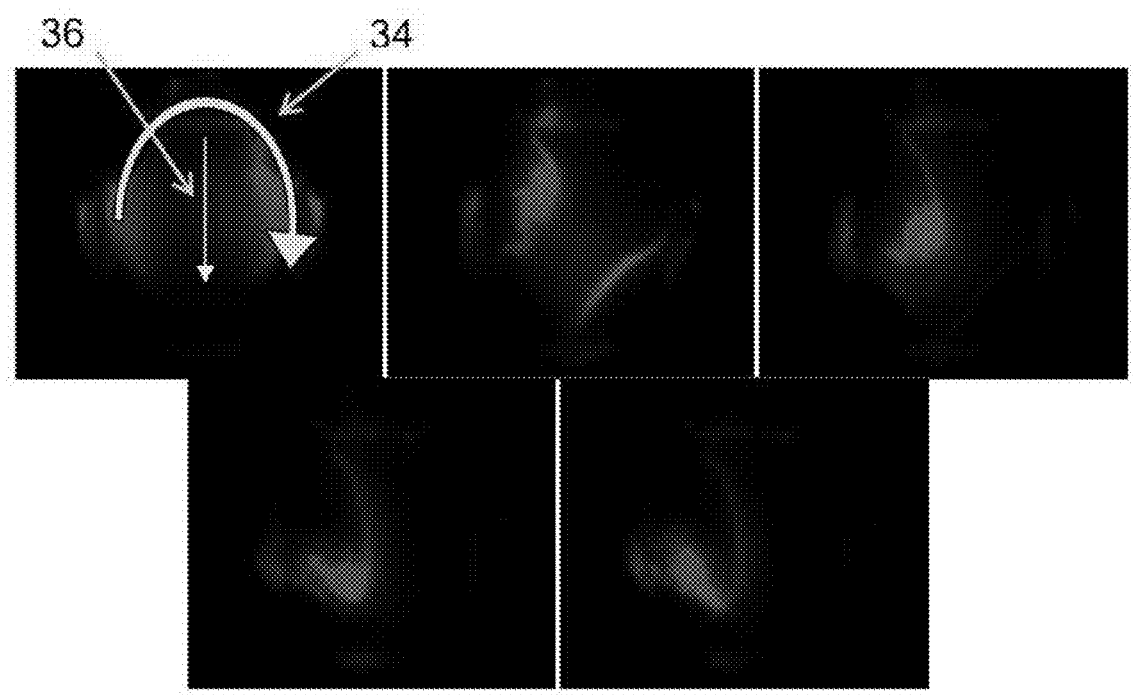
FIG. 28 shows an experiment providing an example of phase lag induced rotations. The field rotation is counter-clockwise. It induces a clockwise rotation of the targets in the gel. Images were taken at 5 minute intervals.

As discussed above, in embodiments in which there is a phase lag between the electric field oscillations and the mobility varying oscillations, a rotational component will be added to the velocity of molecules moving through the affinity matrix. An example of this problem is shown in FIG. 28. The targets shown in FIG. 28 focus weakly under SCODA fields and when a small bias is applied to wash them from the gel; the wash field and the rotational velocity induced by the SCODA fields sum to zero near the bottom left corner of the gel. This results in long wash times, and in extreme cases weak trapping of the contaminant fragments. The direction of rotation of the electric field used to produce SCODA focusing is indicated by arrow 34. The direction of the applied washing force is indicated by arrow 36.

To overcome this problem the direction of the field rotation can be altered periodically. In other examples described herein, the direction of the field rotation was altered every period. This results in much cleaner washing and focusing with minimal dead zones. This scheme was applied during focus and wash demonstrations described above and shown in FIG. 26, an example in which the mismatched target was cleanly washed from the gel without rotation. Under these conditions there is a reduced SCODA focusing velocity due to the phase lag, but there is not an additional rotational component of the SCODA velocity.

Example 36

Effect of Secondary Structure

Secondary structure in the target DNA will decrease the rate of hybridization of the target to the immobilized probes. This will have the effect of reducing the focusing speed by increasing the phase lag described in equation (43). The amount by which secondary structure decreases the hybridization rate depends on the details of the secondary structure. With a simple hairpin for example, both the length of the stem and the loop affect the hybridization rate. For most practical applications of sequence specific SCODA, where one desires to enrich for a target molecule differing by a single base from contaminating background DNA, both target and background will have similar secondary structure. In this case the ability to discriminate between target and background will not be affected, only the overall process time. By increasing the immobilized probe concentration and the electric field rotation period one can compensate for the reduced hybridization rate.

There are potentially cases where secondary structure can have an impact on the ability to discriminate a target molecule from background molecules. It is possible for a single base difference between target and background to affect the secondary structure in such a way that background DNA has reduced secondary structure and increased hybridization rates compared to the target, and is the basis for single stranded conformation polymorphism (SSCP) mutation analysis. This effect has the potential to both reduce or enhance the ability to successfully enrich for target DNA, and care must be taken when designing target and probe sequences to minimize the effects of secondary structure. Once a target molecule has been chosen, the probe position can be moved around the mutation site. The length of the probe molecule can be adjusted. In some cases, oligonucleotides can be hybridized to sequences flanking the region where the probe anneals to further suppress secondary structure.

Example 37

Quantitation of Sequence Specific SCODA Performance

The length dependence of the final focus location while focusing under DC bias was measured and shown to be independent of length for fragments ranging from 200 nt to 1000 nt in length; an important result, which implies that ssSCODA is capable of distinguishing nucleic acid targets by sequence alone without the need for ensuring that all targets are of a similar length. Measurements confirmed the ability to enrich for target sequences while rejecting contaminating sequences differing from the target by only a single base, and the ability to enrich for target DNA that differs only by a single methylated cytosine residue with respect to contaminating background DNA molecules.

Example 38

Length Independence of Focusing

The ability to purify nucleic acids based on sequence alone, irrespective of fragment length, eliminates the need to ensure that all target fragments are of similar length prior to enrichment. The theory of sequence specific SCODA presented above predicts that sequence specific SCODA enrichment should be independent of target length. However, effects not modeled above may lead to length dependence, and experiments were therefore performed to confirm the length independence of sequence specific SCODA.

According to the theory of thermally driven sequence specific SCODA developed above, the final focus location under bias should not depend on the length of the target strands. Length dependence of the final focus location enters into this expression through the length dependence of the unimpeded mobility of the target $\mu_0$. However, since both $\mu(T_m)$ and $\alpha$ are proportional to $\mu_0$, the length dependence will cancel from this expression. The final focus location of a target concentrated with thermally driven ssSCODA should therefore not depend on the length of the target, even if a bias is present.

There are two potential sources of length dependence in the final focus location, not modeled above, which must also be considered: electrophoretic SCODA in embodiments where the temperature gradient is established by an electric field, and force based dissociation of probe target duplexes. DNA targets of sufficient length (>200 nucleotides) have a field dependent mobility in the polyacrylamide gels used for sequence specific SCODA, and will therefore experience a sequence independent focusing force when focusing fields are applied to the gel. The total focusing force experienced by a target molecule will therefore be the sum of the contributions from electrophoretic SCODA and sequence specific SCODA. Under electrophoretic SCODA, the focusing velocity tends to increase for longer molecules, while the DC velocity tends to decrease so that under bias the final focus location depends on length. The second potential source of length dependence in the final focus location is force based dissociation. The theory of affinity SCODA presented above assumed that probe-target dissociation was driven exclusively by thermal excitations. However it is possible to dissociate double stranded DNA with an applied force. Specifically, an external electric field pulling on the charged backbone of the target strand can be used to dissociate the probe-target duplex. The applied electric field will tend to reduce the free energy term $\Delta G$ in equation (35) by an amount equal to the energy gained by the charged molecule moving through the electric field. This force will be proportional to the length of the target DNA as there will be more charges present for the electric field to pull on for longer target molecules, so for a given electric field strength the rate of dissociation should increase with the length of the target.

Figure 29A:
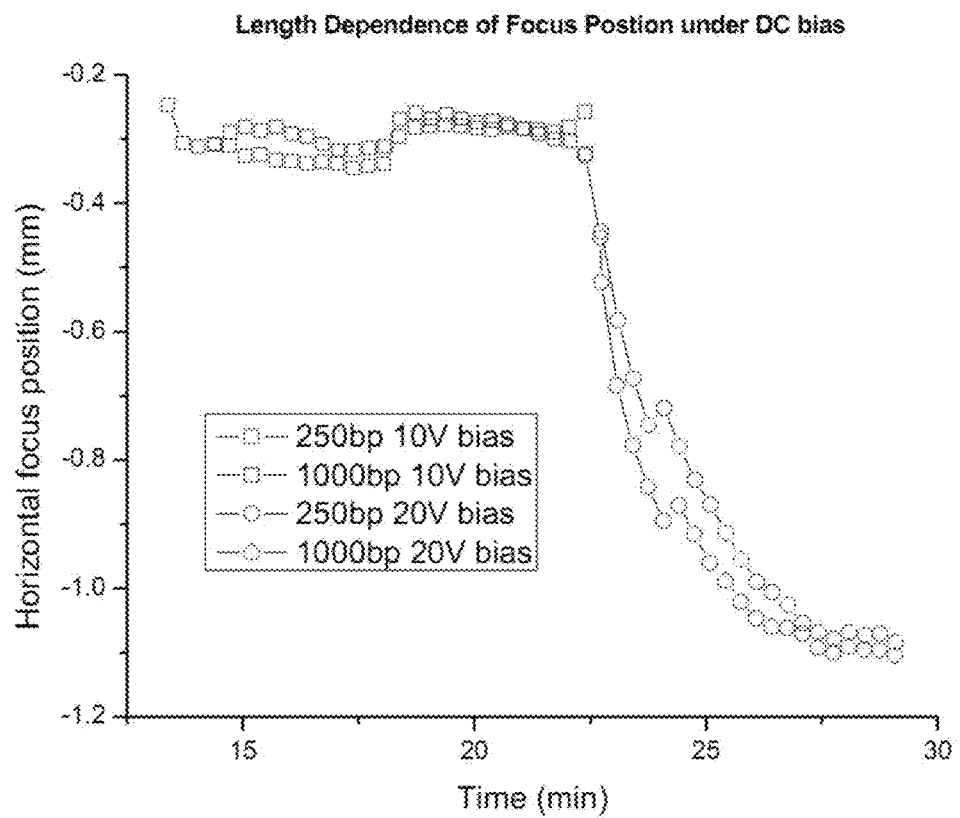
FIG. 29A shows the focus location under bias for 250 bp and 1000 bp fragments labeled with different fluorescent markers, with squares indicating data for the application of a 10 V DC bias and circles indicating data for the application of a 20 V DC bias.
Figure 29B:
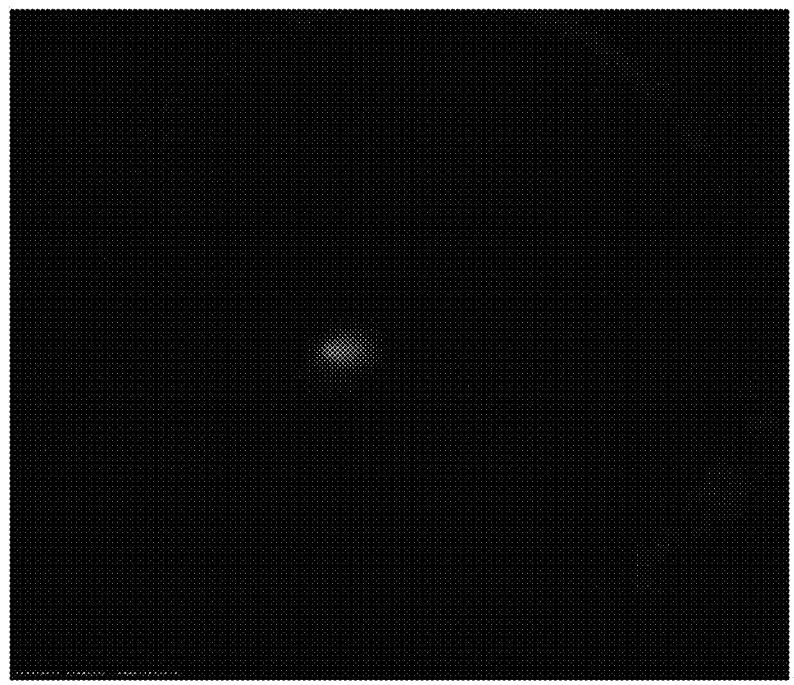
FIG. 29B shows an image of the affinity gel at the end of the run, wherein images showing the location of each fluorescent marker have been superimposed.

To measure whether or not these two effects contribute significantly to the length dependence of the final focus location, two different lengths of target DNA, each containing a sequence complementary to gel immobilized probes, were focused under bias and the final focus location measured and compared. The target DNA was created by PCR amplification of a region of pUC19 that contains a sequence complementary to the probe sequence in Table 4. Two reactions were performed with a common forward primer, and reverse primers were chosen to generate a 250 bp amplicon and a 1000 bp amplicon. The forward primers were fluorescently labeled with 6-FAM and Cy5 for the 250 bp and 1000 bp fragments respectively. The targets were injected into an affinity gel and focused to the center before applying a bias field. A bias field of 10 V/cm was superimposed over 120 V/cm focusing fields for 10 min at which point the bias was increased to 20 V/cm for an additional 7 min. Images of the gel were taken every 20 sec, with a 1 sec delay between the 6-FAM channel and the Cy5 channel. The field rotation period was 5 sec. Images were post processed to determine the focus location of each fragment. FIGS. 29A and 29B show the focus location versus time for the 250 bp (green) and 1000 bp (red) fragments. FIG. 29B is an image of final focus of the two fragments at the end of the experiment.

There is a small difference in final location that can be attributed to the fact that the two images were not taken at the same phase in the SCODA cycle. This example shows that the final focus position does not depend on length. Thus, under these operating conditions electrophoretic SCODA focusing is much weaker than affinity SCODA focusing, and that affinity SCODA is driven largely by thermal dissociation rather than force-based dissociation. This result confirms that affinity SCODA is capable of distinguishing nucleic acid targets by sequence alone without the need for ensuring that all targets are of a similar length.

Example 39

Single Base Mismatch Resection Ratio

To demonstrate the specificity of ssSCODA with respect to rejection of sequences differing by a single base, different ratios of synthetic 100 nt target DNA containing either a perfect match (PM) or single base mismatch (sbMM) to a gel bound probe, were injected into an affinity gel. SCODA focusing in the presence of DC wash fields was performed to remove the excess sbMM DNA. The PM target sequence was labeled with 6-FAM and the sbMM with Cy5; after washing the sbMM target from the gel the amount of fluorescence at the focus location was quantified for each dye and compared to a calibration run. For the calibration run, equimolar amounts of 6-FAM labeled PM and Cy5 labeled PM target DNA were focused to the center of the gel and the fluorescence signal at the focus location was quantified on each channel. The ratio of the signal Cy5 channel to the signal on the 6-FAM channel measured during this calibration is therefore the signal ratio when the two dye molecules are present in equimolar concentrations. By comparing the fluorescence ratios after washing excess sbMM from the gel to the calibration run it was possible to determine the amount of sbMM DNA rejected from the gel by washing.

Samples containing target sequences shown in Table 4 were added to the sample chamber and an electric field of 50 V/cm was applied across the sample chamber at 45° C. to inject the sample into a gel containing 10 μM of immobilized probe. Once the sample was injected into the gel, the liquid in the sample chamber was replaced with clean buffer and SCODA focusing was performed with a superimposed DC wash field. A focusing field of 60 V/cm was combined with a DC wash field of 7 V/cm, the latter applied in the direction opposite to the injection field. It was found that this direction for the wash field led to complete rejection of the mismatched target DNA in the shortest amount of time. Table 7 below shows the amount of DNA injected into the gel for each experiment.

TABLE 7

List of targets run for measuring the rejection ratio of affinity SCODA with respect to single base differences.

| Run Description: | Cy5 Labeled Target | 6-FAM Labeled Target |
|---|---|---|
| 1:1 Calibration | 10 fmol PM | 10 fmol PM |
| 100:1 | 1 pmol sbMM | 10 fmol PM |
| 1,000:1 | 10 pmol sbMM | 10 fmol PM |
| 10,000:1 | 100 pmol sbMM | 10 fmol PM |
| 100,000:1 | 1 nmol sbMM | 10 fmol PM |

Figure 30A:
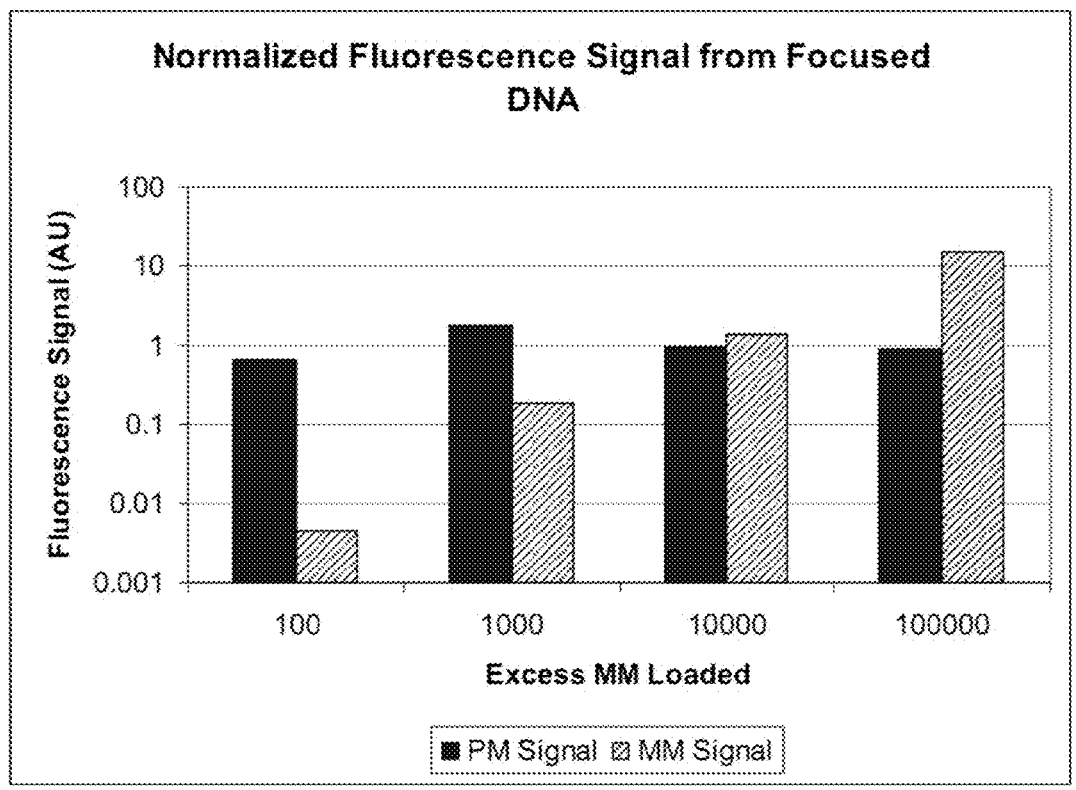
FIGS. 30A and 30B show respectively the normalized fluorescence signal and the calculated rejection ratio of a 100 nucleotide sequence having a single base mismatch as compared with a target DNA molecule according to one example.
Figure 30B:
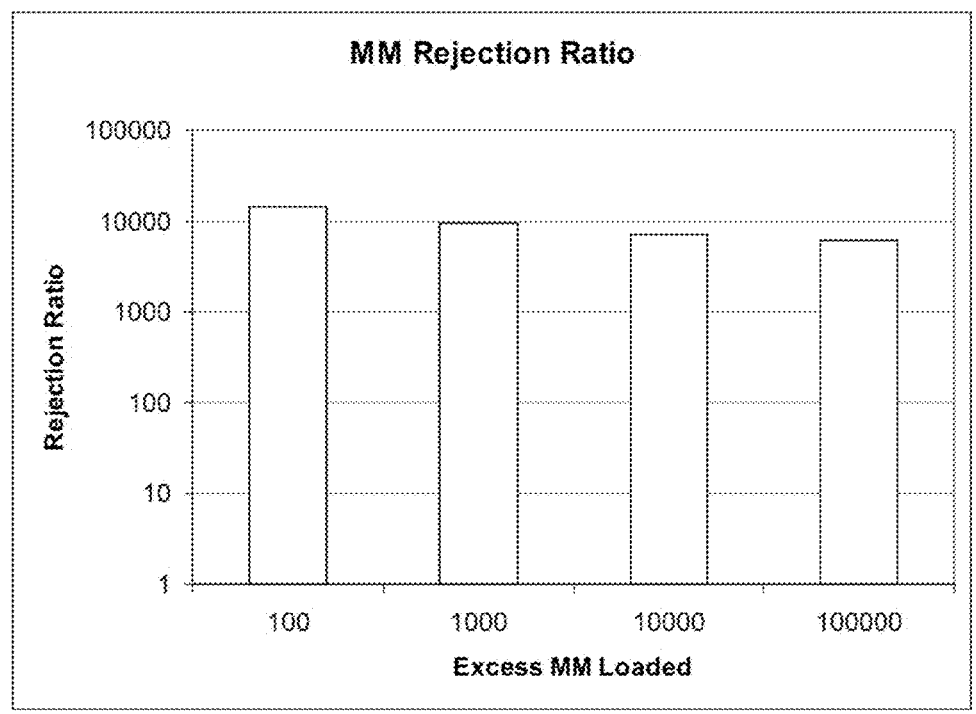

After the mismatched target had been washed from the gel, the focusing fields were turned off and the temperature of the gel was reduced to 25° C. prior to taking an image of the gel for quantification. It was important to ensure that all images used for quantification were taken at the same temperature, since Cy5 fluorescence is highly temperature dependent, with the fluorescence decreasing at higher temperatures. The ratio of fluorescence on the Cy5 and 6-FAM channels were compared to the 1:1 calibration run to determine the rejection ratio for each run. FIGS. 30A and 30B show the results of these experiments. Four different ratios of sbMM:PM were injected into a gel and focused under bias to remove excess sbMM. The PM DNA was tagged with 6-FAM and the sbMM DNA was tagged with Cy5. FIG. 30A shows the fluorescence signal from the final focus spot after excess sbMM DNA had been washed from the gel. The fluorescence signals are normalized to the fluorescence measured on an initial calibration run where a 1:1 ratio of PM 6-FAM:PMCy5 DNA was injected and focused to the center of the gel. FIG. 30B shows the rejection ratios calculated by dividing the initial ratio of sbMM:PM by the final ratio after washing.

It was found that rejection ratios of about 10,000 fold are achievable. However it should be noted that images taken during focusing and wash at high sbMM:PM ratios suggest that there were sbMM molecules with two distinct velocity profiles. Most of the mismatch target washed cleanly off of the gel while a small amount was captured at the focus. These final focus spots visible on the Cy5 channel likely consisted of Cy5 labeled targets that were incorrectly synthesized with the single base substitution error that gave them the PM sequence. The 10,000:1 rejection ratio measured here corresponds to estimates of oligonucleotide synthesis error rates with respect to single base substitutions, meaning that the mismatch molecule synthesized by the oligonucleotide manufacturer likely contains approximately 1 part in 10,000 perfect match molecules. This implies that the residual fluorescence detected on the Cy5 channel, rather than being unresolved mismatch may in fact be Cy5 labeled perfect match that has been enriched from the mismatch sample. Consequently the rejection ratio of ssSCODA may actually be higher than 10,000:1.

Example 40

Mutation Enrichment for Clinically Relevant Mutation

The synthetic oligonucleotides used in the example above were purposely designed to maximize the difference in binding energy between the perfect match-probe duplex and the mismatch-probe duplex. The ability of affinity SCODA to enrich for biologically relevant sequences has also been demonstrated. In this example, cDNA was isolated from cell lines that contained either a wild type version of the EZH2 gene or a Y641N mutant, which has previously been shown to be implicated in B-cell non Hodgkin Lymphoma. 460 bp regions of the EZH2 cDNA that contained the mutation site were PCR amplified using fluorescent primers in order to generate fluorescently-tagged target molecules that could be visualized during concentration and washing. The difference in binding energy between the mutant-probe duplex and the wild type-probe duplex at 60° C. was 2.6 kcal/mol compared to 3.8 kcal/mol for the synthetic oligonucleotides used in the previous examples. This corresponds to a melting temperature difference of 5.2° C. for the mutant compared to the wild type. Table 8 shows the free energy of hybridization and melting temperature for the wild type and mutants to the probe sequence.

TABLE 8

Binding energy and melting temperatures of EZH2 targets to the gel bound probe.

| Target | Binding Energy |
|---|---|
| Wild Type | −161.9 + 0.4646T |
|  | $T_m = 57.1°$ C. |
| Y641N Mutant | −175.2 + 0.4966T |
|  | $T_m = 62.3°$ C. |

A 1:1 mixture of the two alleles were mixed together and separated with affinity SCODA. 30 ng of each target amplicon was added to 300 μl of 0.01 mM sequence specific SCODA running buffer. The target solution was immersed in a boiling water bath for 5 min then placed in an ice bath for 5 min prior to loading onto the gel cassette in order to denature the double stranded targets. The sample was injected with an injection current of 4 mA for 7 min at 55° C. Once injected, a focusing field of 150 V/cm with a 10 V/cm DC bias was applied at 55° C. for 20 min.

Figure 31A:
FIGS. 31A, 31B, and 31C show enrichment of cDNA obtained from an EZH2 Y641N mutation from a mixture of wild type and mutant amplicons using affinity SCODA with the application of a DC bias. Images were taken at 0 minutes (FIG. 31A), 10 minutes (FIG. 31B), and 20 minutes (FIG. 31C).
Figure 31A:
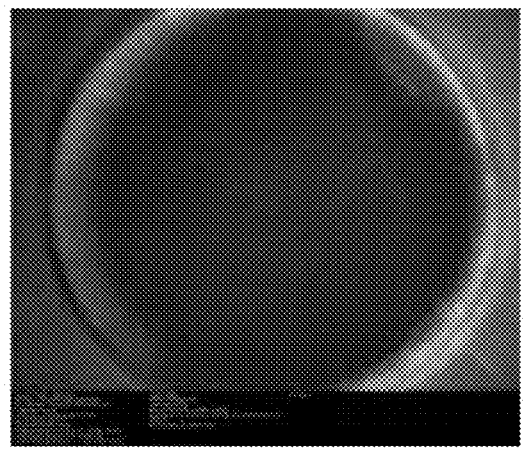
Figure 31B:
Figure 31B:
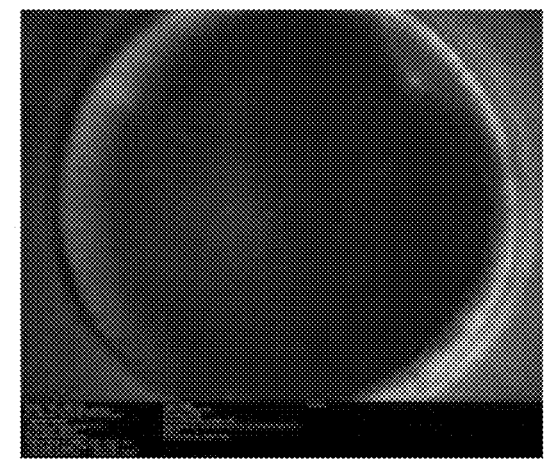
Figure 31C:
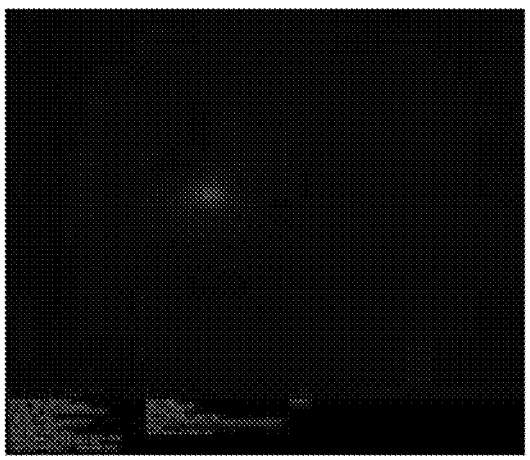
Figure 31C:
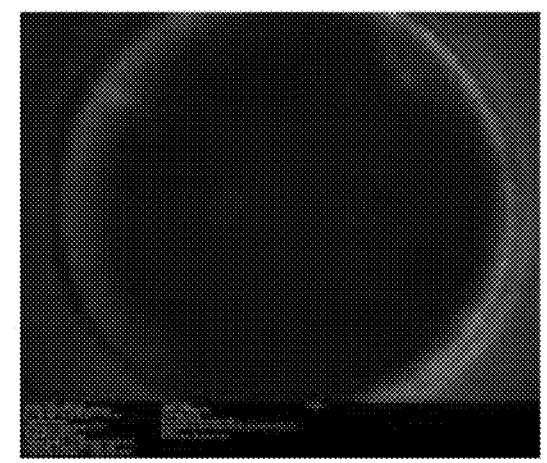

The result of this experiment is shown in FIGS. 31A, 31B, and 31C. The behavior of these sequences is qualitatively similar to the higher $T_m$ difference sequences shown in the above examples. The wild type (mismatch) nucleic acid is completely washed from the gel (images on the right hand side of the figure) while the mutant (perfect match) is driven towards the center of the gel (images on the left hand side of the figure). In this case the efficiency of focusing was reduced as some of the target reannealed forming double stranded DNA that did not interact with the gel bound probes.

The lower limit of detection with the optical system used was around 10 ng of singly labeled 460 bp DNA.

Example 41

Methylation Enrichment

The ability of affinity SCODA based purification to selectively enrich for molecules with similar binding energies was demonstrated by enriching for methylated DNA in a mixed population of methylated and unmethylated targets with identical sequence.

Figure 32:
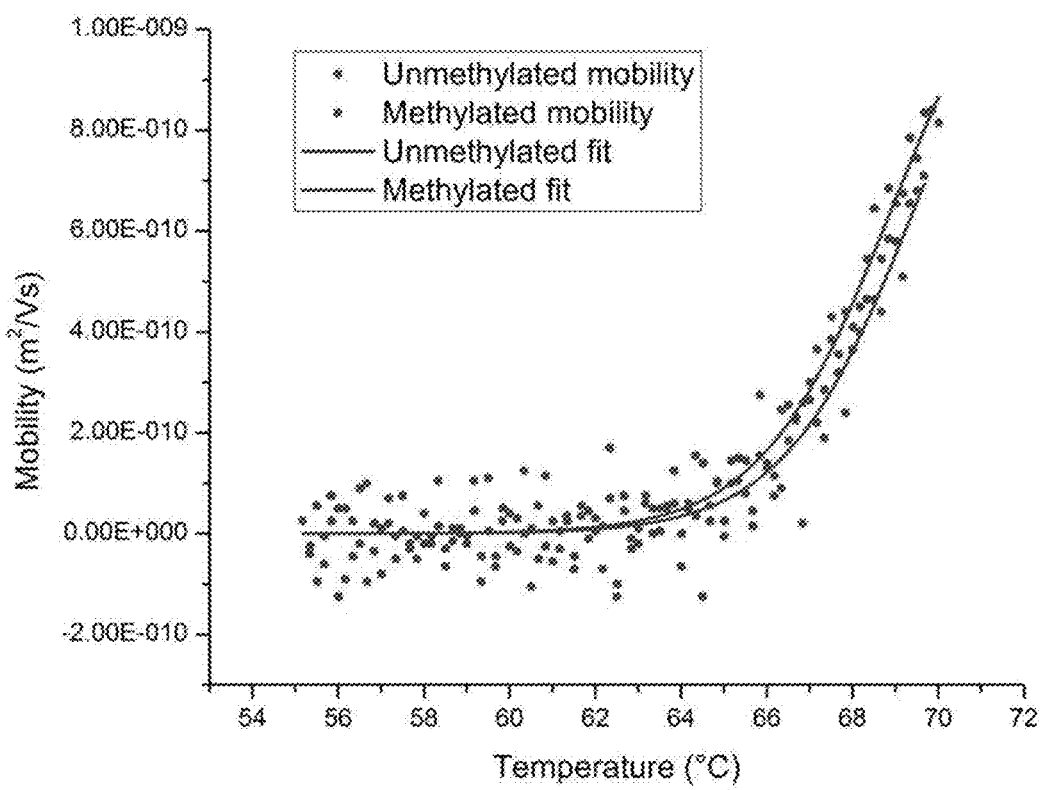
FIG. 32 shows experimental results for the measurement of mobility versus temperature for methylated and unmethylated targets. Data points were fit to equation (36). Data for the unmethylated target is fit to the curve on the left; data for the methylated target is fit to the curve on the right.

Fluorescently tagged PM oligonucleotides having the sequence set out in Table 4 (SEQ ID NO.:2) were synthesized by IDT with a single methylated cytosine residue within the capture probe region (residue 50 in the PM sequence of Table 4). DC mobility measurements of both the methylated and unmethylated PM strands were performed to generate velocity versus temperature curves as described above; this curve is shown in FIG. 32.

Fitting of these curves to equation (36) suggests that the difference in binding energy is around 0.19 kcal/mol at 69°

Figure 33:
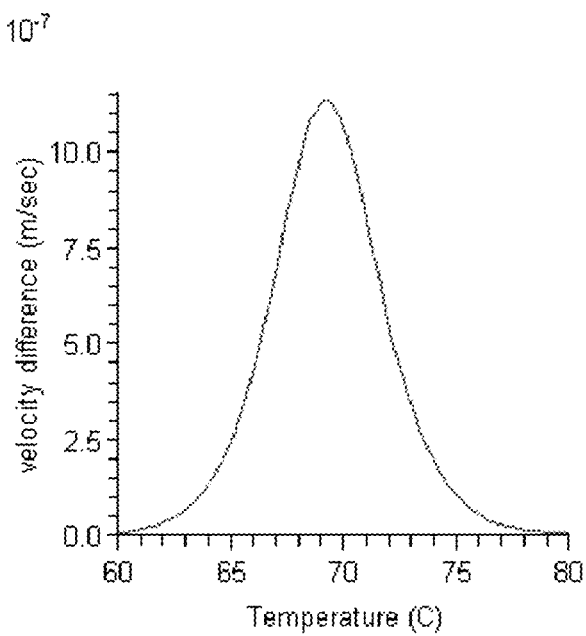
FIG. 33 shows the difference between the two mobility versus temperature curves which were fit to the data from FIG. 32. The maximum value of this difference is at 69.5° C., which is the temperature for maximum separation while performing affinity SCODA focusing with the application of a DC bias.

C., which is about a third of the thermal energy. (At 69° C. $k_b T=0.65$ kcal/mol.) The curve further suggests that separation of the two targets will be most effective at an operating temperature of around 69° C., where the two fragments have the greatest difference in mobility as shown in FIG. 33. In this example, the maximum value of this difference is at 69.5° C., which is the temperature for maximum separation while performing SCODA focusing under the application of a DC bias.

This temperature is slightly higher than that used in the above examples, and although it should result in better discrimination, focus times are longer as the higher temperature limits the maximum electric field strength one can operate at without boiling the gel.

Figure 34:
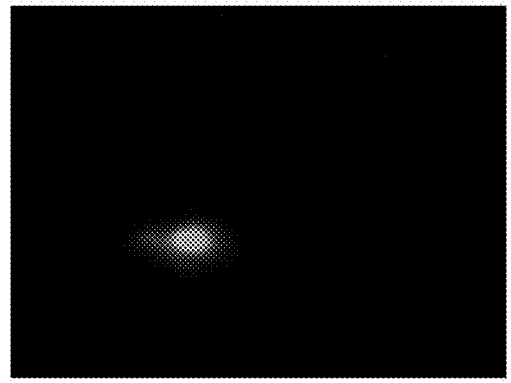
FIG. 34 shows experimental results for the separation of methylated (6-FAM, green) and unmethylated (Cy5, red) targets by using SCODA focusing with an applied DC bias.

Initial focusing tests showed that it is possible to separate the two targets by performing affinity SCODA focusing with a superimposed DC bias. FIG. 34 shows the result of an experiment where equimolar ratios of methylated and unmethylated targets were injected into a gel, focused with a period of 5 sec at a focusing field strength of 75 V/cm and a bias of 14 V/cm at 69° C. Methylated targets were labeled with 6-FAM (green, spot on right) and unmethylated targets were labeled with Cy5 (red, spot on left). The experiment was repeated with the dyes switched, with identical results.

Figure 35A:
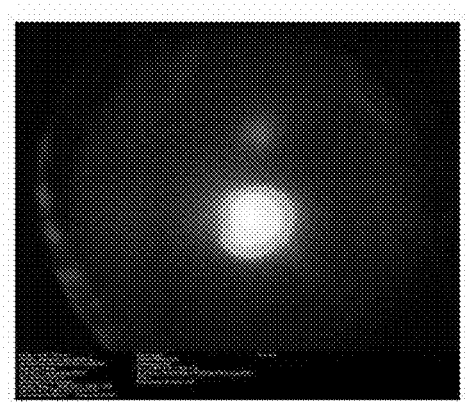
FIGS. 35A-35D show the separation of differentially methylated oligonucleotides using affinity SCODA.
Figure 35B:
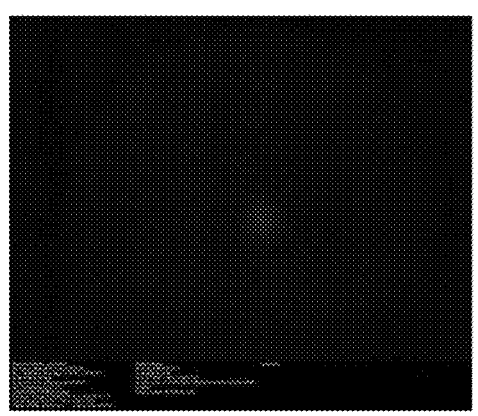
Figure 35C:
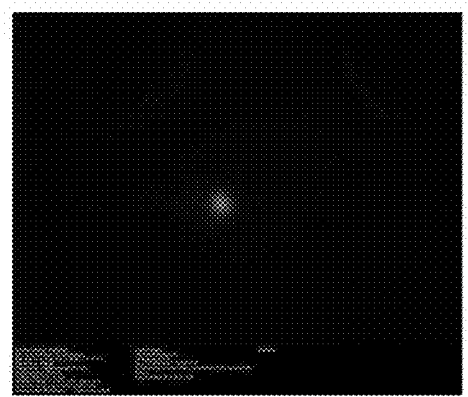
Figure 35D:
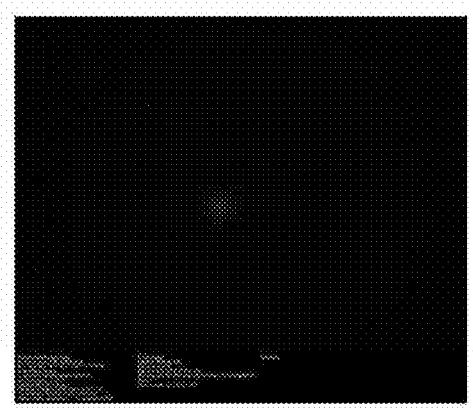

Achieving enrichment by completely washing the unmethylated target from the gel proved to be difficult using the same gel geometry for the above examples, as the gel buffer interface was obscured by the buffer wells preventing the use of visual feedback to control DC bias fields while attempting to wash the unmethylated target from the gel. To overcome this problem gels were cast in two steps: first a gel without probe oligonucleotides was cast in one of the arms of the gel and once the first gel had polymerized the remainder of the gel area was filled with gel containing probe oligonucleotides. The gels were cast such that the interface between the two was visible with the fluorescence imaging system. This system allowed for real time adjustments in the bias voltage so that the unmethylated target would enter the gel without immobilized probes and be quickly washed from the gel, while the methylated target could be retained in the focusing gel. FIGS. 35A-35D show the result of this experiment. FIGS. 35A and 35B show the results of an initial focus before washing unmethylated target from the gel for 10 pmol unmethylated DNA (FIG. 35A) and 0.1 pmol methylated DNA (FIG. 35B). FIGS. 35C and 35D show the results of a second focusing conducted after the unmethylated sequence had been washed from the gel for unmethylated and methylated target, respectively. All images were taken with the same gain and shutter settings.

In this experiment a 100 fold excess of unmethylated target was injected into the gel, focused to the center without any wash fields applied. The targets were then focused with a bias field to remove the unmethylated target, and finally focused to the center of the gel again for fluorescence quantification. Fluorescence quantification of these images indicates that the enrichment factor was 102 fold with losses of the methylated target during washing of 20%. This experiment was repeated with the dye molecules swapped (methylated Cy5 and unmethylated 6-FAM) with similar results.

Example 42

Multiplexed Affinity SCODA

Two different oligonucleotide probes described above, one having affinity for EZH2 and one having affinity for pUC, were cast in a gel at a concentration of 10 µM each to provide an affinity matrix containing two different immobilized probes. A 100 nucleotide target sequence with affinity for the EZH2 probe and a theoretical melting temperature of 62.3° C. was labeled with Cy5. A 100 nucleotide target sequence with affinity for the pUC probe and a theoretical melting temperature of 70.1° C. was labeled with FAM. The theoretical difference in melting temperature between the two target molecules is 7.8° C.

Figure 36A:
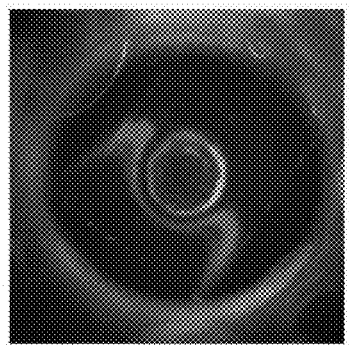
FIGS. 36A-36K show the results of the differential separation of two different sequences in the same affinity matrix using different oligonucleotide probes.
Figure 36B:
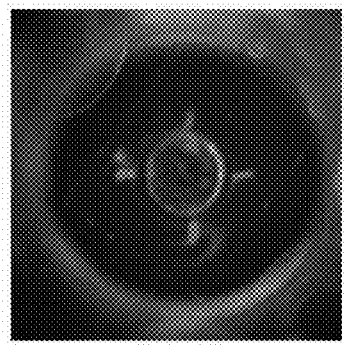
Figure 36C:
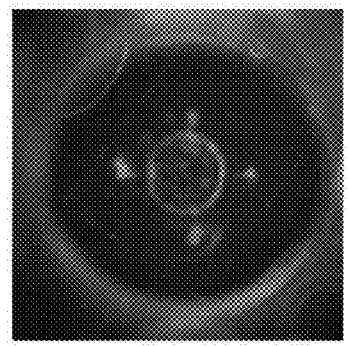
Figure 36D:
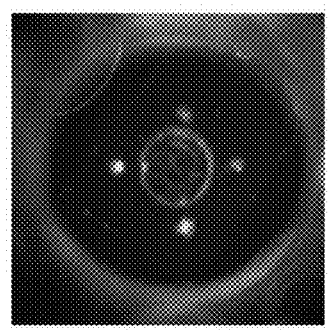
Figure 36E:
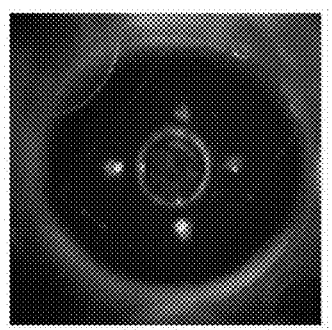

The target molecules were loaded on the affinity gel (FIG. 36A), and focusing was conducted with the temperature beneath the gel boat maintained at 55° C. (FIGS. 36B, focusing after two minutes, and 36C, after four minutes). The EZH2 target focused under these conditions (four red spots), while the pUC target focused only weakly under these conditions (three diffuse green spots visible on the gel). The central extraction well did not contain buffer during the initial portions of this experiment, resulting in the production of four focus spots, rather than a single central focus spot. The temperature beneath the gel was then increased to 62° C., a temperature increase of 7° C. (FIG. 36D, focusing two minutes after temperature increase, and 36E, after four minutes), resulting in the formation of four clear focus spots for the pUC target. The EZH2 target remained focused in four tight spots at this higher temperature.

Figure 36F:
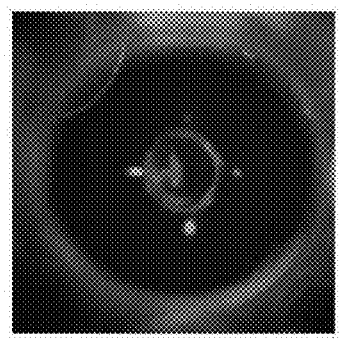
Figure 36G:
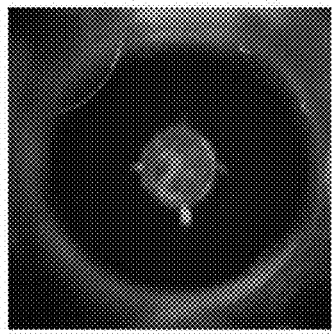
Figure 36H:
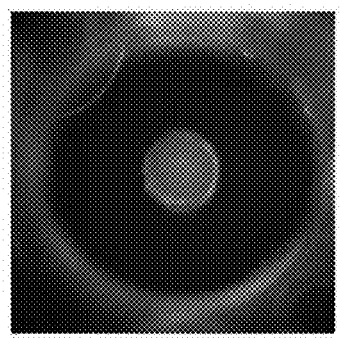

The temperature beneath the gel was reduced to 55° C. and buffer was added to the central extraction well. Application of SCODA focusing fields at this temperature resulted in the EZH2 target being selectively concentrated into the central extraction well (diffuse red spot visible at the center of FIG. 36F, 0.5 minutes, and 36G, 1 minute) while the pUC target remained largely focused in four spots outside the central extraction well. The temperature beneath the gel was increased to 62° C., a temperature increase of 7° C. Within two minutes, the pUC target had been focused into the central extraction well (FIG. 36H, diffuse red and green fluorescence visible at the center of the gel).

Figure 12C:
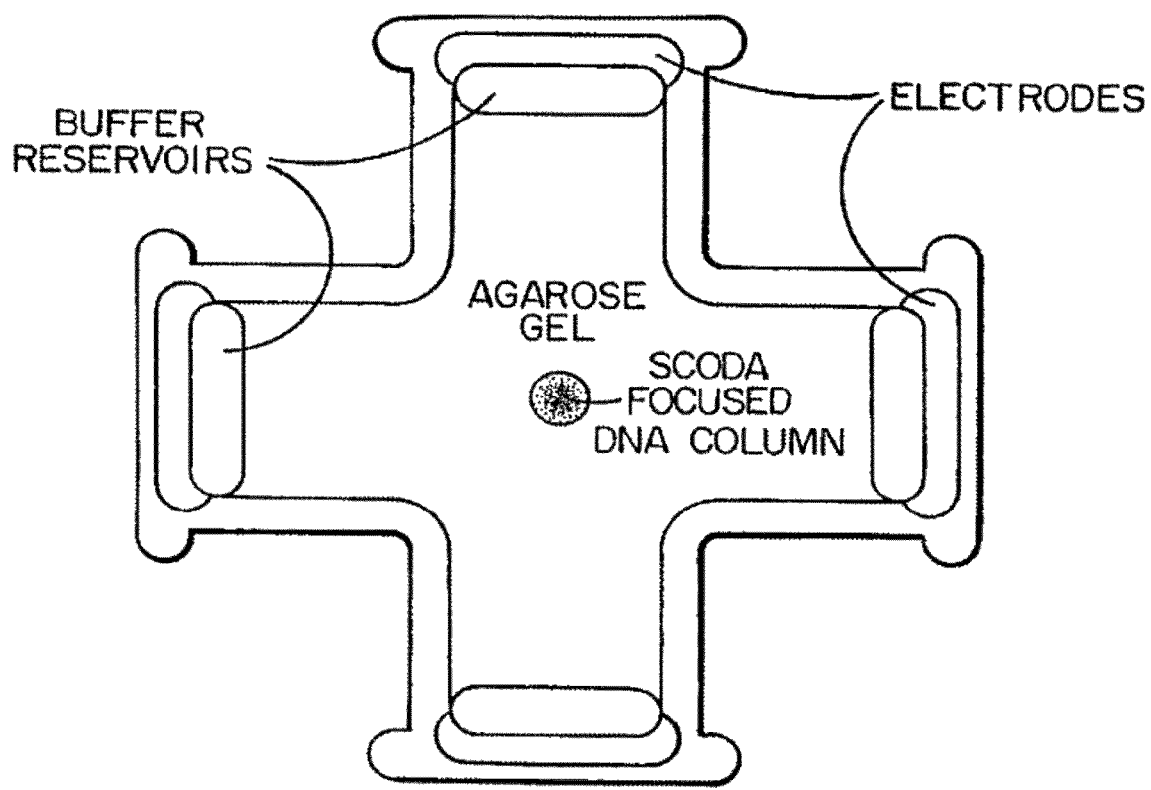
FIG. 12C is a plan view of an extraction apparatus similar to that shown in FIG. 12A.
Figure 36I:
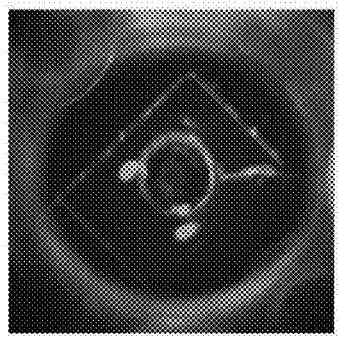
Figure 36J:
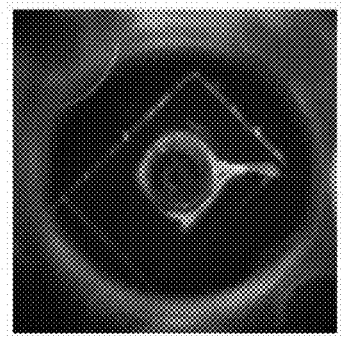
Figure 36K:
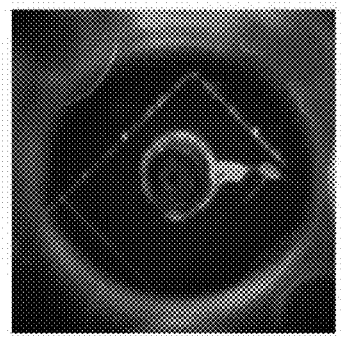

A second experiment was conducted under similar conditions as the first. After focusing the EZH2 target at 55° C. and the pUC target at 62° C. as described above, a DC washing bias was applied to the gel with the temperature beneath the gel maintained at 55° C. Under these conditions, the EZH2 target experienced a greater bias velocity than the pUC target. The focus spot for the EZH2 target shifted more quickly after the application of the bias field (red spot moving to the right of the gel in FIG. 36I, 6 minutes after application of bias field, 36J, after 12 minutes, and 36K, after 18 minutes). The focus spot for the EZH2 target was also shifted a farther distance to the right within the gel. In contrast, the focus spot for the pUC target shifted more slowly (initial green focus spots still largely visible in FIG. 36I after 6 minutes, shifting to the right through FIG. 36J, 12 minutes, and 36K, 18 minutes), and was not shifted as far to the right as the focus spot for the EZH2 target by the washing bias.

Example 43

Affinity SCODA Yield vs Purity

Because affinity SCODA relies on repeated interactions between target and probe to generate a non-dispersive velocity field for target molecules, while generating a dispersive field for contaminants (so long as a washing bias is applied), high specificity can be achieved without sacrificing yield. If one assumes that the final focus spot is Gaussian, which is justified by calculating the spot size for a radial velocity field balanced against diffusion, then the spot will extend all the way out to the edge of the gel. Here diffusion can drive targets off the gel where there is no restoring focusing force and an applied DC bias will sweep targets away from the gel where they will be lost. In this manner the losses for ssSCODA can scale with the amount of time one applies a wash field; however the images used to generate FIGS. 27A-27D indicate that in that example the focus spot has a full width half maximum (FWHM) of 300 μm and under bias it sits at approximately 1.0 mm from the gel center. If it is assumed that there is 10 fmol of target in the focus spot, then the concentration at the edge of the gel where a bias is applied is $1e^{-352}$ M; that is, there are essentially zero target molecules present at the edges of the gel where they can be lost under DC bias. This implies that the rate at which losses accumulate due to an applied bias (i.e. washing step) is essentially zero. Although the desired target may be lost from the system in other ways, for example by adsorbing to the sample well prior to injection, running off the edge of the gel during injection, re-annealing before or during focusing (in the case of double stranded target molecules), or during extraction, all of these losses are decoupled from the purity of the purified target.

Where a component (e.g. a power supply, electrode, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for enriching a sample, the method comprising the steps of:
   obtaining a sample comprising a non-target nucleic acid and a target nucleic acid, the target nucleic acid and the non-target nucleic acid differing by an insertion, a deletion, or a polymorphism at a position of interest, but being no more than 50 bases different in total length, wherein the target to non-target ratio in the sample is X; and
   enriching for the target nucleic acid by applying a time-varying driving field to the sample in the presence of a separation medium,
   wherein after enrichment the ratio of target nucleic acid to non-target nucleic acid is Y, wherein Y is at least 10 times greater than X.

2. The method of claim 1, wherein the target and the non-target nucleic acids differ in length by 20 or fewer bases.

3. The method of claim 2, wherein the target and the non-target nucleic acids differ in length by 10 or fewer bases.

4. The method of claim 1, wherein the target and the non-target nucleic acids have different methylation or acetylation patterns.

5. The method of claim 1, wherein the sample is a biological sample.

6. The method of claim 5, wherein the biological sample comprises tissue, blood, sputum, sweat, urine, feces, tears, aspirate, or a combination thereof.

7. The method of claim 6, wherein the biological sample is from a human.

8. The method of claim 1, further comprising identifying the target nucleic acid.

9. The method of claim 8, wherein identifying comprises sequencing at least a portion of the target nucleic acid, contacting the target nucleic acid with a labeled moiety, or an amplification-based detection.

10. The method of claim 1, wherein the presence of the target nucleic is indicative of a disorder.

11. The method of claim 10, wherein the disorder is a genetic disorder.

12. The method of claim 10, wherein the disorder is cancer.

13. The method of claim 1, wherein Y is at least 100 times greater than X.

14. The method of claim 13, wherein Y is at least 1,000 times greater than X.

15. The method of claim 1, wherein enriching comprises applying a periodic electric field to the sample.

16. The method of claim 15, further comprising periodically changing the temperature of the medium.

17. The method of claim 1, wherein the non-target and target nucleic acids each comprise 5000 or fewer bases.

18. The method of claim 1, wherein the non-target and target nucleic acids each comprise 100 or more bases.

19. The method of claim 1, wherein the non-target nucleic acid is a wild-type nucleic acid.

20. The method of claim 1, wherein at least 20% of the target nucleic acid in the sample comprising a non-target nucleic acid and a target nucleic acid is recovered after enrichment.

21. The method of claim 20, wherein at least 50% of the target nucleic acid in the sample comprising a non-target nucleic acid and a target nucleic acid is recovered after enrichment.

22. The method of claim 1, wherein the sample is simultaneously enriched for more than one target nucleic acid.

* * * * *